United States Patent
Desai et al.

(10) Patent No.: US 12,128,152 B2
(45) Date of Patent: Oct. 29, 2024

(54) SYSTEM AND METHOD FOR INJECTION AND RETRACTION OF FLUID

(71) Applicant: Relavo, Inc., Brooklyn, NY (US)

(72) Inventors: Tejasvi Desai, Brooklyn, NY (US); Rahul Swaminathan, Fremont, CA (US); Jerry Zhang, Glen Allen, VA (US); Angela Mak, Cerritos, CA (US); Xiaodong Huo, Santa Clara, CA (US); Sarah Lee, Brooklyn, NY (US); Anna Bailey, Brooklyn, NY (US); Yupin Shi, Queens, NY (US)

(73) Assignee: Relavo, Inc., Brooklyn, NY (US)

( * ) Notice: Subject to any disclaimer, the term of this patent is extended or adjusted under 35 U.S.C. 154(b) by 0 days.

(21) Appl. No.: 18/340,477

(22) Filed: Jun. 23, 2023

(65) Prior Publication Data
US 2023/0330289 A1    Oct. 19, 2023

Related U.S. Application Data

(63) Continuation-in-part of application No. PCT/US2021/065039, filed on Dec. 23, 2021.
(Continued)

(51) Int. Cl.
*A61M 1/28* (2006.01)
*A61L 2/18* (2006.01)
(Continued)

(52) U.S. Cl.
CPC ............ *A61L 2/18* (2013.01); *A61M 1/1524* (2022.05); *A61M 1/282* (2014.02); *A61M 39/162* (2013.01); *A61L 2202/24* (2013.01)

(58) Field of Classification Search
CPC .... A61L 2/18; A61L 2202/24; A61M 1/1524; A61M 1/282; A61M 39/162; A61M 1/159; A61M 1/169; A61M 1/28
See application file for complete search history.

(56) References Cited

U.S. PATENT DOCUMENTS 3,419,346 A    12/1968 Nicholas
4,209,013 A    6/1980 Alexander et al.
(Continued)

FOREIGN PATENT DOCUMENTS

CN    101986776 A    3/2011
CN    102112164 A    6/2011
(Continued)

OTHER PUBLICATIONS

Ashley, John, et al., "Effect of UV Light on Disinfection of Peritoneal Dialysis Catheter Connections", Perit Dial Int. 2017; 37(1): 109-111.
(Continued)

*Primary Examiner* — Regina M Yoo
(74) *Attorney, Agent, or Firm* — COOLEY LLP

(57) ABSTRACT

Aspects of the present disclosure relate to systems and methods for injection and retraction of a fluid. The system includes a switch configured to be activated, wherein activation of the switch activates an electrical control system. The system further includes a linear actuator that interfaces with the electrical control system. The electrical control system causes the linear actuator to depress a plunger, keep the plunger depressed for a predetermined time, and retract the plunger after the predetermined time. The system further includes a fluid reservoir engageable with the plunger, wherein the depression of the plunger causes fluid to be injected from the fluid reservoir into a connector and the retraction of the plunger causes fluid to be retracted into the fluid reservoir and out of the connector.

29 Claims, 36 Drawing Sheets

Related U.S. Application Data

(60) Provisional application No. 63/129,675, filed on Dec. 23, 2020.

(51) Int. Cl.
*A61M 1/14* (2006.01)
*A61M 39/16* (2006.01)

(56) References Cited

U.S. PATENT DOCUMENTS

| | | | |
|---|---|---|---|
| 4,346,703 A | 8/1982 | Dennehey et al. | |
| 4,417,890 A | 11/1983 | Dennehey et al. | |
| 4,432,764 A | 2/1984 | Lopez | |
| 4,432,766 A | 2/1984 | Bellotti et al. | |
| 4,440,207 A | 4/1984 | Genatempo et al. | |
| 4,545,956 A | 10/1985 | Ciszewski et al. | |
| 4,636,204 A | 1/1987 | Christopherson et al. | |
| 4,810,241 A | 3/1989 | Rogers | |
| 5,190,534 A | 3/1993 | Kendell | |
| 5,205,824 A | 4/1993 | Mazur | |
| 5,433,705 A | 7/1995 | Giebel et al. | |
| 5,527,287 A | 6/1996 | Miskinyar | |
| 5,603,701 A | 2/1997 | Fischer | |
| 5,733,270 A | 3/1998 | Ling et al. | |
| 6,106,502 A | 8/2000 | Richmond | |
| 6,228,047 B1 | 5/2001 | Dadson | |
| 6,402,717 B1 | 6/2002 | Reilly et al. | |
| 6,723,074 B1 | 4/2004 | Halseth | |
| 6,830,560 B1 | 12/2004 | Gross et al. | |
| 7,044,737 B2 | 5/2006 | Fu | |
| 7,140,592 B2 | 11/2006 | Phillips | |
| 7,198,611 B2 | 4/2007 | Connell et al. | |
| 7,645,274 B2 | 1/2010 | Whitley | |
| 7,727,220 B2 | 6/2010 | Wieslander et al. | |
| 7,857,793 B2 | 12/2010 | Raulerson et al. | |
| 7,918,825 B2 | 4/2011 | O'Connor et al. | |
| 7,922,701 B2 | 4/2011 | Buchman | |
| 8,585,681 B2 | 11/2013 | Boenig et al. | |
| 8,617,465 B2 | 12/2013 | Lee et al. | |
| 8,617,482 B2 | 12/2013 | Tryggvason et al. | |
| 8,622,996 B2 | 1/2014 | Ziebol et al. | |
| 8,858,493 B2 | 10/2014 | Biesel | |
| 8,951,233 B2 | 2/2015 | Mansour | |
| 9,044,553 B2 | 6/2015 | James et al. | |
| 9,259,284 B2 | 2/2016 | Rogers et al. | |
| 9,352,142 B2 | 5/2016 | Ziebol et al. | |
| 9,421,314 B2 | 8/2016 | Plahey et al. | |
| 9,572,904 B2 | 2/2017 | Ferlic | |
| 9,579,459 B2 | 2/2017 | Jennings et al. | |
| 10,155,056 B2 | 12/2018 | Solomon et al. | |
| 10,166,336 B2 | 1/2019 | Lumme et al. | |
| 10,195,000 B2 | 2/2019 | Rogers et al. | |
| 10,525,250 B1 | 1/2020 | Ziebol et al. | |
| 10,603,481 B2 | 3/2020 | Avula et al. | |
| 10,722,653 B2 | 7/2020 | Kapas et al. | |
| 10,737,019 B2 | 8/2020 | Henderson et al. | |
| 11,464,961 B2 | 10/2022 | Burkholz | |
| 2004/0103951 A1 | 6/2004 | Osborne et al. | |
| 2005/0234407 A1* | 10/2005 | Spohn | A61M 39/10 604/122 |
| 2005/0234428 A1* | 10/2005 | Spohn | A61M 5/007 604/533 |
| 2010/0113983 A1 | 5/2010 | Heckerman et al. | |
| 2010/0172794 A1 | 7/2010 | Ferlic et al. | |
| 2012/0111368 A1 | 5/2012 | Rahimy et al. | |
| 2013/0303996 A1 | 11/2013 | Rasooly et al. | |
| 2014/0276376 A1* | 9/2014 | Rohde | A61M 1/1605 604/29 |
| 2014/0334974 A1 | 11/2014 | Rasooly et al. | |
| 2015/0335530 A1 | 11/2015 | Aguerre et al. | |
| 2015/0352348 A1 | 12/2015 | Murphy-Chutorian et al. | |
| 2016/0082138 A1 | 3/2016 | Kermode et al. | |
| 2016/0151646 A1 | 6/2016 | Bonutti et al. | |
| 2016/0184510 A1 | 6/2016 | Kamen et al. | |
| 2016/0235916 A1 | 8/2016 | Edwards et al. | |
| 2017/0035959 A1 | 2/2017 | Riley et al. | |
| 2017/0182305 A1 | 6/2017 | Kermode et al. | |
| 2017/0333619 A1 | 11/2017 | Cowan et al. | |
| 2018/0209532 A1 | 7/2018 | Rüsing | |
| 2020/0108197 A1 | 4/2020 | Powers et al. | |
| 2020/0139102 A1 | 5/2020 | Ziebol et al. | |
| 2022/0016409 A1 | 1/2022 | Lee et al. | |
| 2022/0226629 A1 | 7/2022 | Ziebol et al. | |
| 2022/0288376 A1 | 9/2022 | Ziebol et al. | |
| 2023/0331613 A1* | 10/2023 | Wieslander | C02F 1/441 |

FOREIGN PATENT DOCUMENTS

| | | |
|---|---|---|
| CN | 102137692 A | 7/2011 |
| CN | 104080496 A | 10/2014 |
| CN | 104363928 A | 2/2015 |
| CN | 206642137 U | 11/2017 |
| EP | 0092528 A1 | 10/1983 |
| EP | 0093837 A1 | 11/1983 |
| EP | 1240913 B1 | 12/2004 |
| EP | 2992870 A1 | 3/2016 |
| EP | 2654843 B1 | 9/2018 |
| ES | 2572578 T3 | 6/2016 |
| JP | H06501853 A | 3/1994 |
| JP | H10216224 A | 8/1998 |
| JP | H11507562 A | 7/1999 |
| JP | 2017029785 A | 2/2017 |
| KR | 20160075496 A | 6/2016 |
| WO | WO-8700441 A1 | 1/1987 |
| WO | WO-9700095 A1 | 1/1997 |
| WO | WO-2008086631 A1 | 7/2008 |
| WO | WO-2020101884 A1 | 5/2020 |
| WO | WO-2022140649 A1 | 6/2022 |

OTHER PUBLICATIONS

Author Unknown, "Baxter Achieves Regulatory Milestone for new Peritoneal Dialysis Technology", Baxter, Press Release dated May 3, 2017, 3 pgs.

Author Unknown, "Baxters AMIA with sharesource telehealth platform for home dialysis named a winner of 15th annual Chicago innovation awards", MDLinx, retrieved from webpage https://https://www.mdlinx.com/journal-summaries/2016/10/27/6921307/print-preview?spec=internal-medicine, on Aug. 21, 2023, 2 pgs.

Author Unknown, "ClearGuard™ HD Antimicrobial Barrier Caps for Hemodialysis Catheters" icumedical, retrieved from webpage https://www.icumed.com/products/specialty/renal/clearguard-hd, on Aug. 18, 2023, 7 pgs.

Author Unknown, "Current state of organ donation and transplantation: Transplant trends", UNOS, retrieved from webpage https://www.https://unos.org/data/#transplants_by_organ_type+year+2016, on Aug. 21, 2023, 8 pgs.

Author Unknown, "DualCap® Disinfection & Protection System", Merit Medical, retrieved from webpage https://www.merit.com/cardiac-intervention/interventional-fluid-management/infection-prevention/dualcap/, on Aug. 18, 2023, 6 pgs.

Author Unknown, "End Stage Renal Disease (ESRD) Prospective Payment System (PPS)", Centers for Medicare & Medicaid Services, retrieved from website https://www.cms.gov/medicare/medicare-fee-for-service-payment/esrdpayment on Aug. 21, 2023, 7 pgs.

Author Unknown, "Fact Sheet: End Stage Renal Disease (ESRD) and Dialysis-Related Services", CMS, CGS Administration, originated Sep. 5, 2014, revised Dec. 13, 2021, 3 pgs.

Author Unknown, "Improving Patient Outcomes—Firefly", PuraCath, retrieved from webpage https://www.puracath.com/, on Aug. 18, 2023, 4 pgs.

Author Unknown, "Isopropanol", U.S. National Library of Medicine, Hazardous Substance Data Bank (Annotation Record), Jan. 19, 2012, 85 pgs.

Author Unknown, "Kidney Disease in Children", National Institute of Diabetes and Digestive and Kidney Diseases, retrieved from webpage https://www.niddk.nih.gov/health-information/kidney-disease/children, on Aug. 21, 2023, 12 pgs.

(56) References Cited

OTHER PUBLICATIONS

Author Unknown, "Kidney Disease Statistics for the United States", National Institute of Diabetes and Digestive and Kidney Diseases, retrieved from webpage https://www.niddk.nih.gov/health-information/health-statistics/kidney-disease, on Aug. 21, 2023, 4 pgs.
Author Unknown, "Opinion on Polyaminopropyl Biguanide (PHMB)—Submission III", European Commission Scientific Committee on Consumer Safety, published on Apr. 7, 2017, 90 pgs.
Author Unknown, "Peritoneal Dialysis", American Kidney Fund, retrieved from website https://www.https://www.kidneyfund.org/treatments/dialysis/peritoneal-dialysis#how_does_pd_work, on Aug. 21, 2023, 8 pgs.
Author Unknown, "Renal Disease Treatments: Products and Therapies", ProQuest LLC, Jun. 30, 2016, 3 pgs.
Author Unknown, "Tour of Automated Peritoneal Dialysis (APD) Machines—DaVita", DaVita, retrieved from webpage https://www.davita.com/treatment-options/home-peritoneal-dialysis/what-is-peritoneal-disease-/tour-of-automated-peritoneal-dialysis-(apd)-machinest/t/5486.html on Aug. 18, 2023, 5 pgs.
Author Unknown, "SwabCap™ Disinfecting Cap for Needle free Connectors", icumedical, retrieved from webpage https://www.icumed.com/products/infusion-therapy/iv-consumables/disinfecting-caps/swabcap, on Aug. 18, 2023, 4 pgs.
Bernardini, J., et al., "A randomized trial of *Staphylococcus aureus* prophylaxis in peritoneal dialysis patients: mupirocin calcium ointment 2% applied to the exit site versus cyclic oral rifampin", Am J Kidney Dis. May 1996; 27(5): 695-700.
Bernardini, Judith, et al., "Randomized, Double-Blind Trial of Antibiotic Exit Site Cream for Prevention of Exit Site Infection in Peritoneal Dialysis Patients", J Am Soc Nephrol. Feb. 2005; 16(2): 539-45.
Bianchi, Paolo, et al. "Antisepsis", Contributions to Nephrology Disinfection by Sodium Hypochlorite: Contrib Nephrol. 2007; 154: 1-6.
Brunelli, Steven M., "Cluster-Randomized Trial of Devices to Prevent Catheter-Related Bloodstream Infection", J Am Soc Nephrol. Apr. 2018; 29(4): 1336-1343.
Carovac, Aladin, "Application of ultrasound in medicine", Acta Inform Med. Sep. 2011; 19(3): 168-71.
De Camargo, Maria Fernanda Carvalo, et al., "Cost analysis of substitutive renal therapies in children", J Pediatr (Rio J). Jan.-Feb. 2018; 94(1): 93-99.
Department of Health & Human Services, "Section 510(k) Premarket Notification Letter from Department of Health & Human Services", PuraCath Medical, Inc., dated Jan. 20, 2016, 7 pgs.
Devoe, Daniel J., et al., "Patient Education and Peritoneal Dialysis Modality Selection: A Systematic Review and Meta-analysis", Am J Kidney Dis. Sep. 2016; 68(3): 422-33.
Duckhouse, H., et al., "The effect of sonication on microbial disinfection using hypochlorite", Ultrason Sonochem. May 2004; 11(3-4): 173-6.
Filler, Guido, et al., "Methods of assessing renal function", Pediatr Nephrol. Feb. 2014; 29(2): 183-92.
Firanek, Catherine, et al., "Comparison of Disinfection Procedures on the Catheter Adapter-Transfer Set Junction", Perit Dial Int. Mar.-Apr. 2016; 36(2): 225-7.
Grassmann, Aileen, "ESRD patients in 2004: global overview of patient numbers, treatment modalities and associated trends", Nephrol Dial Transplant. Dec. 2005; 20(12):2587-93.
Guo, Yi, et al., "In Vivo Bioluminescence Imaging to Evaluate Systemic and Topical Antibiotics against Community-Acquired Methicillin-Resistant *Staphylococcus aureus*-Infected Skin Wounds in Mice", Antimicrob Agents Chemother. Feb. 2013; 57(2): 855-63.
Harambat, Jerome, et al. "Epidemiology of chronic kidney disease in children", Pediatr Nephrol. Mar. 2012; 27(3): 363-73.
Heaf, James G., et al., "Initial survival advantage of peritoneal dialysis relative to haemodialysis", Nephrol Dial Transplant. Jan. 2002; 17(1): 112-7.

International Preliminary Report on Patentability issued by the World Intellectual Property Office for Application No. PCT/US2021/065039 mailed on Jun. 13, 2023, 14 pages.
International Search Report and Written Opinion issued by the World Intellectual Property Office for Application No. PCT/US2021/065039 mailed on May 27, 2022, 20 pages.
Invitation to Pay Additional Fees and, Where Applicable, Protest Fee issued by the World Intellectual Property Office for Application No. PCT/US2021/065039 mailed on Apr. 4, 2022, 15 pages.
Jardine, Meg J., "A Trial of Extending Hemodialysis Hours and Quality of Life", J Am Soc Nephrol. Jun. 2017; 28(6): 1898-1911.
Joyce, E., et al., "The development and evaluation of ultrasound for the treatment of bacterial suspensions. A study of frequency, power and sonication time on cultured *Bacillus* species", Ultrason Sonochem. Oct. 2003; 10(6): 315-8.
Just, Paul M., et al., "Reimbursement and economic factors influencing dialysis modality choice around the world", Nephrol Dial Transplant. Jul. 2008; 23(7): 2365-73.
Karger, R., et al., "Water treatment using ultrasonic assistance: A review", Semantic Scholar, published 2012, 15 pgs.
Karopadi, Akash Nayak, et al., "The role of economies of scale in the cost of dialysis across the world: a macroeconomic perspective", Nephrol Dial Transplant. Apr. 2014; 29(4): 885-92.
Laliberte, Gina, et al., "Literature Review of the Effects of Ultrasonic Waves on Cyanobacteria, Other Aquatic Organisms, and Water Quality", Wisconsin Department of Natural Resources, Research Report 195, Mar. 2014, 20 pgs.
Lew, Susie Q., et al., "Adoption of Telehealth: Remote Biometric Monitoring Among Peritoneal Dialysis Patients in the United States", Perit Dial Int. Sep.-Oct. 2017; 37(5): 576-578.
Liakopoulos, Vassilios, et al., "Peritoneal dialysis-related infections recommendations: 2016 update. What is new?", Int Urol Nephrol. Dec. 2017; 49(12): 2177-2184.
Liu, Xu, et al., "Low-Frequency Ultrasound Enhances Antimicrobial Activity of Colistin-Vancomycin Combination against Pan-Resistant Biofilm of Acinetobacter baumannii", Ultrasound Med Biol. Aug. 2016; 42(8): 1968-75.
Lorente, Leonardo, "Antimicrobial-impregnated catheters for the prevention of catheter-related bloodstream infections", World J Crit Care Med. May 4, 2016; 5(2): 137-42.
Maki, D.G., et al., "Prospective randomised trial of povidone-iodine, alcohol, and chlorhexidine for prevention of infection associated with central venous and arterial catheters", Lancet. Aug. 10, 1991; 338(8763): 339-43.
Malhi, Hardip, "Enteral tube feeding: using good practice to prevent infection", Br J Nurs. Jan. 12, 2017; 26(1): 8-14.
Marron, Belen, et al., "Analysis of patient flow into dialysis: role of education in choice of dialysis modality", Perit Dial Int. Feb. 2005; 25 Suppl 3: S56-9.
Martin, Amy, "Dialysis Availability in Rural America", South Carolina Rural Health Research & Policy Centers, Jan. 2013, 30 pgs.
Piraino, Beth, "Innovations in Treatment Delivery, Risk of Peritonitis, and Patient Retention on Peritoneal Dialysis", Semin Dial. Mar. 2017; 30(2): 158-163.
Prakash, Suma, et al., "Travel distance and home dialysis rates in the United States", Perit Dial Int. Jan.-Feb. 2014 34(1): 24-32.
Puskarova, Andrea, et al., "The antibacterial and antifungal activity of six essential oils and their cyto/genotoxicity to human HEL 12469 cells", Sci Rep. Aug. 15, 2017; 7(1): 8211, 11 pgs.
Ribitsch, Werner, et al., "Effects of a pre-dialysis patient education program on the relative frequencies of dialysis modalities", Perit Dial Int. Jul.-Aug. 2013; 33(4): 367-71.
Schrank, Gregory, et al., "Breaking the Chain of Infection in Older Adults: A Review of Risk Factors and Strategies for Preventing Device-Related Infections", Infect Dis Clin North Am. Dec. 2017; 31(4): 649-671.
Schreiber Jr., Martin J., "Changing Landscape for Peritoneal Dialysis: Optimizing Utilization", Semin Dial. Mar. 2017; 30(2): 149-157.
Sethna, Christine B., "Risk Factors for and Outcomes of Catheter-Associated Peritonitis in Children: The SCOPE Collaborative", Clin J Am Soc Nephrol. Sep. 7, 2016; 11(9): 1590-1596.

(56) References Cited

OTHER PUBLICATIONS

Shaobin, Gu, et al., "Effects of sound exposure on the growth and intracellular macromolecular synthesis of *E. coli* k-12", Peer J. Apr. 7, 2016; 4: e1920, 13 pgs.

Strong, Andrew T., "Feeding the gut after revisional bariatric surgery: The fate of 126 enteral access tubes", Surg Obes Relat Dis. Jul. 2018; 14(7): 986-991.

Suri, Rita S., et al., "The risk of hospitalization and modality failure with home dialysis", Kidney Int. Aug. 2015; 88(2): 360-8.

Thompson, John M., "Oral-Only Linezolid-Rifampin Is Highly Effective Compared with Other Antibiotics for Periprosthetic Joint Infection: Study of a Mouse Model", J Bone Joint Surg Am. Apr. 19, 2017; 99(8): 656-665.

United States Government Accountability Office, "End-Stage Renal Disease Medicare Payment Refinements Could Promote Increased Use of Home Dialysis." Report to the Subcommittee on Health, Committee on Ways and Means, House of Representatives, Nov. 16, 2015, 51 pgs.

Wang, Virginia, et al., "Impacts of Geographic Distance on Peritoneal Dialysis Utilization: Refining Models of Treatment Selection", Health Serv Res., Feb. 2017, 21 pgs.

Wang, Virginia, et al., "Longitudinal analysis of market factors associated with provision of peritoneal dialysis services", Med Care Res Rev. Oct. 2011; 68(5): 537-58.

Zhang, Jingjing, et al., "Machine-learning algorithms define pathogen-specific local immune fingerprints in peritoneal dialysis patients with bacterial infections", Kidney Int. Jul. 2017; 92(1): 179-191.

Non-Final Office Action for U.S. Appl. No. 18/340,477 dated Jan. 5, 2024, 8 pages.

\* cited by examiner

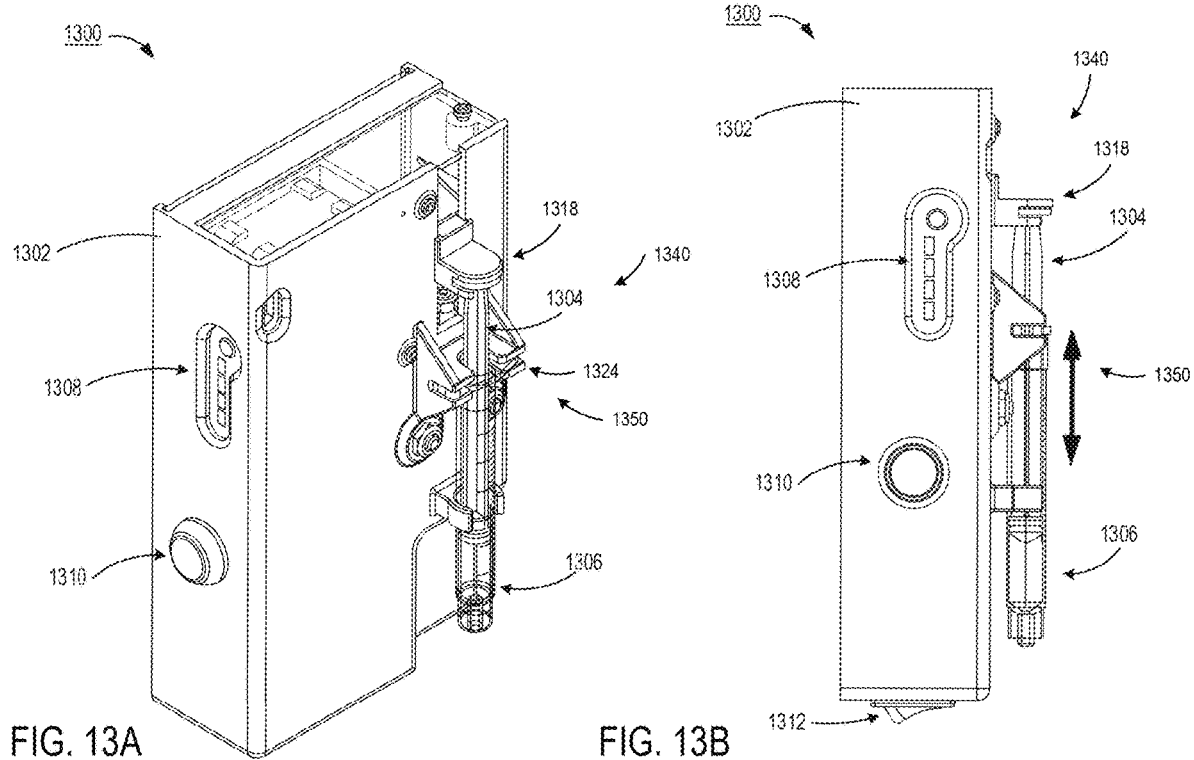

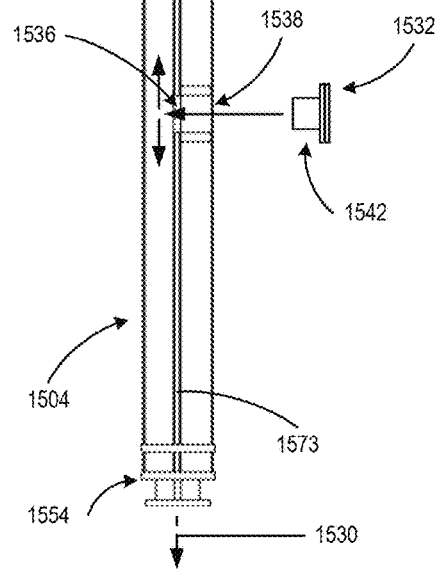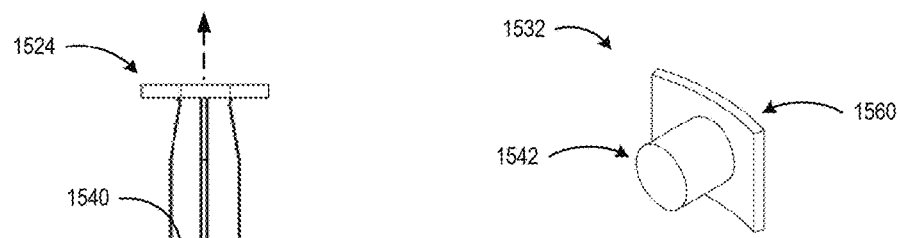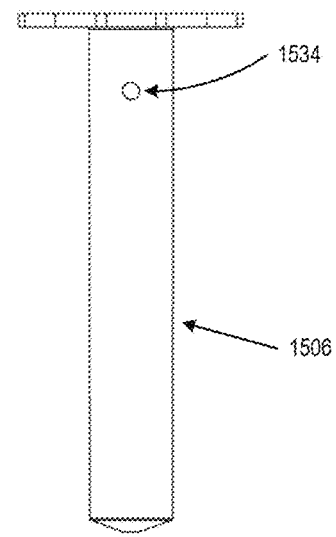
FIG. 15A
FIG. 15B
FIG. 15C

SYSTEM AND METHOD FOR INJECTION AND RETRACTION OF FLUID

CROSS-REFERENCE TO RELATED APPLICATIONS

This application is a continuation in part of International Patent Application No. PCT/US2021/065039, filed Dec. 23, 2021, and titled System and Method for Injection and Retraction of Fluid," which claims priority to U.S. Provisional Patent Application No. 63/129,675, filed on Dec. 23, 2020, and entitled "SYSTEM AND METHOD FOR INJECTION AND RETRACTION OF FLUID", the contents of each of which is incorporated by reference herein in its entirety.

BACKGROUND

Dialysis removes waste, toxins and excess water from the body that would be removed by a normally functioning kidney in healthy individuals.

Different types of dialysis techniques may be used as a treatment for end-stage renal disease. For example, in hemodialysis, a patient may be treated at a treatment center, such as a hospital or a dialysis clinic. In this case, the patient may attend a treatment session at the treatment center three or more times each week. During a treatment session, a hemodialysis machine may remove a patient's blood from the patient's body using a first needle at a first injection site, may filter the patient's blood, and may provide the patient's blood back into the patient's body using a second needle at a second injection site. In this way, the hemodialysis machine may perform external filtration of the patient's blood. However, attendance at multiple treatment sessions each week may be inconvenient, stressful, painful, and/or cost-prohibitive for a patient.

Another type of dialysis technique is peritoneal dialysis. In peritoneal dialysis, a patient may be surgically implanted with a catheter in the patient's peritoneal cavity. A cleansing fluid, such as dialysate solution, is injected into the patient's peritoneal cavity using the catheter. Typically, the catheter remains implanted for an extended period of time. The solution is thereafter drained from the peritoneal cavity to the original solution container or elsewhere.

Dialysate is delivered to the patient through the catheter and then filtered back out to remove toxins and waste products from the body. This process can be done manually using gravity or with the use of a cycler to fill/drain fluid. The fluid is drained into drain bags that are connected to the patient via the peritoneal dialysis tubing. Waste, toxins, and excess water enter the solution from the patient's bloodstream through the peritoneal membrane. The transfer of waste, toxins, and water from the bloodstream to the solution occurs by diffusion and osmotic pressure. Used solution is derived from the patient's abdominal cavity, waste, toxins, and water are removed from the patient, and the solution is replaced.

Peritoneal dialysis requires strict sterilization maintenance because of the high risk of peritoneal infection. The peritoneal administration of medical liquids, such as the dialysate solution, to patients is a long-established practice. Liquids, including amino acids, blood, dextrose, electrolytes, and saline are commonly administered to patients over prolonged periods. It is frequently a necessity that the sterility of the system be maintained when utilizing sterile medical liquids. If a contamination of the tubing occurs, when dialysate flows for treatment, there is a risk of microbes being introduced in the peritoneum, which can lead to infection. Prior to dialysis, it is therefore important to sterilize any ports or connectors.

Thus, there is a need for tools for sterilization of peritoneal dialysis components to allow for safe, at-home dialysis.

BRIEF SUMMARY

According to an embodiment, the present disclosure relates to a system, comprising a fluid reservoir configured to store sterilization fluid, the fluid reservoir being engageable with a plunger, and a processor operatively coupled to an actuator and configured to control the actuator to move the plunger from a first position to a second position, maintain the plunger at the second position for a predetermined period of time, and move the plunger from the second position to the first position when the predetermined period of time lapses, wherein the movement of the plunger from the first position to the second position causes at least a portion of the sterilization fluid stored in the reservoir to be expelled from the fluid reservoir and into at least one medical line via a connector, and wherein the movement of the plunger from the second position to the first position causes at least a substantial majority of the expelled sterilization fluid to be retracted via the connector back into the fluid reservoir.

According to an embodiment, the present disclosure relates to a method, comprising moving, via an actuator of a sterilization device, a plunger from a first position to a second position, the plunger being engageable with a fluid reservoir containing sterilization fluid, the moving the plunger from the first position to the second position causing at least a portion of the sterilization fluid to be expelled from the fluid reservoir and into at least one medical line via a connector, maintaining, via the actuator, the plunger at the second position for a predetermined period of time, and moving, via the actuator, the plunger from the second position to the first position when the predetermined period of time lapses, the moving the plunger from the second position to the first position causing a substantial majority of the expelled sterilization fluid to be retracted via the connector back into the fluid reservoir.

According to an embodiment, the present disclosure relates to a system, the system comprising a fluid reservoir having sterilization fluid therein, a connector in fluid communication with the fluid reservoir and with peritoneal dialysis tubing, a flow diverter fluidically-arranged between the fluid reservoir and the peritoneal dialysis tubing, and a processor configured to set the flow diverter to a first configuration configured to direct fluid flow from the fluid reservoir to a first portion of the connector coupleable to a first line of the peritoneal dialysis tubing, expel, via an actuator, at least a first portion of the sterilization fluid from the fluid reservoir and into the first line via the first portion of the connector, retract, via the actuator, a substantial majority of the expelled first portion of the sterilization fluid from the first portion of the connector, set the flow diverter to a second configuration configured to direct fluid flow from the fluid reservoir to a second portion of the connector coupleable to a second line of the peritoneal dialysis tubing, the second portion of the connector being different from the first portion of the connector, expel, via the actuator, at least a second portion of the sterilization fluid from the fluid reservoir and into the second line via the second portion of the connector, and retract, via the actuator, a substantial majority of the expelled second portion of the sterilization fluid from the second portion of the connector.

According to an embodiment, the present disclosure relates to a method, comprising setting a flow diverter to a first configuration to direct fluid flow from a fluid reservoir to a first portion of a connector coupleable to a first line of peritoneal dialysis tubing, the flow diverter being fluidically-arranged between the fluid reservoir and the peritoneal dialysis tubing, the fluid reservoir having sterilization fluid therein, expelling, via an actuator, at least a first portion of the sterilization fluid from the fluid reservoir and into the first line via the first portion of the connector, retracting, via the actuator, a substantial majority of the expelled first portion of the sterilization fluid from the first portion of the connector, setting the flow diverter to a second configuration to direct fluid flow from the fluid reservoir to a second portion of the connector coupleable to a second line of the peritoneal dialysis tubing, the second portion of the connector being different from the first portion of the connector, expelling, via the actuator, at least a second portion of the sterilization fluid from the fluid reservoir and into the second line via the second portion of the connector, and retracting, via the actuator, a substantial majority of the expelled second portion of the sterilization fluid from the second portion of the connector.

According to an embodiment, the present disclosure relates to a system, comprising a fluid reservoir having sterilization fluid therein, a connector in fluid communication with the fluid reservoir and with peritoneal dialysis tubing, a flow diverter fluidically-arranged between the fluid reservoir and the peritoneal dialysis tubing, and a processor configured to set the flow diverter to a first configuration to establish two fluid flow paths including a first fluid flow path configured to direct fluid flow from the fluid reservoir to a first portion of the connector and a second fluid flow path configured to direct fluid flow from the fluid reservoir to a second portion of the connector, the first portion of the connector and the second portion of the connector being fluidically-decoupled when the flow diverter is in the first configuration, each of the first portion of the connector and the second portion of the connector being coupled to different portions of the peritoneal dialysis tubing, expel, via an actuator, at least a portion of the sterilization fluid from the fluid reservoir and into each of the first portion of the connector and the second portion of the connector such that the portion of the sterilization fluid enters the peritoneal dialysis tubing, retract, via the actuator, a substantial majority of the expelled portion of the sterilization fluid from the first portion of the connector and the second portion of the connector, and set the flow diverter to a second configuration in which the first portion of the connector and the second portion of the connector are fluidically-coupled and peritoneal dialysis can be performed.

According to an embodiment, the present disclosure relates to a method, comprising setting, via a processor, a flow diverter to a first configuration to establish two fluid flow paths including a first fluid flow path configured to direct fluid flow from a fluid reservoir to a first portion of a connector and a second fluid path configured to direct fluid flow from the fluid reservoir to a second portion of the connector, the fluid reservoir having sterilization fluid therein, the flow diverter being fluidically-arranged between the fluid reservoir and peritoneal dialysis tubing, the connector being in fluid communication with the fluid reservoir and the peritoneal dialysis tubing, the first portion of the connector and the second portion of the connector being fluidically-decoupled when the flow diverter is in the first configuration, and each of the first portion of the connector and the second portion of the connector being coupled to different portions of the peritoneal dialysis tubing, expelling, via the processor, at least a portion of the sterilization fluid from the fluid reservoir and into each of the first portion of the connector and the second portion of the connector such that the portion of the sterilization fluid enters the peritoneal dialysis tubing, retracting, via the processor, a substantial majority of the expelled portion of the sterilization fluid from the first portion of the connector and the second portion of the connector, and setting, via the processor, the flow diverter to a second configuration in which the first portion of the connector and the second portion of the connector are fluidically-coupled and peritoneal dialysis can be performed.

BRIEF DESCRIPTION OF THE SEVERAL VIEWS OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which:

FIG. 13A, FIG. 13B, FIG. 13C, and FIG. 13D are illustrations of various aspects of a fluid flow control device, according to embodiments of the present disclosure.

FIG. 15A, FIG. 15B, and FIG. 15C are schematic diagrams of various aspects of a plunger and a fluid reservoir, according to embodiments of the present disclosure.

DETAILED DESCRIPTION

Figure 1:
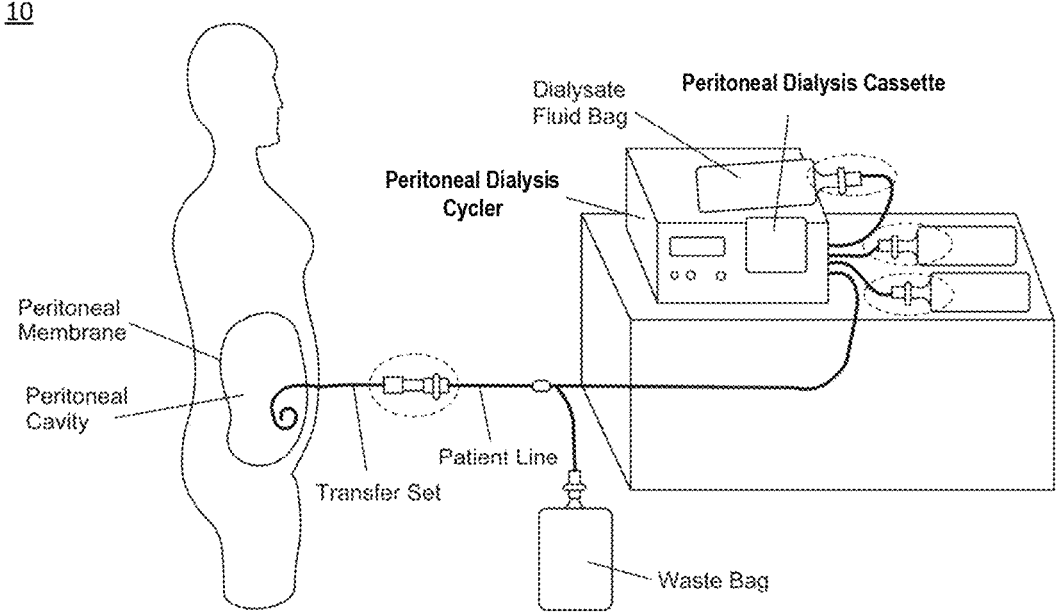
FIG. 1 is an illustration of a system for injection and retraction of fluids, according to embodiments of the present disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Peritoneal dialysis is a form of treatment for kidney failure. As described above, peritoneal dialysis may enable a patient to perform at-home dialysis, which may result in reduced costs, increased convenience, improved patient outcomes, and improved patient satisfaction relative to hemodialysis, which requires 15-20 hours a week at a treatment center. However, at present, peritoneal dialysis is underutilized as a treatment because it is associated with a high risk of infection, such as of a peritoneal membrane of the patient, which is a condition referred to as peritonitis. This may result from a patient or caregiver, who is not trained in sterilization techniques or who fails to comply with training in sterilization techniques, connecting tubing (e.g., one or more medical tubing or lines) of a peritoneal dialysis system, which may be referred to herein as peritoneal dialysis tubing, in a non-sterile environment. For example, although each of (1) an extension of the peritoneal dialysis catheter, which may be referred to herein as a transfer set and/or extension set, (2) peritoneal dialysis set tubing, which may be referred to herein, in embodiments including a cycler, as cassette tubing, and (3) dialysis fluid bag tubing, may be sterilized during manufacture, when connecting a transfer set to cassette tubing of the peritoneal dialysis system a patient may touch ends of the transfer set and the cassette tubing with bare hands. This may cause bacteria or other microbes to be disposed onto tubing surfaces. Thus, during peritoneal dialysis, dialysate may be exposed to the bacteria or other microbes during injection into a patient, thereby exposing the patient to a risk of infection. Peritonitis occurs in 30% of patients every year and requires hospitalizations in 50% of cases. It is for these reasons that peritoneal dialysis is not more commonly used.

During peritoneal dialysis, a cleansing fluid or dialysate flows through tubing (e.g., one or more medical lines or tubing) and into the abdomen (e.g., the peritoneal cavity) of the patient. The lining of the abdomen (e.g., the peritoneal membrane) acts as a filter and removes waste products from the blood. After a set period of time, the fluid with the filtered waste products flows out of the abdomen and is discarded.

The set period of time during which the cleansing fluid resides within the peritoneal cavity can be on the order of hours, sometimes between 4 hours and 6 hours. As a result, any contamination of the tubing of the peritoneal dialysis system risks patient infection.

In view of the above, the present disclosure describes an in-line connection device or connector and a sterilization fluid delivery system (e.g., including a fluid flow control device) that internally disinfects dialysis tubing at any number of connection sites in the peritoneal dialysis system (e.g., at any connection sites between one or more medical lines or tubing). As shown in FIG. 1, which is an illustration of a peritoneal dialysis system engaged with a patient, this includes the connection between the extension of the peritoneal dialysis catheter, one end of which is connected to a catheter which resides within a peritoneal cavity of the patient, and a cassette tubing (e.g., patient line), one end of which connects to dialysate fluid, as well as connections between, for instance, dialysis fluid bags and peritoneal dialysis set tubing (with or without cassette), and other associated peritoneal dialysis disposable accessories for sterile fluid flow. A non-limiting subset of possible connection points are identified in FIG. 1 by ellipses. For instance, in manual methods of peritoneal dialysis, the connection may be a connection between the extension of the peritoneal dialysis catheter and the dialysis fluid bag.

Some implementations described herein provide a sterilizable connector to enable sterilization for peritoneal dialysis. For example, a sterilizable connector may include a body with a first end to connect to a transfer set and a second end to connect to cassette tubing. Further, the sterilizable connector may include or be coupled to (e.g., permanently fixed or releasably coupled to) a sterilization fluid reservoir connected to the body and a sterilization fluid injector or fluid flow control device configured to inject the sterilization fluid into the body, the transfer set, and the cassette tubing. In this way, the sterilization fluid may sterilize surfaces of the sterilizable connector, the transfer set, and the cassette tubing, thereby reducing a likelihood of patient infection due to unsterile connections between the transfer set and the cassette tubing, as described earlier. Although some implementations described herein are described in terms of a connection to a transfer set and cassette tubing in a peritoneal dialysis system, the sterilizable connector may be used for other connections associated with a peritoneal dialysis system, for other connections in other contexts outside of a peritoneal dialysis system, and/or the like. Although some implementations described herein are described in terms of use in a peritoneal dialysis system, implementations described herein may be used in another context for which sterilized connectors are used, such as home intravenous anti-infective therapies (HIVAT), at-home chemotherapy, central venous catheters, urinary catheters, and/or the like, where similar concerns regarding infection risk and the need for sterilization exists.

Figure 2A:
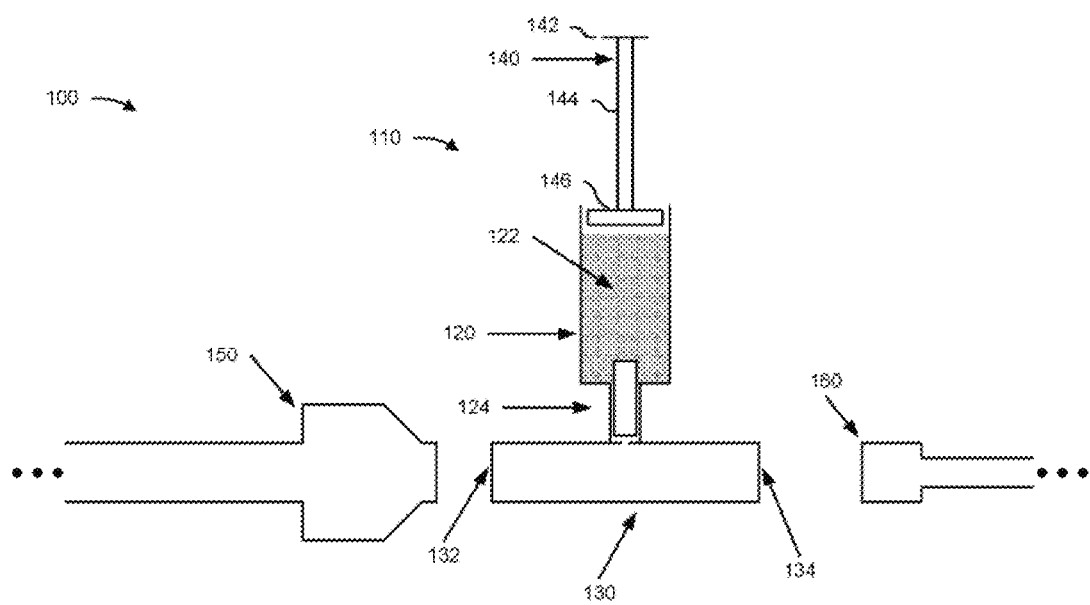
FIG. 2A, FIG. 2B, FIG. 2C, and FIG. 2D are diagrams of an overview of an example implementation of a sterilizable connector, according to embodiments of the present disclosure.

Referring again to the drawings, FIG. 2A through FIG. 2D provide schematic diagrams of an overview of an example implementation 100 described herein. As shown in FIG. 2A, example implementation 100 may include a sterilizable connector or system 110, a cassette tube 150 (e.g., which may be connected to a peritoneal dialysis cycler), and a transfer set 160 (e.g., which may be connected to a patient). Although some implementations described herein are described in terms of a sterilizable connector 110 being positioned at a connection between a cassette tube 150 and a transfer set 160, other positions are contemplated, such as at a connection between transfer set 160 and a dialysis fluid bag tube connected to a dialysis fluid bag. Other connections for which sterilization may be advantageous also are contemplated.

As further shown in FIG. 2A, sterilizable connector 110 may include a sterilization fluid reservoir 120, a connector 130, and a sterilization fluid injector or fluid flow control device 140. In some implementations, sterilization fluid reservoir 120 may be a barrel of a syringe or other injector. In some implementations, sterilization fluid reservoir 120 may include a sterilization fluid 122, that may be injected into connector 130. For example, sterilization fluid 122 can include an anti-microbial fluid for sterilizing surfaces of connector 130, cassette tube 150, transfer set 160, and/or the like, thereby reducing a risk of patient infection. In some implementations, sterilization fluid reservoir 120 may be sized to hold a particular amount of sterilization fluid 122, such as about 1 milliliter (ml), about 5 ml, about 10 ml, about 20 ml, about 50 ml, including all ranges and values therebetween. In some implementations, sterilization fluid reservoir 120 may be sized to hold an amount of sterilization fluid 122 between about 0.05 ml and about 50 ml, between about 1 ml and about 50 ml, between about 5 ml and about 50 ml, between about 10 ml and about 50 ml, and between about 20 ml and about 50 ml. In some implementations, sterilization fluid reservoir 120 and/or connector 130 may include a valve 124. For example, valve 124 may open to enable injection of sterilization fluid 122, removal of sterilization fluid 122, and/or the like.

In some implementations, valve 124 may enable disconnection of sterilization fluid reservoir 120 and sterilization fluid injector 140. For example, after injection of sterilization fluid 122, as described in more detail below, sterilization fluid reservoir 120 and sterilization fluid injector 140 may be detached from connector 130, and valve 124 may close to seal an opening of sterilization fluid reservoir 120 or connector 130. In this way, by detaching a portion of sterilizable connector 110 such as, for example, sterilization fluid reservoir 120 and/or sterilization fluid injector 140, a likelihood of sterilizable connector 110 interfering with tubes (e.g., medical lines or tubing) of the peritoneal dialysis system and/or causing patient discomfort is reduced. Moreover, sterilization fluid reservoir 120 may be replaceable by attaching new sterilization fluid reservoirs 120 each time a patient is to perform peritoneal dialysis, while connector 130 remains in-line with the peritoneal dialysis tubing, thereby reducing an inconvenience and/or difficulty of use associated with connecting connector 130.

In some implementations, sterilization fluid reservoir 120 may include a restrictor mechanism or dwell mechanism. For example, sterilization fluid reservoir 120 may include a rubber slider, an angled flap, a latched lever, and/or the like to control a depth to which sterilization fluid injector 140 may be inserted into sterilization fluid reservoir 120, a height to which sterilization fluid injector 140 may be removed from sterilization fluid reservoir 120, a dwell time (e.g., an amount of time) for sterilization fluid 122 to remain in connector 130 after being injected into the connector 130, a rate at which sterilization fluid injector 140 injects and/or removes sterilization fluid 122, and/or the like. In some implementations, sterilizable connector 110 may include at least one indicator to indicate when flow of sterilization fluid into sterilization connector 110 has initiated, when the dwell time is elapsed, and/or when the sterilization fluid has been retracted from sterilization connector 110. The at least one indicator may include a visual indicator, a light, a display, an audio device, or other indicator device. Additionally, or alternatively, a configured chemical reaction may be used to indicate the presence/absence of sterilization fluid within sterilization connector 110 and/or when the dwell time is elapsed.

In some implementations, connector 130 may be a body or housing disposed between cassette tube 150 and transfer set 160. The connector 130 can define one or more passages or channels for establishing fluid flow between cassette tube 150 and transfer set 160. For example, a first end 132 of connector 130 may receive and connect to cassette tube 150 and a second end 134 of connector 130 may receive and connect to transfer set 160, as described in more detail herein. In some implementations, connector 130 may form or include a tube connecting cassette tube 150 and transfer set 160.

In some implementations, connector 130 may include a body opening or port to receive sterilization fluid 122 (e.g., from fluid reservoir 120). The body opening or port can be configured to releasably couple to the fluid reservoir 120. In some implementations, connector 130 may include one or more other openings or ports. For example, connector 130 may include another opening to receive one or more sterilization fluid reservoirs, wash reservoirs, or other fluid sources. In the case of a wash reservoir, wash fluid different from the sterilization fluid 122 may be injected into connector 130 after injecting the sterilization fluid 122, and the wash fluid may displace the sterilization fluid 122, thereby removing sterilization fluid 122 from connector 130, from cassette tube 150, from transfer set 160, and/or the like. In this way, a likelihood of sterilization fluid 122 being inserted into a patient is reduced. In some embodiments, multiple sterilization fluid reservoirs can be coupled to one or more openings of the connector 130, e.g., to enable multiple sterilization cycles or to sterilize different portions of the peritoneal dialysis tubing (e.g., the transfer set separate from the cassette tube).

In some implementations, sterilization fluid injector 140 may include a plunger flange 142, a plunger 144, and a plunger seal 146. For example, sterilization fluid injector 140 may form a plunger that may be inserted into and removed from sterilization fluid reservoir 120 to inject sterilization fluid 122 into connector 130 and/or remove sterilization fluid 122 from connector 130. In some implementations, sterilization fluid injector 140 may include a dampener, which may restrict a rate at which sterilization fluid 122 is injected into connector 130, a rate at which sterilization fluid 122 is removed from connector 130, and/or the like. In some implementations, the dampener may be a spring to automatically raise sterilization fluid injector 140 to remove sterilization fluid 122 from connector 130. Alternatively or additionally, in some implementations, sterilization fluid injector 140 may include a processor and/or processing circuitry for controlling injection, retraction, and/or dwell time, as further described in later embodiments. In some implementations, sterilization fluid injector 140 may include a particular type of actuator or button mechanism, e.g., that may form at least a portion of plunger flange 142 or be coupled to plunger flange 142. For example, sterilization fluid injector 140 may include an actuator such as a pull button, a push button, a squeeze button, a twist mechanism, and/or the like. In some implementations, the actuator or button mechanism may be a reusable mechanism and at least a portion of sterilization fluid injector 140 may be a disposable mechanism (e.g., sterilization fluid reservoir 120) to maintain sterilization. In some embodiments, sterilization fluid injector 140 may include a drive mechanism, controller or processor, power source, etc., for controlling injection and/or retraction of sterilization fluid 122 from the connector 130. Further details of such an embodiment are described with reference to FIG. 5 below.

Figure 2B:
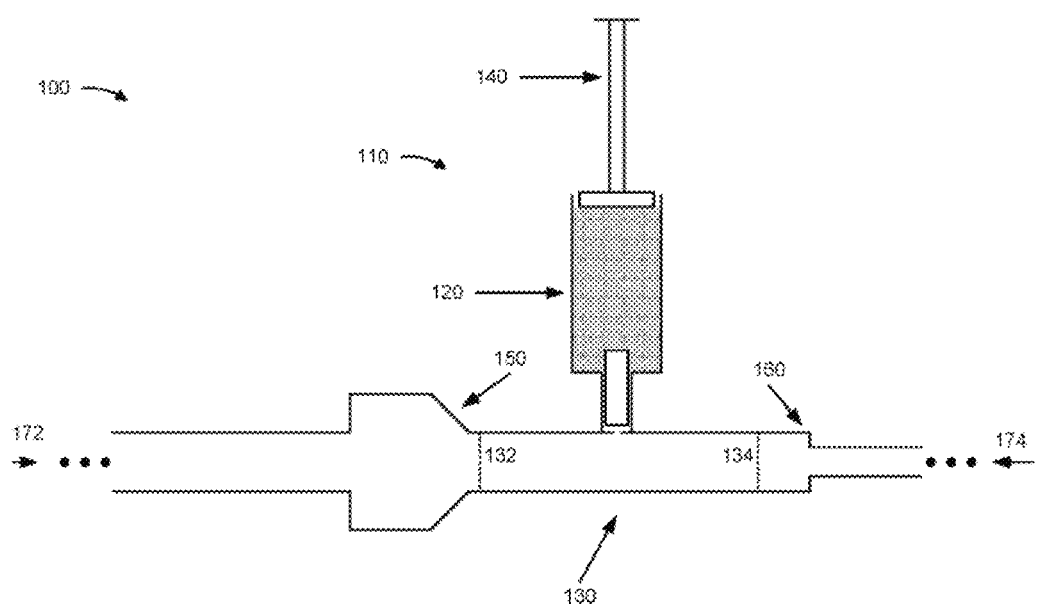

As shown in FIG. 2B, and by reference number 172, first end 132 of sterilizable connector 110 may receive cassette tube 150. For example, a patient may attach an end of cassette tube 150 to first end 132 and may seal a connection. In this case, first end 132 and/or cassette tube 150 may include an attachment portion, such as a cap, a clamp, a Luer lock, a screw end, and/or the like to seal the connection. As shown by reference number 174, second end 134 of sterilizable connector 110 may receive transfer set 160. For example, a patient may attach an end of transfer set 160 to second end 134 and may seal a connection. In this case, second end 134 and/or transfer set 160 may include an attachment portion, such as a cap, a clamp, a Luer Lock, a screw end, and/or the like to seal the connection. In some implementations, sterilizable connector 110 may be connected in another context. For example, sterilizable connector 110 may receive, at first end 132, a first tube or line (e.g., associated with a medical device or patient) and, at second end 134, a second tube or line (e.g., associated with a medical device or patient) to enable sterilization of a connection between the first tube and the second tube. In some implementations, sterilizable connector 110 may be connected to the medical device or patient via one or more other intervening components, such as one or more valves, one or more other connectors, one or more other tubes, and/or the like. For example, although the first tube is described as connecting to, for example, the medical device, the first tube may connect directly to the medical device, indirectly to the medical device (e.g., via one or more intervening components), and/or the like.

Figure 2C:
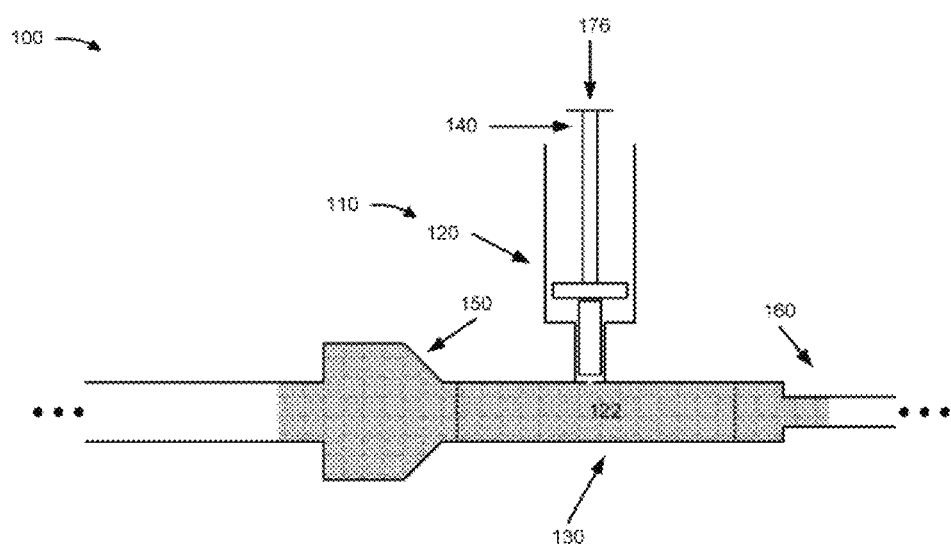

As shown in FIG. 2C, and by reference number 176, sterilization fluid injector 140 may inject sterilization fluid 122 into connector 130, cassette tube 150, transfer set 160, and/or the like. For example, a patient may depress a plunger of sterilization fluid injector 140 to inject sterilization fluid 122. In this case, sterilization fluid 122 may remain in, for example, connector 130, cassette tube 150, transfer set 160, other medical tubing, and/or the like for a predetermined period of time (e.g., dwell time) to enable sterilization of surfaces of connector 130, cassette tube 150, transfer set 160, other medical tubing, and/or the like. In this way, sterilizable connector 110 reduces a likelihood of patient infection by enabling sterilization of a connection between cassette tube 150 and transfer set 160. In some embodiments, sterilization fluid 122 can be delivered into the peritoneal dialysis tubing such that the sterilization fluid 122 extends at least a predetermined distance into the tubing (e.g., cassette tube 150, transfer set 160, other medical tubing). In some embodiments, this predetermined distance can be about 1 mm, about 5 mm, about 10 mm, 50 mm, about 1 cm, about 2 cm, about 3 cm, about 5 cm, about 10 cm, including all values and ranges therebetween.

Figure 2D:
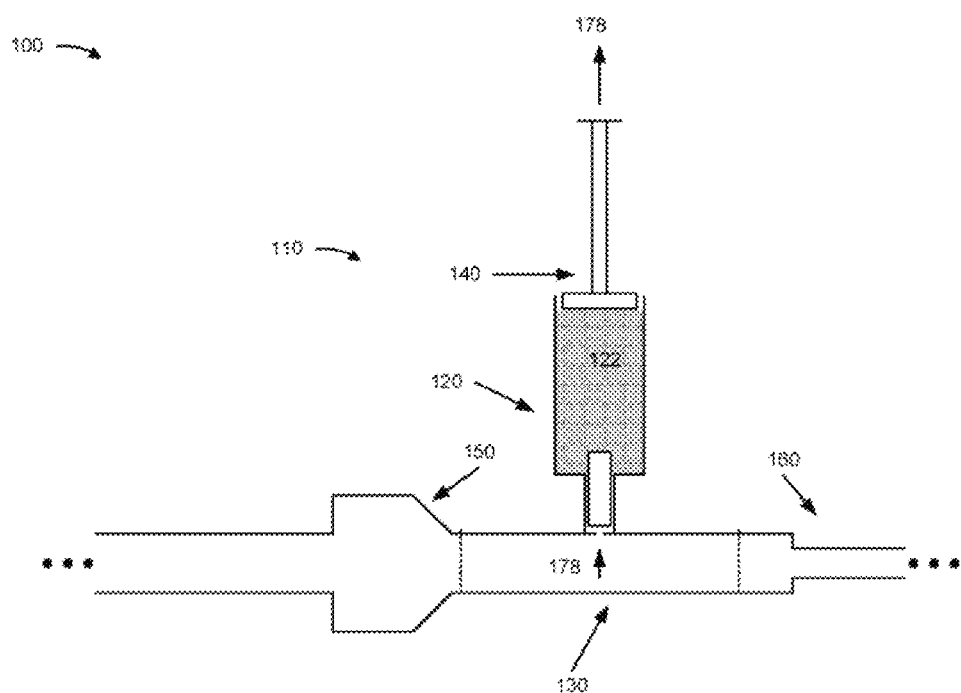

As shown in FIG. 2D, and by reference number 178, sterilization fluid injector 140 may remove or retract sterilization fluid 122 from connector 130, cassette tube 150, transfer set 160, and/or the like. For example, a patient may raise a plunger or other injecting element of sterilization fluid injector 140 to remove sterilization fluid 122. After the removal of the sterilization fluid 122, the patient may detach sterilization fluid reservoir 120, sterilization fluid injector 140, and/or the like, as described above. In some implementations, a sterilization fluid retractor may be separate from sterilization fluid injector 140. For example, another plunger, pump, vacuum, etc. may retract sterilization fluid 122 from connector 130. Additionally, or alternatively, a wash fluid reservoir and a wash fluid injector may inject wash fluid into connector 130 to displace sterilization fluid 122, thereby retracting sterilization fluid 122. Additionally, or alternatively, a peritoneal dialysis cycler attached to cassette tube 150 may retract sterilization fluid 122. Additionally, or alternatively, as shown, sterilization fluid injector 140 may be the sterilization fluid retractor.

In some implementations, after a retraction of sterilization fluid 122, peritoneal dialysis may be performed. For example, in accordance with a configuration of sealing valve 124 (e.g., with sealing valve 124 being closed after retraction of the sterilization fluid 122), dialysate fluid may be injected into a patient by a peritoneal dialysis cycler or other dialysate fluid source via cassette tube 150, connector 130, transfer set 160, a surgically implanted catheter connected to transfer set 160, other medical tubing or line(s), and/or the like. Similarly, the peritoneal dialysis cycler, a pump mechanism, or gravity may cause waste fluid to be removed from a patient via cassette tube 150, connector 130, transfer set 160, and/or the like. In this way, peritoneal dialysis may be performed using sterilizable connector 110 with a reduced risk of patient infection.

As indicated above, FIG. 2A through FIG. 2D are provided merely as an example. Other examples may differ from what is described with reference to FIG. 2A through FIG. 2D.

Figure 3:
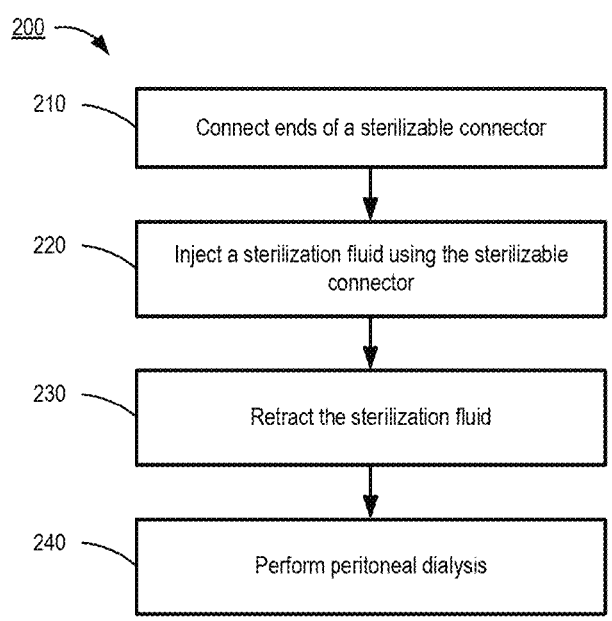
FIG. 3 is a flow diagram of an example process for sterilization for peritoneal dialysis, according to embodiments of the present disclosure.

FIG. 3 is a flow diagram of an example process of sterilization for peritoneal dialysis. In some implementations, one or more process blocks 210-240 of process 200 of FIG. 3 may be performed by a patient or caregiver using a sterilizable connector. In some implementations, one or more process blocks of process 200 of FIG. 3 may be automated. For example, process blocks 220 and 230 may be automated such that a fluid flow control device (e.g., fluid flow control device 500, as described below), which may include a sterilization fluid injector and/or retractor, a controller, and/or a drive mechanism, controls injection and retraction of the sterilization fluid to and from the connector. It follows, then, that the methods described below may be manually implemented by a patient or caregiver or, in the event of automation, at least partially by a processor or processing circuitry of a fluid flow control device in conjunction with computer-readable instructions. The processor or processing circuitry may be implemented in coordination with a user interface (e.g., including a control switch or other control mechanism) allowing the patient or caregiver to administer and/or proctor process 200.

In embodiments, a fluid reservoir as described herein may include or be implemented as a syringe, a bulb, a bag, a cartridge, or other suitable dispensing mechanism. In embodiments, the syringe may include a plunger and a barrel, the plunger and the barrel together defining a sterilization fluid reservoir storing sterilization fluid.

As shown in FIG. 3, process 200 may include connecting ends of a sterilizable connector, at 210. For example, the patient may connect the ends of the sterilizable connector, as described above. In some implementations, the patient may attach a cassette tube of a peritoneal dialysis cycler to a first opening of a body portion of a sterilizable connector. In some implementations, the patient may attach a transfer set to a second opening of the body portion of the sterilizable connector. In some implementations, ends of the sterilizable connector may be connected to, for example, the cassette tube and the transfer set without patient interaction. For example, a medical robotics device may automatically connect the cassette tube and the transfer set to the sterilizable connector. In some implementations, an end of the sterilizable connector may be connected to a dialysis fluid bag via a tube.

As further shown in FIG. 3, process 200 may include injecting a sterilization fluid using the sterilizable connector, as 220. For example, the patient may use the sterilizable connector to inject the sterilization fluid, as described above. In some implementations, the sterilization fluid may be injected at a rate of between about 0.01 mL/second (mL/sec) and about 2.5 mL/sec, between about 0.05 mL/sec and about 1 mL/sec, between about 0.1 mL/sec and about 0.75 mL/sec, between about 0.15 mL/sec and about 0.6 mL/sec, between about 0.2 mL/sec and about 0.4 mL/sec, between 0.25 mL/sec and about 0.3 mL/sec. In some implementations, the sterilization fluid may be injected at a rate of about 0.3 mL/sec. In some implementations, the patient may inject the sterilization fluid into a third opening of a body portion of the sterilizable connector, such that the sterilization fluid is in contact with at least a portion of the cassette tube, at least a portion of the transfer set, and at least a portion of the body portion. In some implementations, a medical robotics device may automatically inject the sterilization fluid into the body portion of the sterilizable connector. In some implementations, the sterilizable connector may be positioned between and/or used to sterilize one or more other interconnection points of adjacent components in a fluid transfer path, such as the fluid transfer path described herein, another fluid transfer path, and/or the like.

As further shown in FIG. 3, process 200 may include retracting the sterilization fluid, at 230. For example, the patient may use the sterilizable connector to retract the sterilization fluid, as described above. In some implementations, the patient may use the sterilizable connector to retract the sterilization fluid after a predetermined period of time has lapsed. In embodiments, the predetermined period of time may be between about 0.5 seconds and about 120 seconds, between about 1 second and about 60 seconds, between about 2 seconds and about 30 seconds, between about 3 seconds and about 15 seconds, between about 4 seconds about 7 seconds, and/or between about 5 seconds and about 6 seconds. In embodiments, the predetermined period of time may be at least about 1 second, at least about 2 seconds, at least about 3 seconds, at least about 4 seconds, at least about 5 seconds, at least about 6 seconds, at least about 7 seconds, at least about 8 seconds, at least about 9 seconds, and/or at least about 10 seconds. In embodiments, the predetermined period of time may be about 1 second, about 2 seconds, about 3 seconds, about 4 seconds, about 5 seconds, about 6 seconds, about 7 seconds, about 8 seconds, about 9 seconds, and/or about 10 seconds. In embodiments, the predetermined period of time may be about 5 seconds. In embodiments, the predetermined period of time may be about 30 seconds. The predetermined period of time is selected as one that allows for sterilization of the inside of the connector and the peritoneal dialysis tubing while minimizing the time required to achieve that result.

In some implementations, the patient may use the sterilizable connector to retract the sterilization fluid, to displace or dilute the sterilization fluid with a wash fluid, and/or the like. In some implementations, the sterilization fluid may be retracted at a rate of between about 0.01 mL/second (mL/sec) and about 2.5 mL/sec, between about 0.05 mL/sec and about 1 mL/sec, between about 0.1 mL/sec and about 0.75 mL/sec, between about 0.15 mL/sec and about 0.6 mL/sec, between about 0.2 mL/sec and about 0.4 mL/sec, between 0.25 mL/sec and about 0.3 mL/sec. In some implementations, the sterilization fluid may be retracted at a rate of about 0.3 mL/sec. In some implementations, the patient may close a closeable valve of the sterilizable connector to seal the third opening of the body portion of the sterilizable connector and to enable detachment of a portion of the sterilizable connector.

In some implementations, the sterilization fluid may be one of a variety of sterilization agents having one of a variety of compositions. In embodiments, the sterilization fluid may be based on ethylenediaminetetraacetic acid (EDTA), sodium dodecyl sulfate (SDS), formaldehyde, hypochlorite, calcium hypochlorite, sodium hypochlorite, peroxide, hydrogen peroxide, sodium percarbonate, sodium perborate ethanol, methanol, polyhexamethylene biguanide, povidone-iodine, chlorhexidine, isopropyl alcohol, water, and the like. In embodiments, the sterilization fluid may be sodium hypochlorite having a concentration between about 0.0001 Molar (M) and about 100 M sodium hypochlorite, between about 0.0005 M and about 10 M sodium hypochlorite, between about 0.001 M and about 1 M sodium hypochlorite, and/or between about 0.1 M and about 0.5 M sodium hypochlorite. In an example, the sterilization fluid is about 0.0013 M sodium hypochlorite. In another example, the sterilization fluid is about 0.015 M sodium hypochlorite (0.11% sodium hypochlorite). In another example, the sterilization fluid is about 0.074 M sodium hypochlorite (0.55% sodium hypochlorite).

Injection and retraction of the sterilization fluid is enabled by, in part, the ability to move the sterilization fluid at a rate at which surface tension within the fluid is not overcome by forces which may disperse the expelled sterilization fluid into the periphery of the peritoneal dialysis tubing. If this happens, the patient can be exposed, unsafely, directly to the sterilization fluid. For instance, a rate of fluid retraction that is too fast may result in collapse of the expelled sterilization fluid and loss of at least a portion of the sterilization fluid to peripheral regions of the peritoneal dialysis tubing or even the patient. Similarly, residual sterilization fluid that is not contained in the retracted sterilization fluid upon completion of retraction may increase the risk of unintended sterilization or other complications. Conversely, a rate of fluid retraction that is too slow may inconvenience the patient and take too long. Accordingly, the rate at which at least a substantial portion of the expelled sterilization fluid is retracted is selected to ensure safety while minimizing the time required to perform the sterilization. The same concerns and constraints apply to selection of the rate at which the sterilization fluid is injected. In some embodiments, the rate of injection and the rate of retraction are the same rate. In other embodiments, the rate of injection and the rate of retraction are different rates. In some embodiments, the rate of injection and/or the rate of retraction remain constant during a time period during which the sterilization fluid is flowed. In certain other embodiments, an acceleration or deceleration may be applied, wherein the rate of injection and/or the rate of retraction dynamically change and adjust during a time period during which the sterilization fluid is flowed.

In embodiments, a volume of sterilization fluid delivered to the connector is based on a degree of surface coverage of the peritoneal dialysis tubing upon injection of the sterilization fluid. For instance, considered as a distance from an end of the connector along a linear length of peritoneal dialysis tubing, the preset volume of sterilization fluid injected may be such that the sterilization fluid contacts at least about 0.5 mm of the peritoneal dialysis tubing, at least about 1.0 mm of the peritoneal dialysis tubing, at least about 1.5 mm of the peritoneal dialysis tubing, at least about 2.0 mm of the peritoneal dialysis tubing, at least about 2.5 mm of the peritoneal dialysis tubing, at least about 5.0 mm of the peritoneal dialysis tubing, and at least about 10.0 mm of the peritoneal dialysis tubing, and/or at least about 20.0 mm of the peritoneal dialysis tubing, including all ranges and value therebetween.

Returning to FIG. 3, process 200 may include performing peritoneal dialysis, at 240. For example, the patient may perform peritoneal dialysis, as described above. In some implementations, the patient may use a peritoneal dialysis cycler of a peritoneal dialysis cycler system (e.g., that includes the peritoneal dialysis cycler, one or more tubes, and/or the like) to perform peritoneal dialysis via a fluid transfer path that includes the cassette tube connected to a peritoneal dialysis cassette, the body portion of the sterilizable connector, the transfer set, other medical tubing, and/or the like. In some implementations, the patient may use a manual exchange via gravity to perform peritoneal dialysis via a fluid transfer path that includes dialysis fluid bag tubing connected to a dialysis fluid bag, sterilizable connector, transfer set, other medical tubing, and the like. Additionally, or alternatively, the fluid transfer path may include a dialysis fluid bag tube connected to a dialysis fluid bag.

Process 200 may include additional implementations, such as any single implementation or any combination of implementations described above and/or in connection with one or more other processes described elsewhere herein.

Although FIG. 3 shows example blocks of process 200, in some implementations, process 200 may include additional blocks, fewer blocks, different blocks, or differently arranged blocks than those depicted in FIG. 3. Additionally, or alternatively, two or more of the blocks of process 200 may be performed in parallel.

As noted above, process 200 may be an automated process, in certain embodiments. To this end, the fluid flow control device may include an electrical control system having a processor, or processing circuitry, configured to automatically perform process 200. In some embodiments, the electrical control system may be operatively coupled to an actuation system configured to interface with a dispensing element to control injection and retraction of sterilization fluid from a connector and/or one or more medical tubes.

Figure 4:
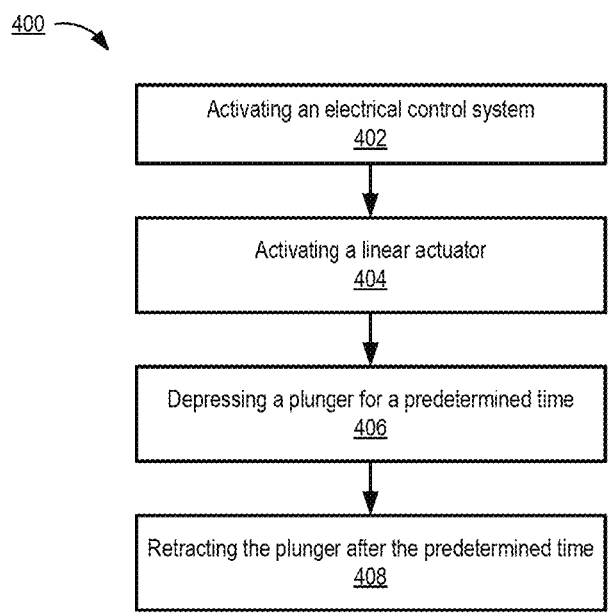
FIG. 4 is a flow diagram illustrating a method for controlling injection and retraction of a fluid, according to embodiments of the present disclosure.

Described visually, FIG. 4 is a flowchart illustrating a method of automatically performing the dialysis tubing sterilization, wherein the system includes a syringe (with a plunger and a barrel that define a sterilization fluid reservoir), according to an embodiment of the present disclosure. As shown in FIG. 4, the method 400 includes 402, which comprises activating an electrical control system through activation of a switch. At 404, an actuator (e.g., a linear actuator) that is controlled by the electrical control system is activated. In some examples, a motor that interfaces with the actuator may be activated. At 406, the actuator is utilized to depress a plunger of a fluid reservoir, thus moving the plunger from a first position to a second position. Depression of the plunger may cause fluid to be expelled from a fluid reservoir (e.g., defined by the syringe plunger and the syringe barrel) into a connector (i.e., injected into the connector). The actuator may depress the plunger at a predetermined injection rate. The predetermined injection rate may be one as described with reference to FIG. 3, such as between about 0.1 mL/sec and about 0.5 mL/sec, including about 0.3 mL/sec. At 408, the plunger is retracted after a predetermined period of time, thus moving the plunger from the second position to the first position, the fluid (or a substantial majority thereof) being retracted out of the connector and into the fluid reservoir. In embodiments, the plunger may be retracted from the second position to at least the first position, the first position being a known distance from the second position. In embodiments, the plunger may be retracted from the second position to a third position, the third position being a further distance from the second position than the known distance between the first position from the second position or a shorter distance from the second position than the known distance between the first position and the second position, movement of the plunger to the third position ensuring a minimization of sterilization fluid remaining in the connector. The predetermined period of time may be a time determined to achieve a certain sterilization effect, which, in certain embodiments, can be particular to a given sterilization fluid, the materials the connector and tubing are fabricated of, the type of contamination (i.e., bacteria, virus), and the like. The predetermined period of time may be one as described with reference to FIG. 3, such as between about 1 second and about 10 seconds, including about 5 seconds. The actuator may retract the plunger at a predetermined retraction rate. The predetermined retraction rate may be one as described with reference to FIG. 3, such as between about 0.1 mL/sec and about 0.5 mL/sec, including about 0.3 mL/sec. With the plunger in the first position, the plunger may be automatically disengaged from a plunger housing of the fluid flow control device. Similarly, the fluid reservoir (i.e., syringe barrel) may automatically be disengaged from a fluid reservoir housing of the fluid flow control device.

While not depicted in FIG. 4, it can be appreciated that peritoneal dialysis can be performed after retracting the plunger and removing the sterilization fluid (i.e., after 408).

Figure 5:
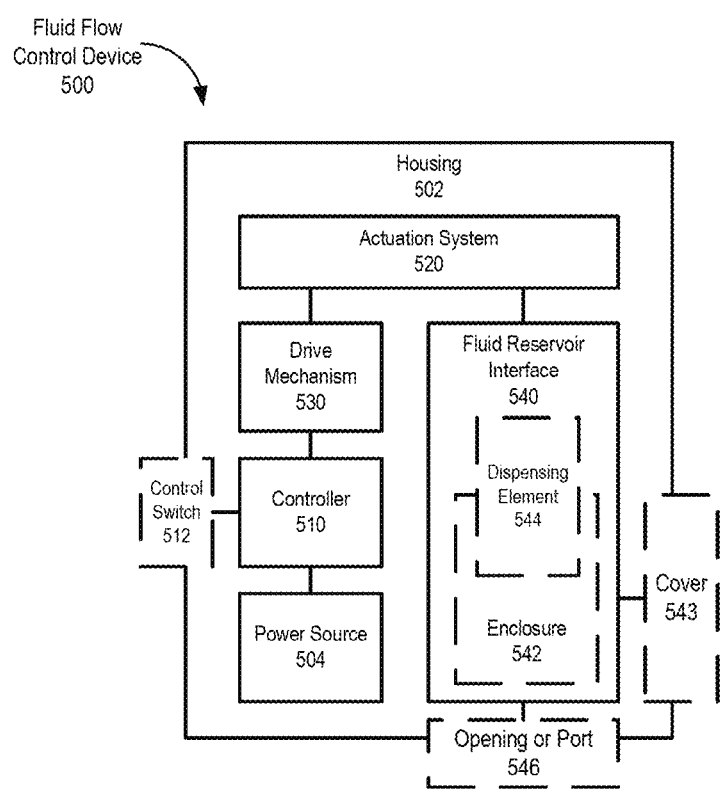
FIG. 5 is a schematic diagram of a fluid flow control device, according to embodiments of the present disclosure.

An electronic fluid flow control device or injector is now discussed in detail with reference to FIG. 5. The fluid flow control device 500 can include components that are structurally and/or functionally similar to like components of other devices described herein, including, for example, sterilizable connectors (e.g., sterilizable connector 110), injectors, etc. In an embodiment, fluid flow control device 500 may include a housing 502. The housing 502 may include an actuation system 520 operatively coupled to a drive mechanism 530 and a fluid reservoir interface 540. The drive mechanism 530 may be operatively coupled to a controller 510. A power source 504 may be connected to any module or component within the housing 502. For instance, the power source 504 may be directly connected to the controller 510, to the drive mechanism 530, to the actuation system 520, and/or to the fluid reservoir interface 540. In one instance, the power source 504 is directly connected to the controller 510, which subsequently provides power to the drive mechanism 530, which is operatively coupled to the fluid reservoir interface 540 via the actuation system 520. In an embodiment, the power source 504 may be a linear regulated power supply, a switching regulated power supply, a battery power source, and the like.

The fluid reservoir interface 540 can be an interface for receiving, engaging, or otherwise interacting with a fluid reservoir. In some embodiments, the fluid reservoir interface 540 can include or define an enclosure 542. In some embodiments, the fluid flow control device 500 can include a cover 543 that is configured to transition between first and second configurations (e.g., open and closed configurations) to provide access to the fluid reservoir interface 540 (e.g., enclosure 542). The fluid reservoir interface 540 can be substantially within the housing 502, or at least components thereof can be enclosed by the housing 502 and/or the cover 543. In some embodiments, the fluid reservoir interface 540 can include or be operatively coupled to an opening or port 546 to allow for dispensing, or expelling and retracting, of sterilization fluid (e.g., from a fluid reservoir) therethrough.

In an embodiment, the controller 510 may be activated or deactivated by user interaction with a control switch 512. The control switch 512 is optional, but when present, can be situated on or within a wall of the housing. The control switch 512 may be a pushbutton switch, a pressure switch, a temperature switch, a limit switch, a joystick switch, a toggle switch, a rotary switch, a translating switch or slider, a touchscreen interface, and the like.

In an embodiment, the controller 510 may be wirelessly activated and deactivated (not shown) by user interaction with a compute device, such as, for example, a mobile device, portable computer, or desktop. In such embodiments, the controller 510 can include or be operatively coupled to a communication interface, such as, for example, a wireless or wired communication interface. The controller 510 may be a sub-processor that receives instruction from a mobile device or other compute device having a processor that substantially controls execution of the processes and methods of the fluid flow control device, as described herein. Communication between the controller 510 and such compute device may be wireless or wired. In the case of wireless communication, the wireless communication can be one of Bluetooth®, Wi-Fi, microwave technology, radio wave technology, infrared communication, satellite communication, and the like.

The processes and logic flows described herein, whether performed at the controller 510 of the fluid flow control device 500, or performed remotely at a compute device, can be performed by one or more programmable computers executing one or more computer programs to perform one or more functions of the fluid flow control device. The processes and logic flows can also be performed by, and can also be implemented as, special purpose logic circuitry, e.g., an FPGA (field programmable gate array) or an ASIC (application-specific integrated circuit).

Compute devices, which may be generally referred to herein as a compute device or controller, suitable for the execution of a computer program include, by way of example, general or special purpose microprocessors or both, or any other kind of central processing unit. Generally, a central processing unit will receive instructions and data from a read-only memory or a random access memory or both. Elements of a compute device include a central processing unit for performing or executing instructions and one or more memory devices for storing instructions and data. Generally, a compute device can also include, or be operatively coupled to receive data from or transfer data to, or both, one or more mass storage devices for storing data, e.g., magnetic, magneto-optical disks, or optical disks. However, a compute device need not have such devices. Moreover, a compute device can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

In an embodiment, the actuation system 520 may include one or more actuators. In embodiments, the actuator may include one or more of a linear actuator, a rotary actuator, hydraulic actuator, pneumatic actuator, electric actuator, thermal and magnetic actuator, mechanical actuator, supercoiled polymer actuators, a diaphragm-assisted actuator, and the like.

In an embodiment, the drive mechanism 530 may include one or more of a motor, a geared mechanism, a piezoelectric mechanism, a magnetic mechanism, and the like, and may be configured to transmit, mechanically, instructions from the controller 510 to the actuation system 520. The drive mechanism 530 can be configured to drive movement of the actuation system 520. For example, the drive mechanism 530 can be an electric motor that, in response to an electric signal from the controller, can be configured to activate to drive movement of the actuation system 520 (including one or more actuators) for injecting and/or retracting sterilization fluid.

Optionally, the fluid flow control device can include a dispensing element 544 that is configured to be disposed, at least partially, within an enclosure 542. The dispensing element 544 can be configured to be actuated, e.g., via actuation system 520, to dispense sterilization fluid out of a fluid reservoir. In some embodiments, the dispensing element 544 may include a syringe, an elastomer (e.g., balloon), a diaphragm, a flexible tubing that may be compressed in a peristaltic manner, and the like. In embodiments, the dispensing element 544 may be integrated with the actuation system and may include a pneumatic dispenser, a syringe pump, an elastomeric pump, and a peristaltic pump, among others. In an example embodiment, the dispensing element 544 can be implemented as one or more walls, platforms, diaphragms, or balloons that can be moved to reduce an area of the enclosure 542 to drive sterilization fluid out of a fluid reservoir positioned in the enclosure.

Figure 6:
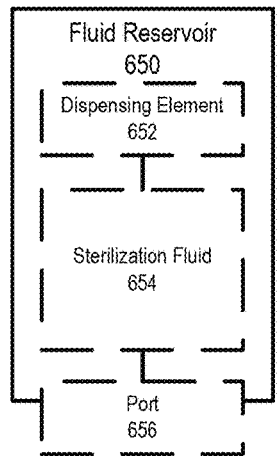
FIG. 6 is a schematic diagram of a fluid reservoir of a fluid flow control device, according to embodiments of the present disclosure.

In some embodiments, the fluid flow control device 500 may not include a dispensing element. Instead, the dispensing element can be included in a fluid reservoir that can be removably insertable or couplable to the fluid flow control device. With reference now to FIG. 6, a schematic of a fluid reservoir 650 is described. The fluid reservoir 650 can be configured to contain sterilization fluid 654. In some embodiments, the fluid reservoir 650 can include or be implemented as a syringe, cartridge, bulb, bag, or the like. In some embodiments, the fluid reservoir 650 can optionally include a dispensing element 652 and/or a port 656. The fluid reservoir 650 can be configured to be received within and/or engaged to a fluid reservoir interface of a fluid flow control device, such as, for example, fluid flow control device 500. When the fluid reservoir is received within and/or engaged to the fluid reservoir interface, the port 656 can be configured to engage with an opening or port of the fluid flow control device (e.g., opening or port 546 of the housing 502 of the fluid flow control device 500 of FIG. 5) to allow for expulsion and retraction of the sterilization fluid 654.

In some embodiments, the fluid reservoir 650 may not include a port 656. For example, the fluid reservoir 650 may be implemented as a bag that contains the sterilization fluid 654. In such embodiments, the fluid reservoir 650 can include an opening that can be aligned with an opening or port of the fluid flow control device when the fluid reservoir 650 is positioned within the fluid flow control device. Alternatively, the fluid reservoir 650 can include a frangible or breakable portion that can be punctured or broken before or while the fluid reservoir 650 is being positioned in the fluid flow control device. For example, the fluid flow control device can include a needle or other puncturing device that can puncture through the frangible section of the bag to allow sterilization fluid 654 within the bag to be injected out of the fluid reservoir 650 and into a connector coupled to the fluid reservoir and/or fluid flow control device.

The sterilization fluid 654 within the fluid reservoir 650 may be a composition, similar to that described with respect to FIG. 3. The fluid reservoir 650 may include, as described above, one of a syringe, an elastomer, a flexible tubing, and the like. For instance, the fluid reservoir 650 may be defined by a sealing end of a plunger of the syringe and a barrel of the syringe, with the sterilization fluid 654 residing therein. During implementation of the processes described herein, the fluid reservoir 650 may be operatively coupled to the actuation system (e.g., a barrel or other dispensing element 652 can be operatively coupled to the actuation system of FIG. 5) in order to effectuate expulsion and retraction of the sterilization fluid 654.

As described above, sterilization fluid expelled from the fluid reservoir 650, as controlled by the fluid flow control device, flows into a connector that interfaces with peritoneal dialysis tubing or other components (e.g., one or more medical tubes, connectors, lines, etc.). It is via the connector that sterilization of the peritoneal dialysis tubing, on either side of the connector, is realized.

Figure 7:
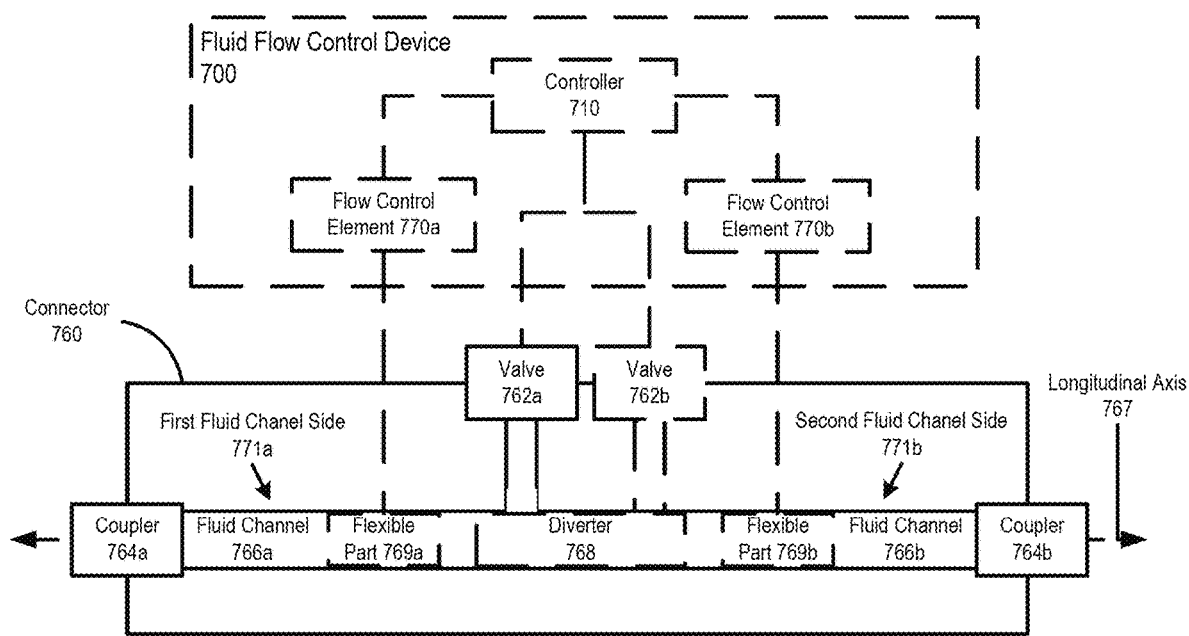
FIG. 7 is a schematic diagram of an aspect of a fluid flow control device coupled with a connector and dialysis tubing, according to embodiments of the present disclosure.

Accordingly, FIG. 7 provides a description of a connector 760 and its optional interfacing with the fluid flow control device. In some embodiments, the connector 760 can be configured to control (or facilitate control of) directionality and/or timing of fluid flow through the connector 760. The connector 760 can be structurally and/or functionally similar to other connectors described herein, including, for example, connector 130.

In embodiments, the connector 760 may be a tubular or elongate structure having, on a first end and on a second end, a first coupler 764a and a second coupler 764b, respectively. The first coupler 764a and the second coupler 764b allow the connector to be fitted to or coupled to the peritoneal dialysis tubing (e.g., the transfer set and the cassette tubing, or other tubing or lines in the peritoneal dialysis tubing) to allow fluid flow therethrough. The first coupler 764a and the second coupler 764b may include one or more coupling mechanisms, including Luer connectors, barbed connectors, stepped connectors, bayonet fittings, compression fittings, funnel connectors, flare connectors, quick disconnect connectors, straight connectors, friction-fit connectors, or the like. The tubular structure between the first coupler 764a and the second coupler 764b may include a first fluid channel 766a (or a first portion 766a of a fluid channel 766) and a second fluid channel 766b (or a second portion 766b of the fluid channel 766), though the fluid channel may also be referred to, generally, as fluid channel 766. The connector 760 may be in fluid communication with a fluid reservoir via a first valve 762a (or a valved connection including a valve 762a). The first valve 762a may be a ball valve, a butterfly valve, a check valve, a control valve, a diaphragm valve, a hygienic valve, a corrosion-resistant valve, a pressure valve, a Luer-activated valve, and the like. In embodiments, the connector 760 may include ergonomic features and hygienic features such as finger indentations, coverings/finger guards/barriers near the couplers 764a, 764b, removable caps on the couplers 764a, 764b, an optimized length of the connector 760, a removable external clip or housing around the connector 760, and/or other features designed to prevent a user from accidentally contaminating the couplers 764a, 764 during connection steps.

In certain embodiments of the present disclosure, the connector 760, as described above, is fluidically coupled to the fluid flow control device 700 via the first valve 762a and to the peritoneal dialysis tubing via the first coupler 764a and the second coupler 764b to perform sterilization of the peritoneal dialysis tubing. Following setting the first valve 762a to an 'open' state, such that fluid can flow therethrough and into the connector 760, sterilization fluid from the fluid reservoir may be delivered to the peritoneal dialysis tubing via the fluid channel 766 of the connector 760. Additionally, after delivering the sterilization fluid from the fluid reservoir, the sterilization fluid can be retracted from the peritoneal dialysis tubing via the fluid channel 766 of the connector 760 back into the fluid reservoir. After sterilization and retraction of the sterilization fluid from the peritoneal dialysis tubing and the connector, the first valve 762a may be set to a 'closed' state, such that fluid cannot flow therethrough. Optionally, in embodiments, a controller 710 of the fluid flow control device 700 may control execution of instructions related to dispensation or injection of sterilization fluid from the fluid reservoir, such as setting the first valve 762a to proper states and controlling expulsion and retraction of sterilization fluid therethrough. For example, the controller 710 of the fluid flow control device 700 may control a state of each valve 762a, 762b upon connection and disconnection of the fluid reservoir. Alternatively, the controller 710 can control certain operations of injecting and/or retracting the sterilization fluid, while not controlling other operations (e.g., where such other operations are manually controlled by a user). For example, a user can control the opening and/or closing of the valve 762a, 762b, and/or the injection and/or retraction of the sterilization fluid.

In certain embodiments, the connector 760 includes a first flexible part 769a and a second flexible part 769b. A size of a lumen of the first flexible part 769a and the second flexible part 769b may be controlled by the controller 710 of the fluid flow control device 700 via a first flow control element 770a and a second flow control element 770b. The first and second flexible parts 769a, 769b can be can be selectively closed or opened, e.g., to allow fluid flow through the respective fluid channel sides 771a, 771b. This can facilitate, for example, sterilization of different portions of the peritoneal dialysis tubing in sequence or separately, such as, for example, sterilization of the transfer set tubing before or after sterilization of the cassette tubing (e.g., by closing the respective first and second flexible parts 769a, 769b).

Optionally, in some embodiments, the size of the lumen of the first flexible part 769a and the second flexible part 769b, may be varied as a percentage of a total size of the lumen in order to vary flow to the first fluid channel 766a and to the second fluid channel 766b. This can be useful, for instance, when different in-line pressures or air volumes exist on either side of the connector 760 and within the peritoneal dialysis tubing. When pressure or air volume is higher on one side of the connector 760 than the other, adequate sterilization of both sides of the peritoneal dialysis tubing can be complicated under normal, open flow conditions within the channel 766. Thus, by controlling a lumen size of the first flexible part 769a and the second flexible part 769b, fluid flow along a length of the connector 760 defined by the fluid channel 766 and a longitudinal axis 767, thereof, sterilization of the peritoneal dialysis tubing on each side of the connector 760 can be controlled and balanced. In embodiments, control of the first flexible part 769a and the second flexible part 769b may be informed, dynamically and in real time, by pressure sensors included within the connector 760 and/or other sensors within the connector 760 configured to detect a presence of fluid. In embodiments, pressure sensors, not shown in FIG. 7, may be integrated with the first coupler 764a and/or the second coupler 764b, within the first flexible part 769a and/or the second flexible part 769b, and/or within walls of the fluid channel 766, and the like. Accordingly, the pressure sensors may be operatively coupled to the controller 710 of the fluid flow control device 700, so that the first flow control element 770a and the second flow control element 770b can be adjusted in real time responsive to the demands of the pressure profile of the connector 760. Similarly, in embodiments, the fluid sensors, not shown in FIG. 7, may be integrated within the first coupler 764a and/or the second coupled 764b, within the first flexible part 769a and/or the second flexible part 769b, and/or within walls of the fluid channel 766, and the like. Accordingly, the fluid sensors may be operatively coupled to the controller 710 of the fluid flow control device 700, so that the first flow control element 770a and the second flow control element 770b can be adjusted in real time responsive to the demands of the pressure profile of the connector 760.

As can be appreciated, the above description of the connector 760 allows for simultaneous sterilization of both sides (or both portions) of the peritoneal dialysis tubing via the first coupler 764a and the second coupler 764b. Further to the above, in certain embodiments, sterilization of the peritoneal dialysis tubing may be sequential and/or directional, wherein one side of the connector and the peritoneal dialysis tubing is sterilized separately from the other, thus substantially eliminating issues associated with variable line pressures in the peritoneal dialysis tubing.

In embodiments, wherein the connector 760 is configured for directional sterilization of the peritoneal dialysis tubing, the connector 760 may include a flow diverter 768. The flow diverter 768 may be set to different configurations such that sterilization fluid may flow toward a first fluid channel side 771a or toward a second fluid channel side 771b according to the configuration to which the flow diverter 768 is set. In certain embodiments, the connector 760 may optionally include a second valve 762b, controllable by the controller 710 of the fluid control device 700, and the sterilization fluid may flow to, separately, both of the first fluid channel side 771a and the second fluid channel side 771b when the flow diverter 768 is set to a corresponding configuration. The second valve 762b may be a ball valve, a butterfly valve, a check valve, a control valve, a diaphragm valve, a hygienic valve, a corrosion-resistant valve, a pressure valve, a Luer-activated valve, and the like. The flow diverter 768, variations of which will be described in detail with reference to later figures, may generally be one or more of a stopcock, a barrier, a valve, a clamp, or other structure providing directional flow control.

In some embodiments, the couplers 764a 764b can be rotatable such that tubing connected to each of the couplers can rotatably move relative to the connector 760, e.g., such that the connector 760 does twist or tangle the peritoneal dialysis tubing. Alternatively, in some embodiments, the connector 760 can include rotatable sections (not schematically depicted) disposed near the couplers 764a, 764b that allow for rotatable movement of the tubing connected to the connector 760 relative to at least portions of the connector 760.

Figure 8:
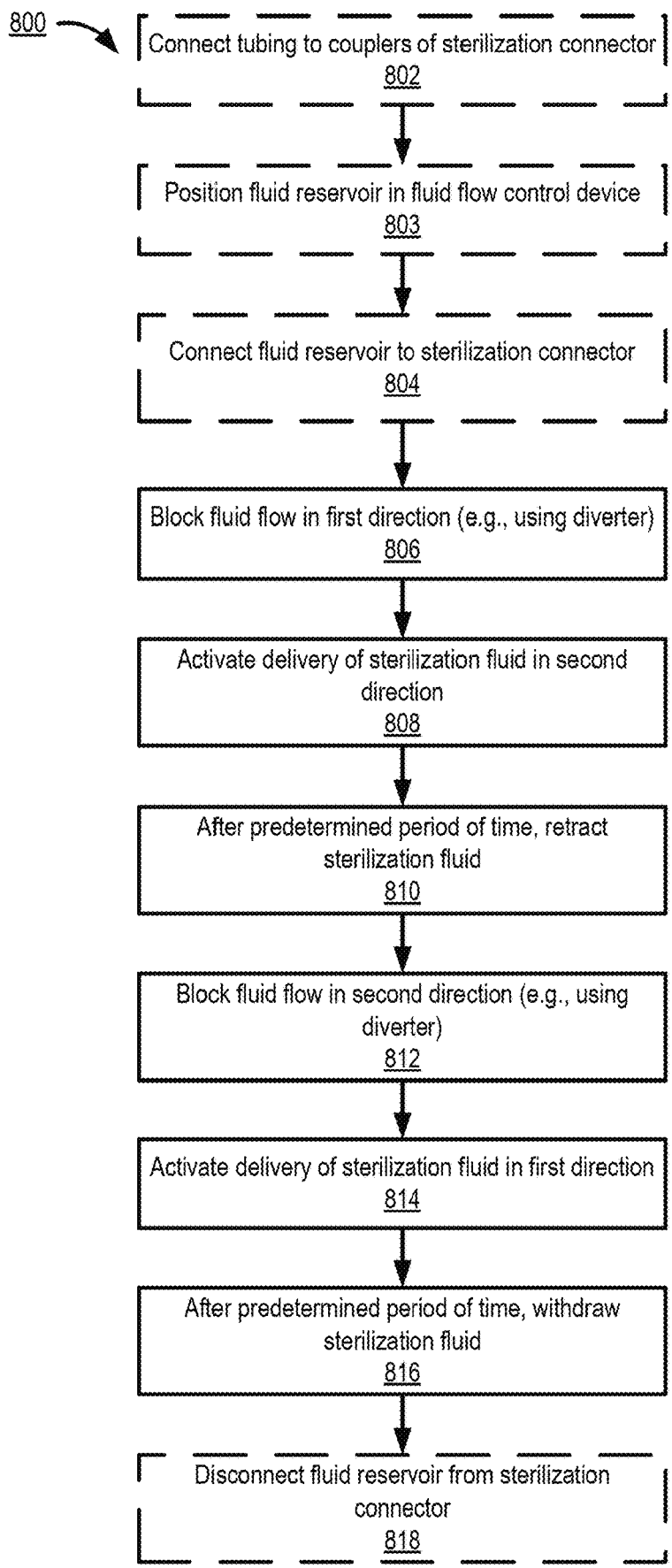
FIG. 8 is a flow diagram of a method of injecting and retracting sterilization fluid, via a fluid flow control device, within a connector and dialysis tubing, according to embodiments of the present disclosure.
Figure 9:
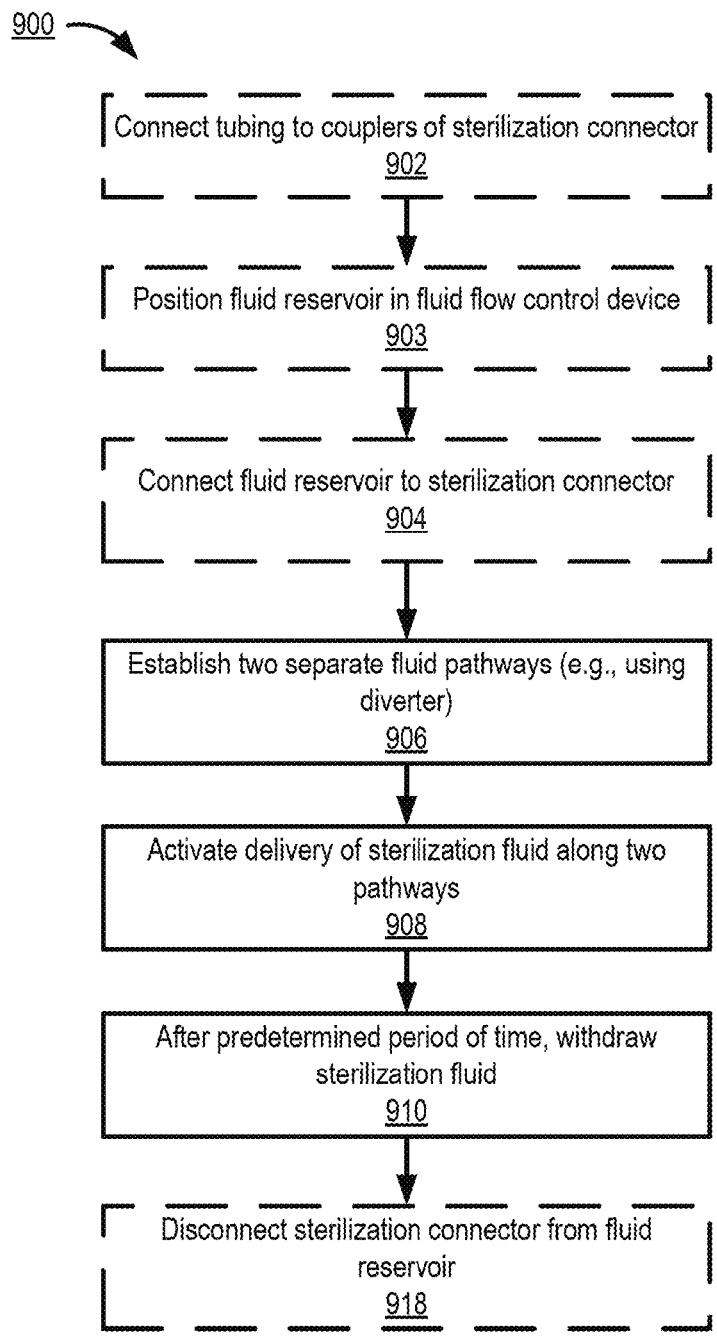
FIG. 9 is a flow diagram of a method of injecting and retracting sterilization fluid, via a fluid flow control device, within a connector and dialysis tubing, according to embodiments of the present disclosure.

FIG. 8 and FIG. 9 depict flow diagrams associated with the operation of systems for sterilizing medical tubing, as described herein, including, for example, systems including one or more of the fluid flow control devices 500, 700, the fluid reservoir 650, and/or the connector 760.

FIG. 8 provides a flow diagram of the operation of a system including a connector (e.g., connector 760), wherein directional and/or sequential sterilization of the peritoneal dialysis tubing is performed.

At 802 of process 800, first and second tubing of the peritoneal dialysis tubing can be respectively connected to first and second couplers at each end of the connector (e.g., couplers 764a, 764b). Concurrently, or separately, at 803, a fluid reservoir (e.g., fluid reservoir 650) can be positioned within and/or engaged with a fluid reservoir interface (e.g., fluid reservoir interface 540) of a fluid flow control device (e.g., fluid flow control device 500). At 804, the fluid reservoir and/or the fluid flow control device can be connected to the connector (e.g., via a valved connection, such as, for example, a connection including valve 762a) to begin the sterilization process. It can be appreciated that 802, 803, and 804 can be optional, as the connector and/or the fluid reservoir may already be coupled to the peritoneal tubing and/or fluid flow control device for a particular sterilization session, and therefore can be omitted.

At 806, fluid flow can be blocked in a first direction, e.g., using one or more valves or flow diverters. For example, a flow diverter (e.g., flow diverter 768) of the connector can be set to a first configuration to block fluid flow in the first direction (or to a first portion of the connector) so that sterilization fluid from the fluid reservoir is directed to flow in a second direction (or to a second portion of the connector). Alternatively, a flow control element (e.g., flow control element 770a) can be activated to close a flexible part of a fluid channel in the first direction (e.g., flexible part 769a) to block fluid flow in the first direction. Still alternatively, a valve or other flow control mechanism positioned along the fluid channel in the first direction can be closed to block fluid flow in the first direction. At 808, injection is actuated and delivery of the sterilization fluid along the second direction and to a second side or portion of the connector is performed. The actuation of the injection of the sterilization fluid can be as described with respect to FIG. 3, wherein fluid flow rates are between about 0.15 mL/sec and about 0.6 mL/sec. After a predetermined period of time, or a dwell time of the sterilization fluid within the second side or portion of the connector and tubing connected to that side, retraction of at least a substantial majority of the sterilization fluid out of the second side or portion of the connector and the connected tubing is actuated, at 810. The dwell time may be one as described previously with respect to FIG. 3. For instance, the dwell time may be between about 1 second and about 10 seconds, including all values and sub-ranges therebetween.

At 812, the fluid flow in the first direction can be opened and the fluid flow in the second direction can be blocked. For example, the same flow diverter may be set to a second configuration to block fluid flow in the second direction (or to the second portion of the connector) so that sterilization fluid from the fluid reservoir is directed in the first direction of the connector (or to the first portion of the connector). Alternatively, a different flow diverter may be set to a certain configuration so that fluid flow in the second direction is blocked. Still alternatively, a flow control element (e.g., flow control element 770b) can activate to close a flexible part a fluid channel in the second direction (e.g., flexible part 769b) to block fluid flow in the second direction. At 814, injection is actuated and delivery of the sterilization fluid along the first direction and to a first side or portion of the connector is performed. The actuation of the injection of the sterilization fluid can be as described with respect to FIG. 3, wherein fluid flow rates are between about 0.15 mL/sec and about 0.6 mL/sec. After a predetermined period of time, or a dwell time of the sterilization fluid within the first side or portion of the connector and tubing connected to that side, retraction of at least a substantial majority of the sterilization fluid out of the first side or portion of the connector and the connected tubing is actuated, at 816. The dwell time may be one as described previously with respect to FIG. 3. For instance, the dwell time may be between about 1 second and about 10 seconds, including all values and sub-ranges therebetween.

After retraction of at least a substantial majority of the sterilization fluid from the connector, the fluid reservoir can be disconnected from the connector, at 818. While not depicted in FIG. 8, fluid flow in the second direction can be opened such that fluid flow in both first and second directions are open to allow dialysis solutions to be flowed therethrough and through the peritoneal dialysis tubing. In some embodiments, fluid flow can be opened by setting a flow diverter to a third configuration that allows fluid flow in the first and second directions. In some embodiments, the third configuration of the flow diverter may be one that blocks the opening and/or port through which the sterilization fluid was provided, the opening and/or port being orthogonal to an axis defined by the first direction and the second direction, the blocking of the opening and/or port preventing contamination of the connector and fluid leakage during peritoneal dialysis. Such a third configuration may be realized by a stopcock rotated such that the opening and/or port is blocked and fluid flows freely through the stopcock and in the first direction and the second direction. In some embodiments, fluid flow can be opened by opening one or more valves, flexible parts, etc. of the fluid flow channels within the connector, e.g., as described with reference to FIG. 7.

Directional sterilization, as depicted in FIG. 8, may be performed at different times or sequentially. Directional sterilization may also be performed simultaneously, as will be described with reference to the flow diagram of FIG. 9. In some embodiments, as described above, multiple fluid reservoirs containing sterilization fluid can be coupled to a sterilization connector (e.g., connector 760). For example, the connector 760 may include first and second valved connection for controlling flow of sterilization fluid into first and second sides or portions of the connector. Thus, with utilization of a flow diverter in a proper configuration, two separate fluid flow paths can be established to sterilize each side or portion of the connector and the peritoneal dialysis tubing. Alternatively, instead of using multiple fluid reservoirs, two fluid flow paths can be established and placed in fluid communication with a single fluid reservoir such that sterilization fluid exiting the fluid reservoir can be directed down two flow paths and into first and second sides or portions of the connector (and tubing connected therewith).

Similar to the process 800 described with respect to FIG. 8, at 902 of process 900, tubing of the peritoneal dialysis tubing can be connected to couplers at each end of the connector. Concurrently, or separately, at 903, a fluid reservoir can be positioned within a fluid reservoir interface of the fluid flow control device. At 904, the fluid reservoir and/or the fluid flow control device can be connected to the connector to begin the sterilization process. It can be appreciated that 902, 903, and 904 can be optional, as one or more of these may already be performed prior to a particular sterilization session and therefore not necessary for that session.

At 906, a flow diverter of the connector can be set to a first configuration so that two separate fluid flow pathways are established and sterilization fluid from the fluid reservoir is permitted to flow to a first side and a second side of the connector, separately but at the same time. These two separate fluid pathways may be established, for example, using a flow diverter and/or by using one or more valves (e.g. coupled to different fluid reservoirs). As described above with reference to FIG. 7, the flow diverter may be a barrier or other device that, in a first configuration, is set to prevent fluid flow between the first side or portion of the connector and the second side or portion of the connector, therefore effectively establishing two separate fluid pathways. At 908, delivery of the sterilization fluid into both of the first side or portion of the connector and the second side or portion of the connector is actuated. The actuation of the sterilization fluid can be as described with respect to FIG. 3, wherein fluid flow rates are between about 0.15 mL/sec and about 0.6 mL/sec. After a predetermined period of time, or a dwell time of the sterilization fluid within the first and second sides of the connector and the tubing connected therewith, retraction of at least a substantial majority of the sterilization fluid is actuated, at 910. The dwell time may be one as described previously with respect to FIG. 3. For instance, the dwell time may be between about 1 second and about 30 seconds. After retraction of at least a substantial majority of the sterilization fluid from the connector, the fluid reservoir can be disconnected from the connector, at 918. While not depicted in FIG. 9, it can be appreciated that the flow diverter can be subsequently set to a second configuration, wherein the barrier is removed, either manually or automatically by the fluid flow control device, thus allowing fluid flow between the first side of the connector and the second side of the connector and allowing dialysis solutions to be flowed through the peritoneal dialysis tubing via the connector.

Referring now to FIG. 10A through FIG. 12C, an example system including a fluid flow control device, according to certain embodiments, is described. The fluid flow control device, fluid reservoir, and other components depicted in FIGS. 10A through 12C can be structurally and/or functionally similar to like components, as described above with respect to other figures. Accordingly, for conciseness of disclosure, certain aspects of such components are not described with reference to these figures again.

Figure 10A:
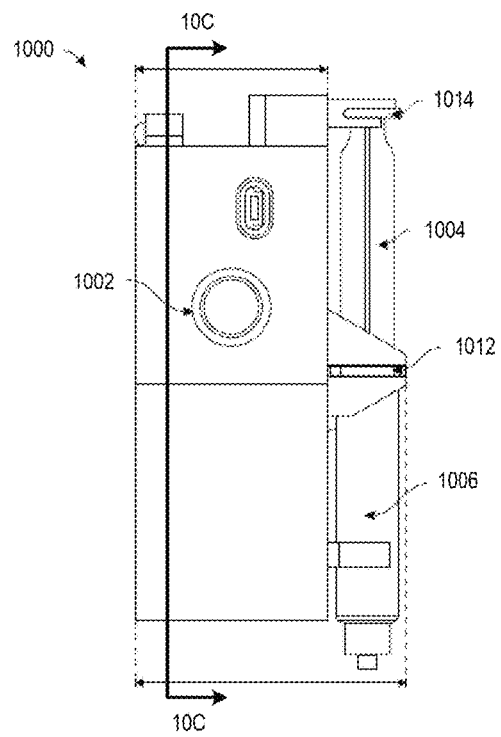
FIGS. 10A and 10B are side and front views, respectively, of an example system for performing sterilization, according to embodiments of the present disclosure.
Figure 10B:
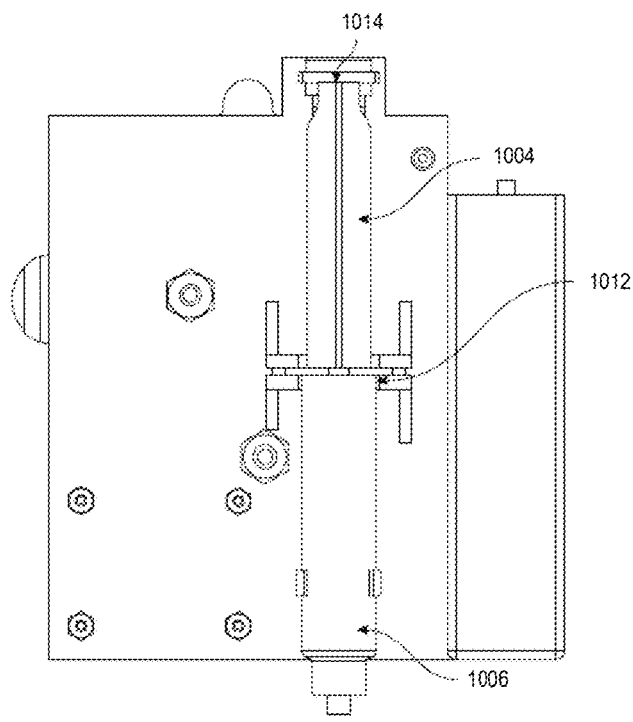

FIGS. 10A and 10B are side and front views of various aspects of the example system. As shown in FIGS. 10A and 10B, system 1000 may include an injection activation switch 1002, a power switch 1020, and fluid reservoir implemented as a syringe that includes a barrel 1006 and a plunger or dispensing element 1004.

The injection activation switch 1002 can be configured to interface with a motor or drive mechanism 1010. The switch 1002 can be configured to output a signal to the motor 1010 when it moves from one state to another state (e.g., a button or a latch). In some examples, the switch 1002 may be slidable, whereby sliding the switch outputs a signal. In some examples, the switch 1002 may be a touchscreen or LCD screen interface. In some examples, the switch 1002 may be depressed to output a signal to activate injection, which will be further described with reference to FIG. 10C. The plunger 1004 may be engaged with a plunger housing 1014. The barrel 1006 may be engaged with a barrel housing 1012.

The plunger 1004 interfaces with the barrel 1006. The barrel 1006 may be configured to store fluids, such as a disinfecting or sterilization solution. The barrel 1006 may interface with a connector, which may interface with an external tube or transfer set, e.g., of a peritoneal dialysis system. The plunger 1004 may be depressed in order to cause injection of the fluid stored in the barrel 1006. The plunger 1004 may be retracted in order to cause removal of the fluid. In some examples, the fluid in the barrel 1006 may be retracted by other means, such as a pump.

Figure 10C:
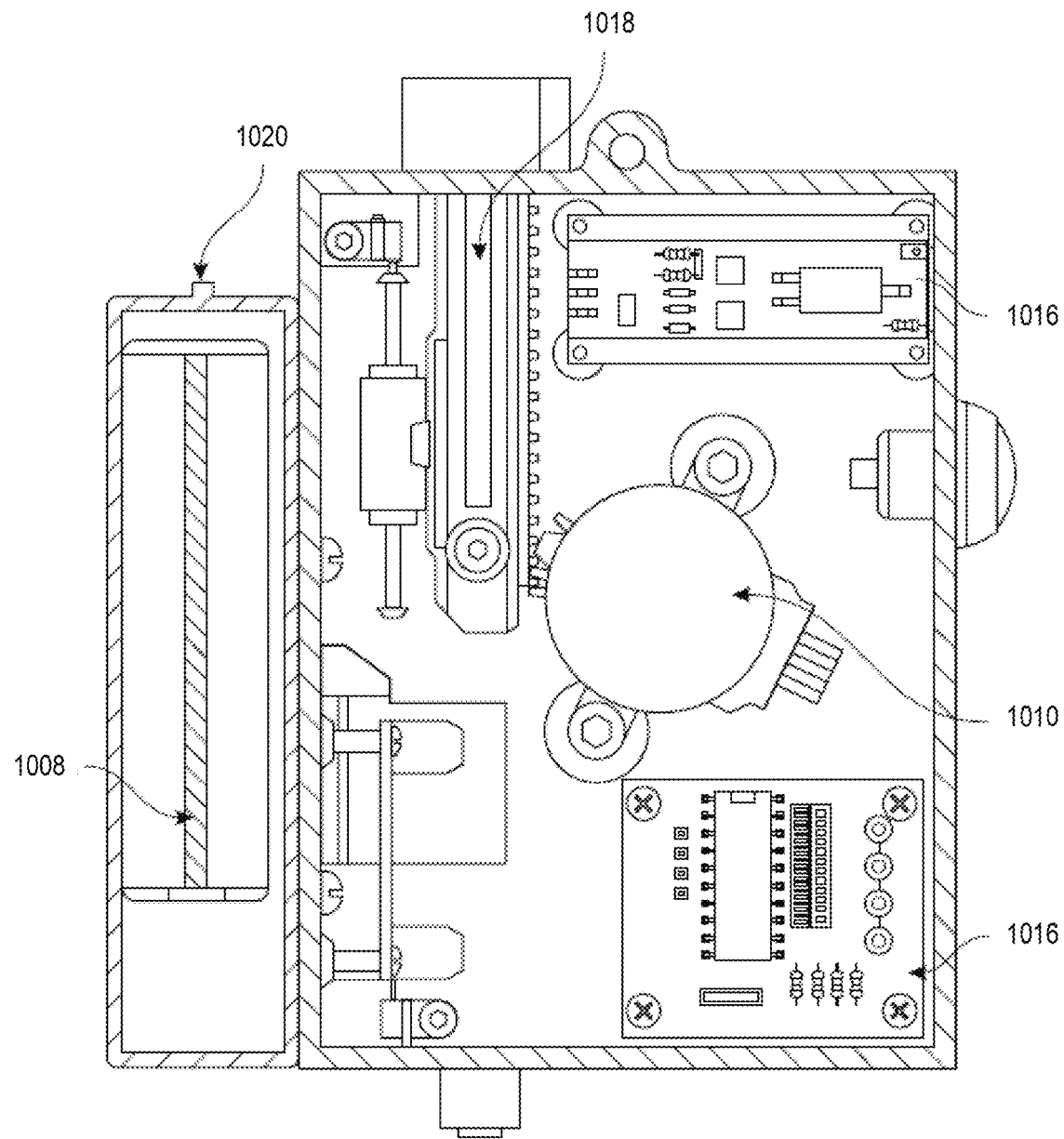
FIG. 10C is a view of various internal components of the example system of FIGS. 10A and 10B, according to embodiments of the present disclosure.

FIG. 10C is a cross sectional view of system 1000, taken along line 10C-10C through FIG. 10B, showing internal components of system 1000. The system 1000 may be powered by a power source, such as a battery 1008 or a power outlet. The battery 1008 may interface with a power switch 1020, whereby depressing the power switch 1020 can power on system 1000. Alternatively, in some examples, the power switch 1020 may power on system 1000 by sliding the power switch 1020. As noted above, the switch 1020 can be configured to output a signal when it moves from one state to another state. Once system 1000 is powered on, the switch 1002 may be depressed in order to activate motor or drive mechanism 1010. The motor 1010 of the system 1000 is powered by an energy supply that may be provided by the rechargeable or disposable battery or batteries 1008. In some embodiments, the system can include a user interface such as a touchscreen or LCD screen that can display when the injection or retraction is complete, battery life, pressure levels, flow rate, error states, and/or other information associated with the operation of the system. In alternative embodiments, there may not be a power switch 1020, and injection activation switch 1002 can be configured to both power on the fluid flow control device from a dormant or sleep mode and output a signal to activate injection.

The motor 1010 may be a stepper motor, servo motor, or direct current (DC) motor. The motor 1010 may be used as a driving means to activate a linear actuator 1018. In some embodiments, the linear actuator 1018 may be mechanical, electro-mechanical or electrical. In such embodiments, linear actuator 1018 may be moved back and forth by the motor 1010. in some embodiments, the motor may produce a rotational motion, and the torque provided by the motor 1010 may be transferred to the plunger 1004 by the linear actuator 1018. The linear actuator 1018 can therefore be configured to convert the rotational motion of the motor to a linear motion of the plunger 1004. The linear actuator 1018 may be or include, for example, one or more of a ball and spindle, rack and pinion gear, cam, gears, belts, screw (e.g., ball screw, roller screw, or lead screw), wheel and axle, chain, cable, or the like. The motor 1010 may rotate a fraction of a rotation and stop and dwell for a predetermined period of time. As such, the motor 1010 may be able to depress (i.e., inject) or retract plunger 1004 for as long as necessary. In such cases, an onboard processor or control unit (e.g., electrical control system 1016) in the fluid flow control device can be configured to control the operation of the motor, e.g., to control plunger depression (and therefore amount and/or rate of fluid injection), the predetermined period of time that the plunger remains depressed (and therefore the dwell time), and/or plunger retraction (and therefore amount and/or rate of fluid retraction). In some embodiments, the linear actuator 1018 may be hydraulic, pneumatic, or piezoelectric and directly interface with an electrical control system 1016. In some embodiments, the linear actuator 1018 may be electromagnetic (e.g., linear solenoid). In such embodiments, no motor 1010 may be necessary to power the hydraulic, pneumatic, or piezoelectric actuator.

The system 1000 can include an electrical control system 1016 that controls the various features, including, for example, the motor 1010. The electrical control system 1016 may include, for example, a printed circuit board (PCB) or an analog circuit. In some examples, the electrical control system 1016 may include a microcontroller (e.g., an Arduino Nano) and a motor driver board. In some embodiments, the electrical control system 1016 may control the speed of the motor 1010, the amount of time that the motor is activated, when to pause the movement of the motor (e.g., to achieve sufficient dwell time and/or in response to detecting a safety issue), etc. In some embodiments, the torque transferred to plunger 1004 may be controlled by the electrical control system 1016 to deliver the required speed. The injection and/or retraction speed may be pre-programmed on the microcontroller of the electrical control system 1016, e.g., by a user. In some embodiments, the electrical control system 1016 may control the height of the plunger 1004 by adjusting the plunger 1004 to a specified injection height (e.g., a height corresponding to 1.0 mL). The height may be programmed on the microcontroller, e.g., by the user. In some embodiments, the electrical control system 1016 may control how long to keep the plunger 1004 depressed. In some embodiments, the electrical control system 1016 may control when to retract the plunger 1004. For example, the plunger 1004 may be depressed for a predetermined time and retracted after the predetermined time. The time may be pre-programmed on the microcontroller, e.g., by the user. In some embodiments, the parameters associated with the operation of the motor 1010 (or other drive and/or actuation components in the system) can be selectively set, e.g., by a user via a user interface on the fluid flow control device or on a separate compute device that is communicatively coupled to the device (e.g., via a communication interface as described above). For example, a user may use a user interface (e.g., an application interface) on a compute device (e.g., a mobile device) to program one or more parameters of the operation of the motor 1010 (e.g., distance of the plunger to depress, rate of depressing plunger, dwell time, distance of the plunger to retract, and rate of retraction), and such parameters can be communicated to the microprocessor such that the microprocessor controls the motor 1010 to operate accordingly.

Figure 11:
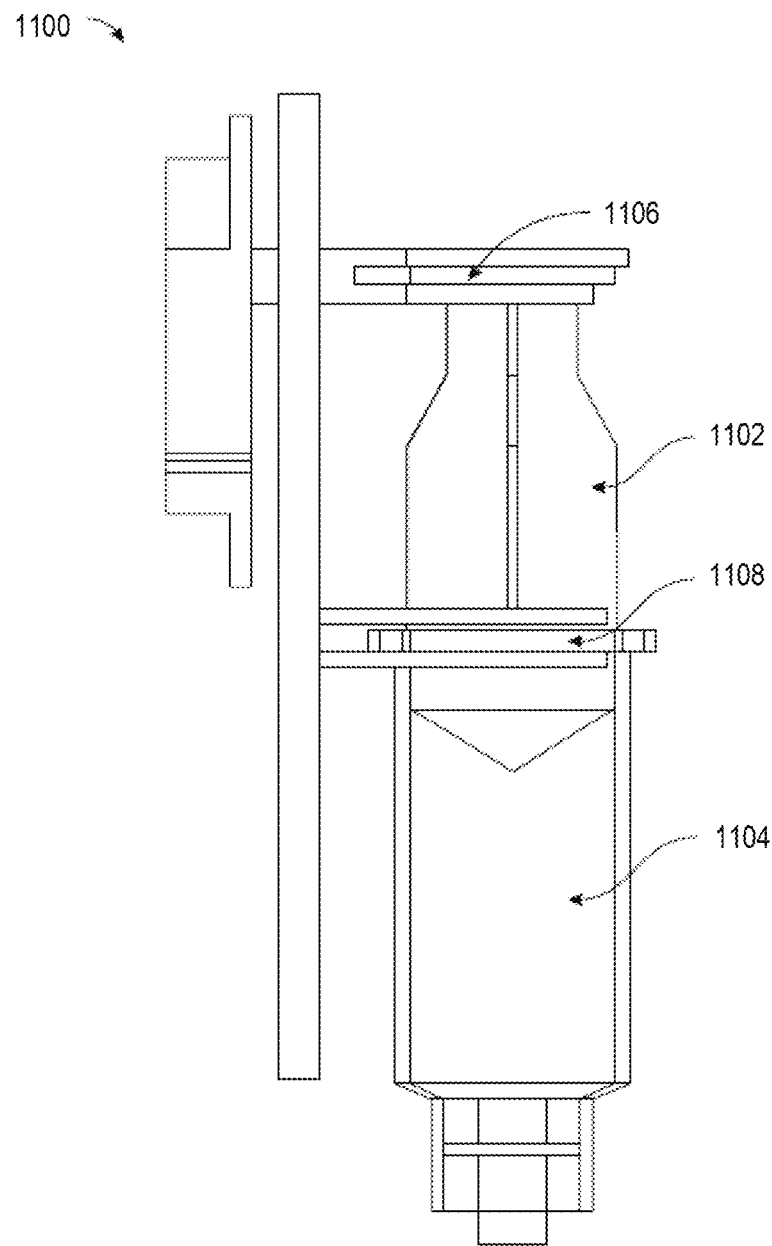
FIG. 11 is a schematic diagram of various aspects of a plunger housing and fluid reservoir housing, according to embodiments of the present disclosure.

FIG. 11 is a schematic diagram of various aspects of the plunger housing 1106 and barrel housing 1108, according to embodiments. The plunger housing 1106 and the barrel housing 1108 can be components of a fluid flow control device 1100, e.g., similar to other fluid flow control devices described herein. A fluid reservoir implemented as a syringe and including a plunger 1102 and a barrel 1104 can be received in and engaged with the fluid flow control device 1100, e.g., via the plunger housing 1106 and the barrel housing 1108, respectively. The plunger 110 and the barrel 1104 can together define a space for containing a sterilization fluid. The plunger 1102 of a fluid reservoir is configured to fit within the plunger housing 1106. And the barrel 1104 of a fluid reservoir is configured to fit within the barrel housing 1108. In some embodiments, the plunger housing 1106 and the barrel housing 1108 may be reusable, while the plunger 1102 and barrel 1104 (i.e., the fluid reservoir) may be disposable. In some examples, the barrel 1104 may be filled with fluid prior to being loaded into the barrel housing 1108. In some examples, the barrel 1104 may be empty when it is being loaded into the barrel housing 1108. In some examples, the connection of the barrel 1104 to the barrel housing 1108 is accomplished by a clamp, screw, twist, press fit, snap fit, a clearance fit, or other mechanical mechanism.

In one example, as illustrated in FIG. 11, a press fit is used and the barrel 1104 is pressed into at least two clamping arms that extend from the fluid flow control device 1100. The two arms that extend from the fluid flow control device 1100 may form the barrel housing 1108. The two arms (e.g., one upper arm and one lower arm, or two laterally spaced arms) may be parallel to each other horizontally with respect to the fluid flow control device 1100. The two arms may be fixed to prevent axial translation of the barrel 1104 when it is loaded therein. The barrel 1104 may be removed or ejected horizontally or vertically from the barrel housing 1108.

Likewise, the plunger 1102 is pressed into at least two clamping arms that extend from the fluid flow control device 1100. The two arms that extend from the fluid flow control device 1100 may form the plunger housing 1106. The two arms (e.g., one upper arm and one lower arm, or two laterally spaced arms) may be parallel to each other horizontally with respect to the fluid flow control device 1100. The two arms may be movable to depress and retract the plunger 1102. The plunger 1102 may be removed or ejected horizontally or vertically from the plunger housing 1106.

In other examples, not illustrated, the plunger 1102 or barrel 1104 may be attached to plunger housing 1106 or barrel housing 1108, respectively, via a snap fit. The barrel 1104 and/or the barrel housing 1108 and the plunger 1102 and/or the plunger housing 1106 may be made of flexible material that can be secured together by pushing the barrel 1104 and the barrel housing 1108 together and/or the plunger 1102 and the plunger housing 1106 together. In other examples, a screw or threaded connection may be used and the barrel 1104 is screwed together with the barrel housing 1108.

In other examples, a rotating or twist connection and ejection mechanism may be implemented as a connection mechanism. The top of plunger 1102 or barrel 1104 may be modified in shape and there may be one or more tabs on the plunger housing 1106 or barrel housing 1108. The tabs on the plunger housing 1106 or barrel housing 1108 may lock the plunger 1102 or barrel 1104 in place by turning the plunger 1102 or barrel 1104 clockwise or counter-clockwise and the plunger 1102 or barrel 1104 may be removed by turning it the opposite direction. In some examples, the plunger 1102 or barrel 1104 may be rotated a quarter-turn to be locked in place and a quarter-turn in the opposite direction to be removed.

Another example of the ejection mechanism may be that the clamp may release the barrel 1104 from the barrel housing 1108 when the clamp is horizontally pressed. In other examples, a press or snap fit may have a vertical ejector that is spring loaded at the top and has a ring at the bottom, which lies between the barrel 1104 and the barrel housing 1108. The ring may push down on the barrel 1104 to disconnect it from the snap fit. In another example, the barrel 1104 may be manually ejected from, for example, the snap fit.

While specific examples of couplings between the barrel and plunger of the fluid reservoir and their respective housings are described herein, it can be appreciated that any type of suitable coupling can be used to secure the components of the fluid reservoir to receiving components in the fluid flow control device. For example, in some variations, an interface between the fluid reservoir and receiving components in the fluid flow control device can be a clearance fit. To this end, there may be clearance both above and below the plunger when it is assembled in the plunger housing. When the plunger housing moves down, an interior top face of the plunger housing will interact with a top face of the plunger and push it down. When the plunger housing moves up, an interior bottom face of the plunger housing will interact with a bottom face of the plunger and pull it upward. In some variations, an interface between the fluid reservoir and the barrel housing may be a cavity shaped to fit the fluid reservoir and thereby align and secure the fluid reservoir.

Figure 12A:
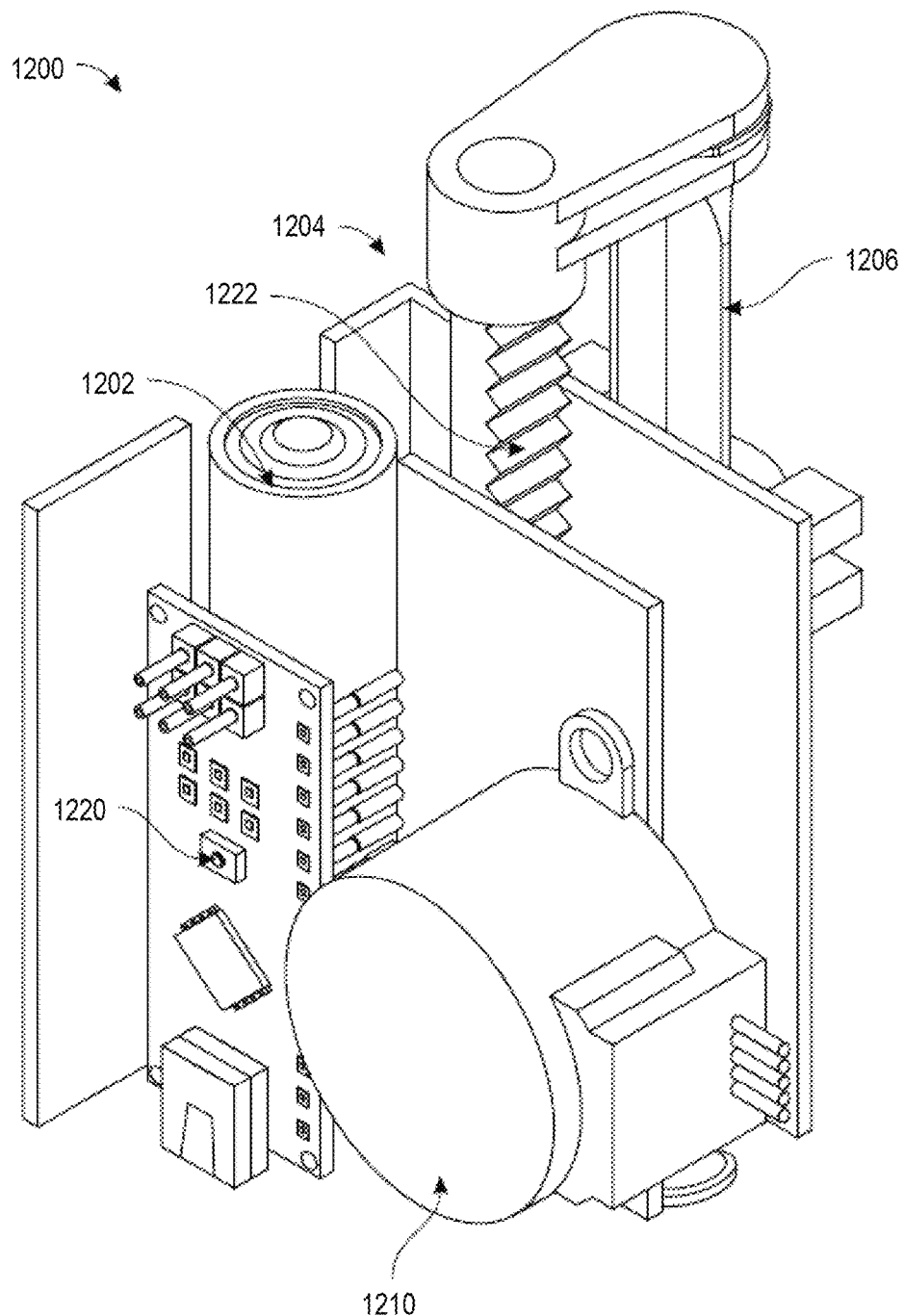
FIG. 12A, FIG. 12B, and FIG. 12C are diagrams illustrating various aspects of a fluid flow control device, according to embodiments of the present disclosure.
Figure 12B:
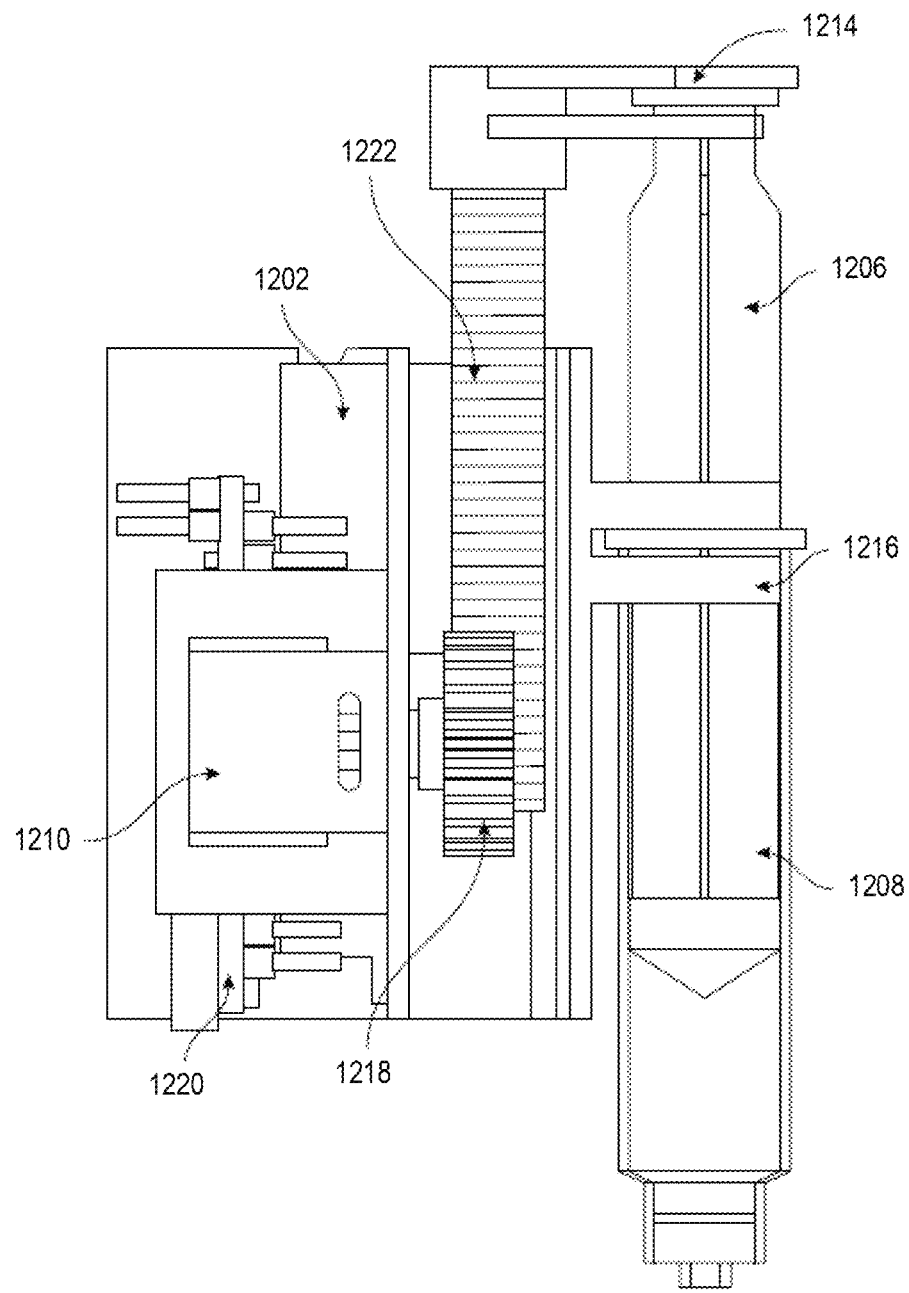
Figure 12C:
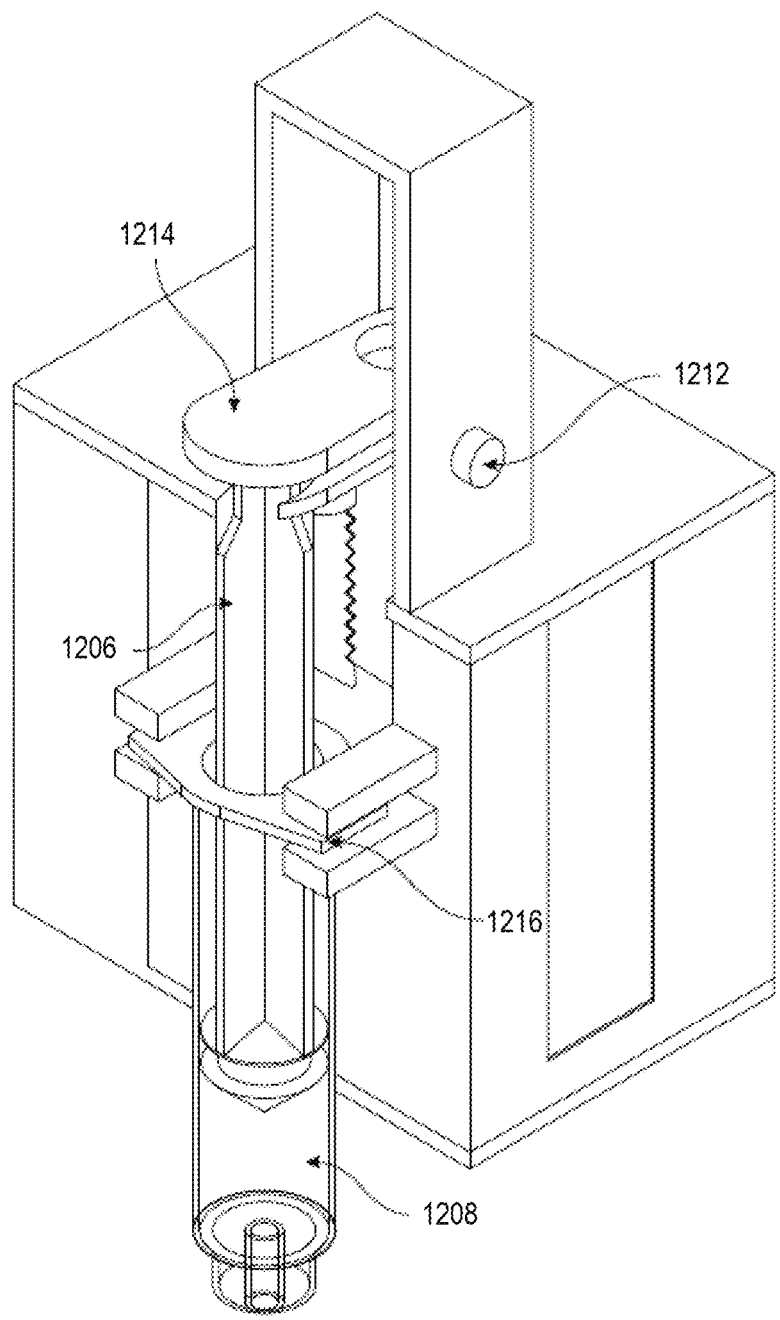

FIGS. 12A, 12B, and 12C are schematic diagrams illustrating various aspects of another example fluid flow control device 1200, according to embodiments. With reference to FIG. 12A, the fluid flow control device 1200 includes a battery 1202, motor 1210, electrical control system 1220, and a gear rack assembly 1204. The fluid flow control device 1200 can be configured to receive a fluid reservoir including a plunger 1206. The fluid flow control device 1200 and the fluid reservoir can including components that are structurally and/or functionally similar to components of other fluid flow control devices and fluid reservoirs, respectively. In some embodiments, the plunger 1206 (and other components of the fluid reservoir) can be disposable, while the fluid flow control device 1200 can be reusable. The gear rack assembly 1204 includes rack 1222 and gear 1218, which is shown in FIG. 12B. The gear rack assembly 1204 is coupled to the motor 1210 and used to depress the plunger 1206.

With reference to FIG. 12B, the rack 1222 is coupled to the plunger housing 1214, which in turn is coupled to the plunger 1206. The rotation output of the motor 1210 and the gear 1218 drives the linear motion of plunger 1206. The linear motion of the plunger 1205 causes sterilization fluid to be injected from the fluid reservoir and into a connector (not shown) coupled to the fluid reservoir. The fluid reservoir can include a barrel 1208 in which the plunger 1205 is disposed. The plunger 1205 and the barrel 1208 can collectively define a space for receiving sterilization fluid. The gear rack assembly 1204 is configured to produce a rotation output. The rotation output may provide a number of injection speeds, e.g., by user configurable settings in the electrical control system 1220. FIG. 12C is another angle of the fluid flow control device 1200, in which a button 1212 is depressed in order to activate the motor and linear actuator to begin the process of injection and retraction of the sterilization fluid in the fluid reservoir 1208.

FIG. 13A through FIG. 13D provide illustrations of aspects of a fluid flow control device 1300, according to embodiments of the present disclosure. The fluid flow control device 1300 can include components that are structurally and/or functionally similar to that of other fluid flow control devices described herein, including, for example, fluid flow control device 500, 1100, 1200, etc.

As shown in FIG. 13A and FIG. 13B, the fluid flow control device 1300 may include a housing 1302. The housing 1302 may include a control switch 1310 and a power source indicator viewing window 1308 disposed through a surface thereof. As in FIG. 13A, the control switch 1310 may be an on/off switch and/or may be a start/stop switch that controls execution of one or more processes, as outlined above. In FIG. 13B, the control switch 1310 may be a start/stop switch that controls execution of one or more processes, as outlined above, and the housing 1302 may further include a power switch 1312 that may be an on/off switch controlling power to the fluid flow control device 1300. In both of FIG. 13A and FIG. 13B, the housing 1302 may include a fluid reservoir interface 1340 engaged with a fluid reservoir 1350 including a syringe plunger 1304 and a syringe barrel 1306. A syringe plunger flange holder 1318 configured to secure a flange of the syringe plunger 1303 may be included within an actuation system of the fluid flow control device 1300 and operatively coupled to the fluid reservoir 1350. The syringe plunger flange holder 1318 may be configured to translate actuation into linear translation of the syringe plunger 1304, as shown with arrows in FIG. 13B.

Figure 13C:
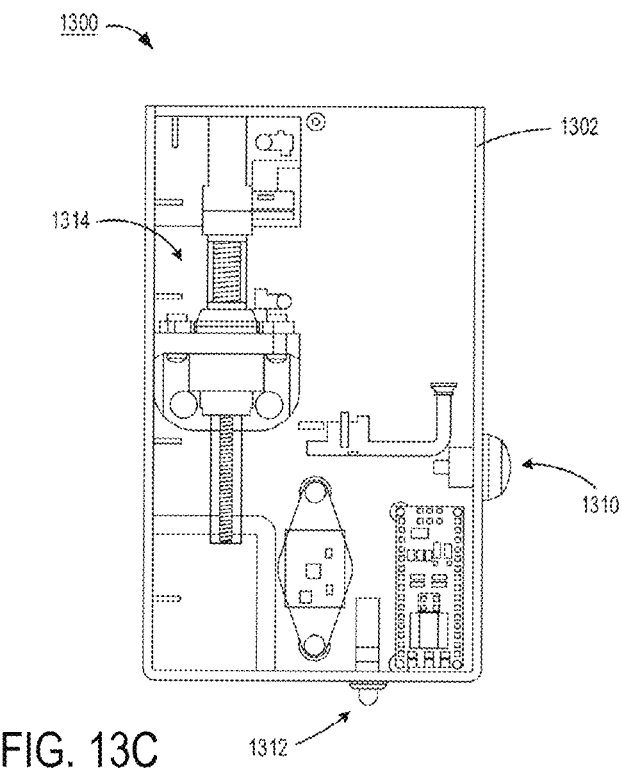
Figure 13D:
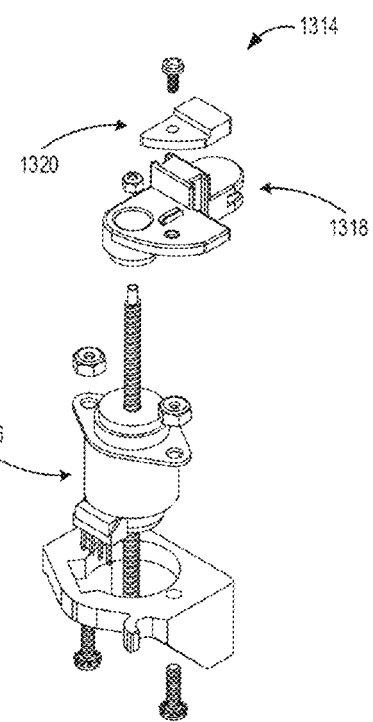

FIG. 13C and FIG. 13D provide illustrations of interior components of the fluid flow control device 1300. An internal compartment of the housing 1302 of the fluid flow control device 1300 may include an actuation system 1314. The housing 1302 may include, as in FIG. 13B, a control switch 1310 and a power switch 1312. FIG. 13D provides a detailed illustration of the actuation system 1314. The actuation system 14 may include a linear actuator 1316, an actuator limit 1320, and a syringe plunger flange holder 1318. Similar to embodiments described above, the syringe plunger flange holder 1318 and the syringe plunger 1304 can be configured to move or translate relative to the syringe barrel 1306, which can be fixedly and releasably held by a separate housing of the fluid reservoir interface 1340, such as a syringe barrel flange holder 1324. The syringe plunger 1304 and the syringe barrel 1306 can each be releasable from their respective housings, e.g., manually by a user or via mechanical movement of the respective housings, a spring, or other component within the fluid flow control device 1300.

The indicator viewing window 1308 can be an example of an interface for presenting information to a user. For example, the indicator viewing window 1308 can be configured to display information regarding an operation or state of the fluid flow control device, such as a status of a sterilization, a power source (e.g., battery) in the fluid flow control device, etc. For instance, the indicator viewing window 130 may present warnings and/or alerts to the user, including an indication that the sterilization fluid injector may be properly or improperly engaged with the sterilization fluid reservoir.

Figure 14A:
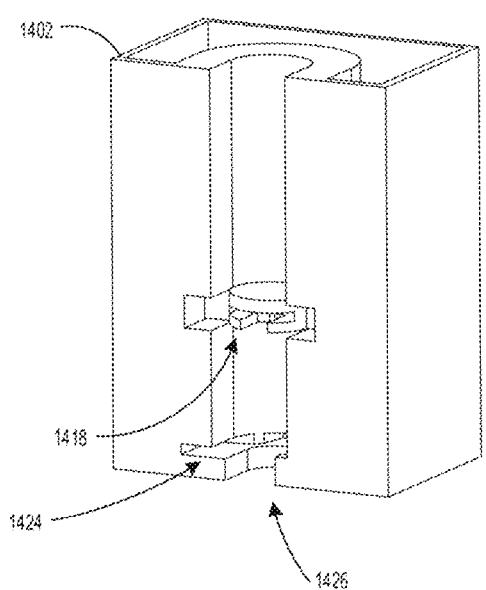
FIG. 14A and FIG. 14B are illustrations of various aspects of a fluid flow control device and a fluid reservoir, according to embodiments of the present disclosure.
Figure 14B:
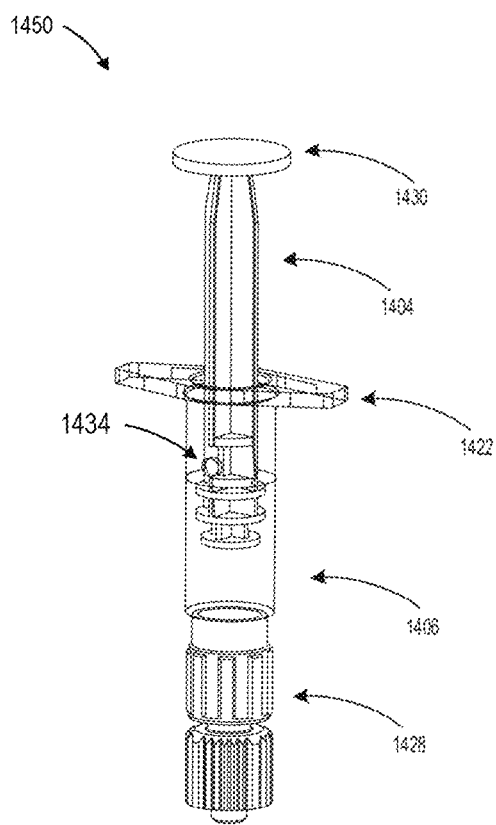
Figure 14C:
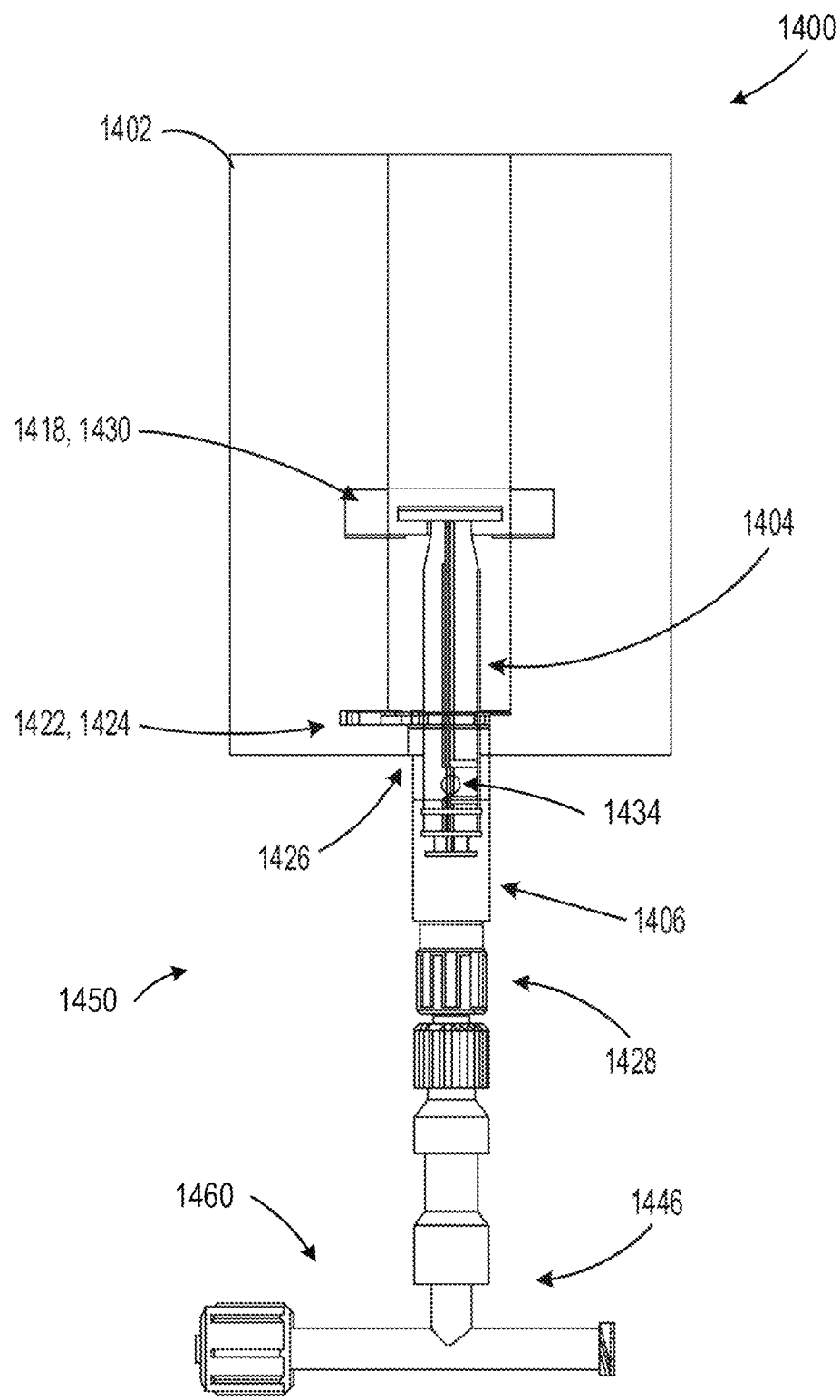
FIG. 14C is an illustration of an aspect of a fluid flow control device and a fluid reservoir in connection with a connector, according to embodiments of the present disclosure.

FIG. 14A through FIG. 14C provide illustrations of components of an example fluid flow control device and a fluid reservoir implemented as a modified syringe, according to embodiments. The fluid flow control device and the fluid reservoir can include components that are structurally and/or functionally similar to that of other fluid flow control devices and/or fluid reservoirs described herein, respectively.

FIG. 14A illustrates a housing 1402 of a fluid flow control device, a syringe plunger flange holder 1418 of an actuation system of the housing 1402, and a syringe barrel flange holder 1424 adjacent an opening or port 1426 of the housing 1402.

FIG. 14B provides an illustration of a modified syringe, wherein the modified syringe is configured to confine linear motion and rotation motion of the syringe plunger and the syringe barrel according to a position of a locking element and a locking port. A syringe plunger 1404 of FIG. 14B includes a syringe plunger flange 1430 coupleable with the syringe plunger flange holder 1418 of FIG. 14A. A syringe barrel 1406 of FIG. 14B includes a syringe barrel flange 1422 coupleable to the syringe barrel flange holder 1424 of FIG. 14A. To permit fluid communication with a connector, as described in the present disclosure, the syringe barrel 1406 may be coupleable to a fitting 1428. The fitting 1428 may be one that is coupleable to the syringe barrel 1406 while being sized to pass through the opening or port 1426 of the housing 1402 of FIG. 14A. In certain embodiments, the fitting 1428 may be a Luer fitting or similar fitting. In some embodiments, the fitting 1428 may be a rotating fitting.

In an embodiment, and as will be described later, FIG. 14B includes an illustration of an opening 1434 within the syringe barrel 1406 through which a locking element may extend to control rotation and translation of the syringe plunger 1404 within the syringe barrel 1406. Further description of the locking and unlocking nature of a fluid reservoir 1450, including a description of pathways of the syringe plunger 1404, follows with reference to subsequent figures.

FIG. 14C illustrates a fluid flow control device 1400 of the present disclosure in fluid communication with a connector 1460 of the present disclosure. The connector 1460 may be coupleable to a fitting 1428 coupleable to a syringe barrel 1406 of a fluid reservoir 1450. A syringe barrel flange 1422 of the syringe barrel 1406 may be coupleable to a syringe barrel flange holder 1424 of a housing 1402 of the fluid flow control device 1400. The syringe barrel 1406, by having the syringe barrel flange 1402 within the syringe barrel flange holder 1424, is constrained from linear translation and/or rotation movement. The syringe barrel 1406 extends through an opening or port 1426 of the housing 1402. The syringe barrel 1406 includes an opening 1434 through which a locking element, described with respect to FIG. 15A through FIG. 15C, can extend. The syringe barrel 1406 may have a syringe plunger 1404 disposed therein. A syringe plunger flange 1418 of the syringe plunger 1404 may be coupleable to a syringe plunger flange holder 1430 of the housing 1402. The syringe plunger flange holder 1430 may be a component of an actuation system of the fluid flow control device 1400 and, while preventing rotational motion of the syringe plunger 1404, translates translation motion to the syringe plunger 1404 when the locking element is within a longitudinal channel of the syringe plunger 1404. Such a configuration will be described later, but it should be appreciated that, when syringe barrel 1406 is rotated from a first position to a second position, the locking element moves from within a first channel or cavity of the syringe plunger 1404 into a second channel or longitudinal slot of the syringe plunger 1404 (e.g., the longitudinal channel of the syringe plunger), and the syringe plunger 1404 is able to translate into the syringe barrel 1406 via motion of the actuation system.

The locking element described above will now be detailed in view of the fluid reservoir shown in FIG. 15A through FIG. 15C.

In embodiments, the locking element allows the fluid reservoir to be in either of an inoperable state (e.g., locked state) or an operable state (e.g., unlocked or translatable state), improving safety and control over the sterilization process. Such can avoid, for example, accidental deployment of the sterilization fluid during transit or pre-injection manipulation by a user. To this end, a syringe plunger 1504 may include a syringe plunger flange 1524 opposite a syringe plunger sealing end 1554. A length therebetween may define a longitudinal axis 1530 of the syringe plunger 1504. In embodiments, a locking element 1532 may include a locking element base 1560 and a locking element pillar or projection 1542. The locking element 1532 may be configured such that the locking element pillar 1542 can pass through an opening 1534 of a syringe barrel 1506 and reside within a circumferential channel 1538 (or a cavity or other laterally or circumferentially extending groove) of the syringe plunger 1504, when the locking element pillar 1542 is in a first position. A concave surface of the locking element base 1560 may be coupleable to a convex, outer surface of the syringe barrel 1506. In some embodiments, the base 1560 can be configured to have a small profile, e.g., such that the base 1560 does not interfere with an operation of the plunger 1504 or other components of the fluid reservoir and/or a fluid flow control device. In some embodiments, the locking element 1532 is formed integrally with the syringe barrel 1506 during fabrication and is then assembled with the syringe plunger 1504.

When the fluid reservoir is first interfaced with a fluid reservoir interface of a fluid flow control device, the locking element pillar 1542 of the locking element 1532 may be positioned through the opening 1534 of the syringe barrel 1506 and within the circumferential channel 1538 of the syringe plunger 1504. When the locking element pillar 1542 is within the circumferential channel 1538 at a first position (e.g., a locked position or an inoperable position), the syringe plunger 1504 is prevented from linear translation along the longitudinal axis 1530 of the syringe plunger 1504, with the locking element pillar 1542 being constrained between walls of the circumferential channel 1538. Upon rotation of the syringe barrel 1506, such that the locking element pillar 1542 is rotated through an opening 1536 of a longitudinal fin or ridge 1573 of the syringe plunger 1504, the locking element pillar 1542 may be within a longitudinal channel 1540 of the syringe plunger 1504 at a second position (e.g., an unlocked position or an operable position), with the syringe plunger 1504 being allowed to translate along the longitudinal axis 1530. In the second position, the syringe plunger 1504, in coordination with a syringe plunger flange holder of an actuation system, can be translated according to processes described herein for the injection and retraction of sterilization fluid to and from a connector and peritoneal dialysis tubing of a peritoneal dialysis system.

Figure 16A:
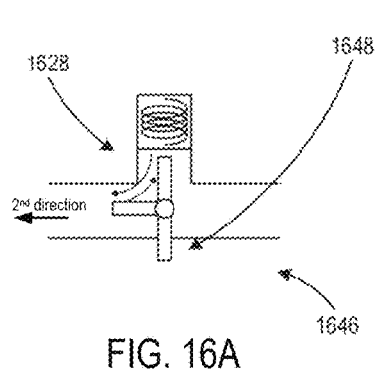
FIG. 16A, FIG. 16B, and FIG. 16C are schematic diagrams of a flow control insert or mechanism in different orientations, according to embodiments of the present disclosure.
Figure 16B:
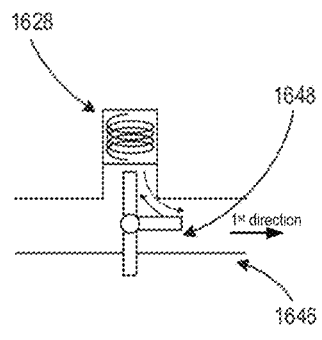
Figure 16C:
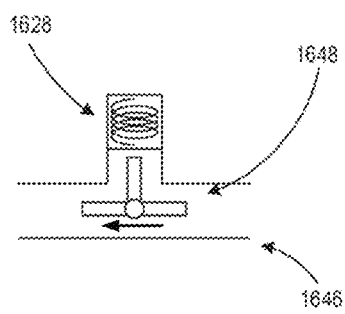

FIG. 16A through FIG. 16C illustrate an implementation of a flow diverter within a connector as a mechanism for controlling fluid flow within the connector, according to example embodiments. FIG. 16A illustrates a stopcock as a flow diverter 1648 within a connector 1646. The connector 1646 can be structurally and/or functionally similar to other connectors described herein, including, for example, connector 760. The connector 1646 may be connected to a fluid reservoir via a fitting 1628, which may be a Luer fitting or other type of coupler, as previously described. In embodiments, the stopcock may be a 3-way stopcock, a 4-way stopcock, and the like.

In embodiments, the stopcock may be set to a first configuration, in which the stopcock is configured to block fluid flow in a first direction of the connector 1646, so that sterilization fluid from the fluid reservoir can flow through the fitting 1628 and in a second direction of the connector 1646. After a predetermined period of time, or a dwell time of the sterilization fluid within that side of the connector 1646 and peritoneal dialysis tubing connected therewith, retraction of at least a substantial majority of the sterilization fluid out of that side of the connector 1646 and the peritoneal dialysis tubing connected therewith may be actuated. The stopcock may then be set to a second configuration, as shown in FIG. 16B, in which the stopcock is configured to block fluid flow in the second direction of the connector 1646, so that sterilization fluid from the fluid reservoir flows through the fitting 1628 in the first direction of the connector 1646. Again, after a predetermined period of time, or a dwell time of the sterilization fluid within that side of the connector 1646 and the peritoneal dialysis tubing connected therewith, retraction of at least a substantial majority of the sterilization fluid out of that side of the connector 1646 and out of the peritoneal dialysis tubing connected therewith may be actuated. After retraction of at least a substantial majority of the sterilization fluid from the connector 1646, the stopcock can be set to a third configuration, in which the stopcock is configured to open fluid flow in both the first direction and the second direction, thus allowing dialysis solutions to be flowed through the peritoneal dialysis tubing via the connector 1646, and the fluid reservoir (and fluid flow control device coupled thereto) can be disconnected from the fitting 1628 of the fluid reservoir. In some embodiments, the third configuration of the stopcock may be one that blocks the opening and/or port through which the sterilization fluid was provided, the opening and/or port being orthogonal to an axis defined by the first direction and the second direction, the blocking of the opening and/or port preventing contamination of the connector and fluid leakage during peritoneal dialysis. Such a third configuration may be realized by rotating the stopcock such that the opening and/or port is blocked and fluid flows freely through the stopcock and in the first direction and the second direction.

In some embodiments, the stopcock can be manually set to the first, second, and third configurations. In some embodiments, an external device (such as, for example, the fluid flow control device) can include an actuator (e.g., mechanically and/or electrically driven actuator) that can move the stopcock to the first, second, and third configurations. For instance, a stopcock actuator of the sterilization fluid injector 140 shown in FIG. 24A can be used to move the stopcock between the first, second, and third configurations in a controlled manner. In such embodiments, the actuator for moving the stopcock can be controlled, e.g., via an onboard processor of the external device and/or a remote processor operatively coupled to the actuator. In such embodiments, the stopcock may be designed to prevent a user from controlling the configuration (e.g., requiring a high force to turn the stopcock knob or making the stopcock knob physically inaccessible to the user).

In some embodiments, the stopcock may have an aperture, or bore, therein sized according to the dialysis application and dialysis equipment at hand. For instance, the aperture may be large enough to allow dialysate to freely flow through the connector when the stopcock is in the third configuration, as described in the preceding paragraphs, but must be able to be fabricated and must be based on a size of the connector and the peritoneal dialysis tubing.

Figure 17:
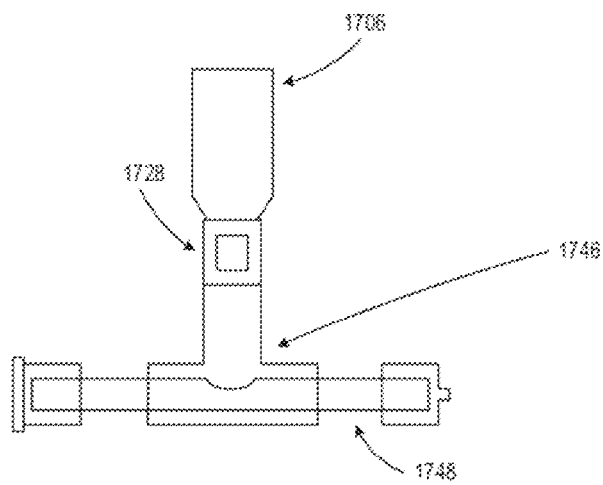
FIG. 17 is a schematic diagram of a flexible flow control insert, according to embodiments of the present disclosure.

Referring now to FIG. 17, an example connector 1746 including flexible parts 1748 implemented as flexible tubing or membrane is described. The connector 1746 can be structurally and/or functionally similar to other connectors described herein, including, for example, connector 760. The connector 1746 may be fluidically coupled to a fluid reservoir 1706 via a fitting 1728. The flexible parts 1748, as described previously with reference to FIG. 7, allows for selective opening of first and second sides of the connector 1748, e.g., to accommodate mismatched pressures or air volumes within different sections of peritoneal dialysis tubing. For instance, when attempting to simultaneously provide sterilization fluid to each of a first side of the connector 1746 and to a second side of the connector 1746, the first side and the second side being fluidically coupled, a difference in line pressure or air volumes between a transfer set connected to a patient and a cassette tubing connected to, for instance, a dialysis cycler, can result in uneven sterilization of the components. Thus, the flexible parts 1748 of the connector 1746 of FIG. 17 allows for temporary, controlled sealing of the respective sides of the connector 1746 so that sterilization fluid can be reliably provided to the other side of the connector 1746.

In embodiments, the fitting 1728 of the connector 1746 may be a flexible membrane that, like the flexible parts, can be dynamically dilated and constricted in order to control flow from the fluid reservoir into the connector 1746.

In embodiments, the flexible membrane and flexible parts 1748 may be controlled by a fluid flow control element of a fluid flow control device, as described above with reference to FIG. 7. To this end, the control may be to engage a clamp around the circumference of the flexible membrane and the flexible parts 1748, or to otherwise engage a mechanism by which the various lumens or channels of the connector 1746 can be constricted or blocked.

A visual flow diagram of implementation of the flexible parts 1748 of FIG. 17 is shown in FIG. 18A through FIG. 18F.

In embodiments, the connector may include a first flexible part 1848a and a second flexible part 1848b. In a first configuration, as in FIG. 18A, the first flexible part 1848a may be fully constricted so that sterilization fluid from a fluid reservoir 1806 may flow through a flexible membrane 1820 and in a second direction of the connector 1846 via the second flexible part 1848b, which can be open or dilated.

In some embodiments, the fluid reservoir 1806 may be within a housing of a fluid flow control device 1800, which may include a processor to control the patency or state of a lumen or channel of the first flexible part 1848a and the second flexible part 1848b. Alternatively, the fluid reservoir 1806 can be separate from but coupleable to the fluid flow control device 1800. The fluid reservoir 1806 can be structurally and/or functionally similar to other fluid reservoirs described herein. The fluid flow control device 1800 can be structurally and/or functionally similar to other fluid flow control devices described herein, and therefore, can contain one or more components that are described with respect to those other fluid flow control devices, even though such components are not depicted in FIGS. 18A-18F. After a predetermined period of time, or a dwell time of the sterilization fluid within the second side of the connector 1846 and a side of the peritoneal dialysis tubing connected to the second side of the connector 1846, retraction of at least a substantial majority of the sterilization fluid out of the second side of the connector 1846 and out of the connected peritoneal dialysis tubing may be actuated. The flexible part may then be set to a second configuration, as shown in FIG. 18B, wherein the first flexible part 1848a is open and the second flexible part 1848b is closed or constricted. This allows sterilization fluid from the fluid reservoir 1806 to flow through the flexible membrane 1820 in a first direction of the connector 1846 to the first side of the connector 1846. Again, after a predetermined period of time, or a dwell time of the sterilization fluid within the first side of the connector 1846 and a side of the peritoneal dialysis tubing connected thereto, retraction of at least a substantial majority of the sterilization fluid out of the first side of the connector 1846 and out of the connected peritoneal dialysis tubing may be actuated.

In embodiments, the flexible membrane 1820 may be controlled in a similar manner to the first flexible part 1848a and the second flexible part 1848b. When the flexible parts 1848a, 1848b are in the first configuration and in the second configuration (and selectively being used to direct fluid flow in the first or second directions), the flexible membrane 1820 can be open or dilated, e.g., to allow sterilization fluid to flow into the connector and to be retracted from the connector. In some embodiments, the flexible membrane 1820 can be fully dilated during injection and/or retraction of the sterilization fluid. Alternatively, the flexible member 1820 can be set to varying degree of dilation, e.g., to control fluid flow rate of the sterilization fluid. After retraction of at least a substantial majority of the sterilization fluid from the connector 1846, the flexible membrane 1820 and the flexible parts 1848a, 1848b can be set to a third configuration, as shown in FIG. 18C, wherein the first flexible part 1848a and the second flexible part 1848b are open and the flexible membrane 1820 is fully constricted, to allow dialysis solutions to be flowed through the peritoneal dialysis tubing via the connector 1846, without having sterilization fluid and/or contaminants leaking into the connector 1846.

Figure 18A:
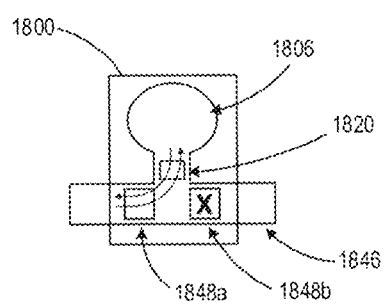
FIG. 18A, FIG. 18B, FIG. 18C, FIG. 18D, FIG. 18E, and FIG. 18F are schematic diagrams of flow control inserts in different states, according to embodiments of the present disclosure.
Figure 18B:
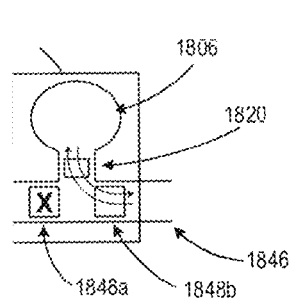
Figure 18C:
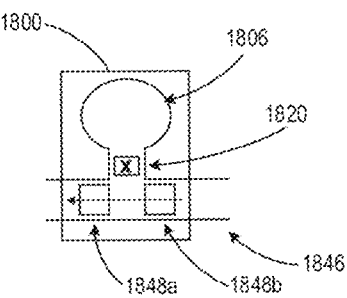
Figure 18D:
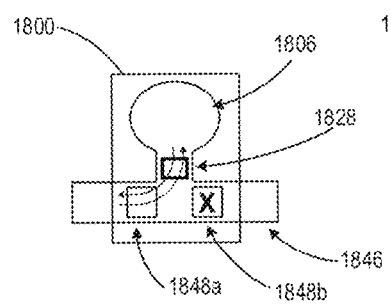
Figure 18E:
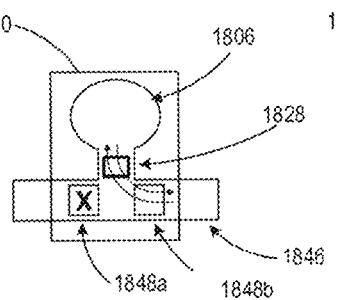
Figure 18F:
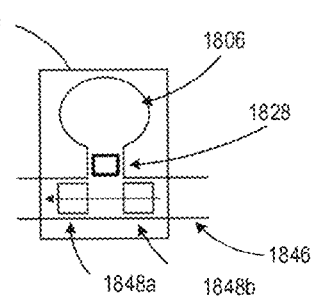

Similarly, with reference to FIG. 18D through FIG. 18F, the connector 1846 may include a first flexible part 1848a and a second flexible part 1848b. In a first configuration, as in FIG. 18D, the first flexible part 1848a may be fully constricted so that sterilization fluid from the fluid reservoir 1806 may flow through a fitting 1828 and in a second direction of the connector 1846 via the second flexible part 1848b, which is open. After a predetermined period of time, or a dwell time of the sterilization fluid within the second side of the connector 1846 and a side of the peritoneal dialysis tubing connected therewith, retraction of at least a substantial majority of the sterilization fluid out of the second side of the connector 1846 and out of the connected peritoneal dialysis tubing may be actuated. The flexible parts may then be set to a second configuration, as shown in FIG. 18B, wherein the first flexible part 1848a is fully constricted and the second flexible part 1848b is open. This allows sterilization fluid from the fluid reservoir 1806 to flow through the fitting 1828 in the first direction of the connector 1846. Again, after a predetermined period of time, or a dwell time of the sterilization fluid within the first side of the connector 1846 and a side of the peritoneal dialysis tubing connected therewith, retraction of at least a substantial majority of the sterilization fluid out of the first side of the connector 1846 and out of the connected peritoneal dialysis tubing may be actuated. After retraction of at least a substantial majority of the sterilization fluid from the connector 1846, the flexible parts can be set to a third configuration, wherein the first flexible part 1848a and the second flexible part 1848b are open, to allow dialysis solutions to be flowed through the peritoneal dialysis tubing via the connector 1846.

In embodiments, the fitting 1828 may be a Luer fitting and may be activated in order to allow or disallow flow. For instance, in the first configuration and the second configuration, the fitting 1828 may be in an open position to allow sterilization fluid to flow from the fluid reservoir 1828 to the connector 1846. In the third configuration, however, the fitting 1828 may be in a closed position to prevent dialysate from traveling into the fluid reservoir 1828. Moreover, this permits the fluid reservoir and fluid flow control device, at large, to be optionally removed from the connector 1846 during performance of the peritoneal dialysis.

While the fluid reservoir 1806 is schematically depicted in FIGS. 18A-18C as being contained together with components of the connector 1846 within a fluid flow control device 1800, it can be appreciated that, in some embodiments, the fluid flow control device 1800 is separate from the fluid reservoir 1806 and/or connector 1846, but that all three components can be configured to releasably couple to one another to form a system for sterilization, and that in other embodiments, the fluid flow control device 1800, fluid reservoir 1806, and/or connector 1846 can be a unitary or integrated device that includes the respective components of each.

Figure 19A:
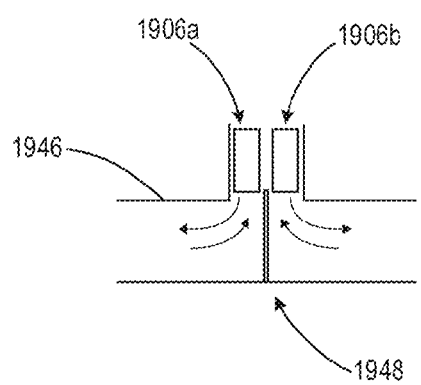
FIG. 19A and FIG. 19B are schematic diagrams of aspects of a flow control insert, according to embodiments of the present disclosure.
Figure 19B:
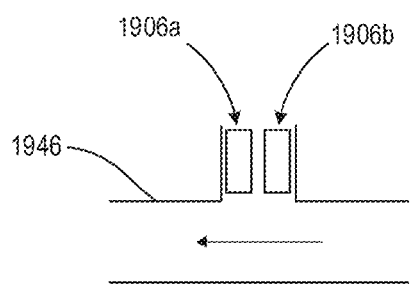

With reference now to FIG. 19A and FIG. 19B, and in view of the flow described with reference to FIG. 9, directional sterilization may also be performed simultaneously. In this instance, two separate fluid reservoirs may be used in order to permit controlled flow of sterilization fluid into a first side and a second side of the connector. Each fluid reservoir can be structurally and/or functionally similar to each other and to other fluid reservoirs described herein. With utilization of a flow diverter in a proper configuration, two separate fluid flow paths can be established to sterilize each side of the connector and the peritoneal dialysis tubing.

In particular, a flow diverter 1948 of a connector 1946 can be set to a first configuration so that sterilization fluid from a first fluid reservoir 1906a on a first side and from a second fluid reservoir 1906b on a second side is permitted to flow to respective sides of the connector 1946, as shown in FIG. 19A, with the sides of the connector 1946 being fluidically separated or isolated from one another by the flow diverter 1948. The connector including the fluid diverter 1948 can be structurally and/or functionally similar to other connectors (and their components) described herein, including the connector described with reference to FIG. 7.

In this instance, the flow diverter 1948 is implemented as a barrier or other device that, in the first configuration, is set to prevent fluid flow between a first side of the connector 1948 and a second side of the connector 1948, thereby establishing two separate fluid flow paths. After injection of the sterilization fluid and after a predetermined period of time, or a dwell time of the sterilization fluid within the first side of the connector 1948 and a first tube of the peritoneal dialysis tubing and the second side of the connector 1948 and a second tube of the peritoneal dialysis tubing, retraction of at least a substantial majority of the sterilization fluid is actuated. As shown in FIG. FIG. 19B, after retraction of at least a substantial majority of the sterilization fluid from the connector 1948, the flow diverter 1948 may be set to a second configuration wherein the barrier is removed and fluid flow between the first side of the connector 1946 and the second side of the connector 1946 is restored, thereby allowing dialysis solutions to be flowed through the peritoneal dialysis tubing via the connector 1946. The flow diverter 1948 can be transitioned between the first and second configurations, e.g., via sliding the flow diverter 1948. In some embodiments, an external device (such as, for example, the fluid flow control device) can include an actuator (e.g., mechanically and/or electrically driven actuator) that can move the flow diverter 1948 to the first and second configurations. In such embodiments, the actuator for moving the flow diverter 1948 can be controlled, e.g., via an onboard processor of the external device and/or a remote processor operatively coupled to the actuator.

Figure 20:
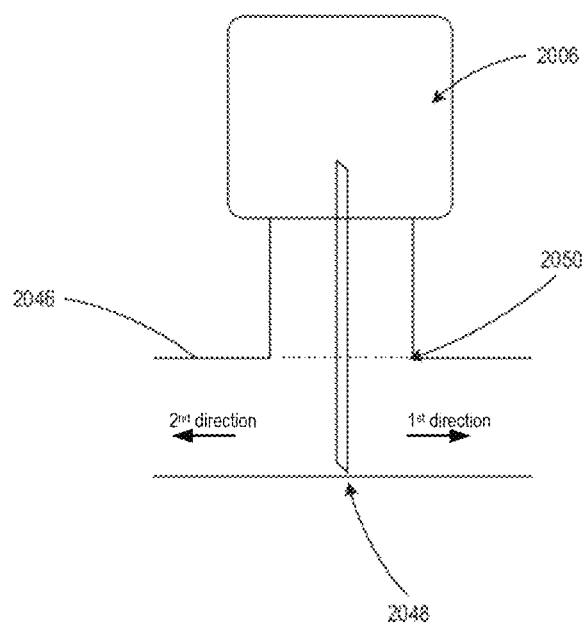
FIG. 20 is a schematic diagram of aspects of a flow control insert, according to embodiments of the present disclosure.

Further to the above, and with reference now to FIG. 20, directional sterilization may be performed simultaneously, wherein a connector 2046 includes a flow diverter 2048 and a septum 2050. The connector including the fluid diverter 2048 can be structurally and/or functionally similar to other connectors (and their components) described herein, including the connector described with reference to FIG. 7.

In this instance, the flow diverter can be implemented as a puncturing or piercing device. The flow diverter 2048 can be configured to pierce the septum 2050 when moved to a first configuration, and can be arranged so as to provide sterilization fluid from a fluid reservoir 2006 through the flow diverter 2048 and in a first direction of the connector 2046 and in a second direction of the connector 2046, separately, while the flow diverter 2048 is in the first configuration. In some embodiments, the flow diverter 2048 can divide a pre-existing channel into two fluid channels or passageways. Alternatively, the fluid diverter 2048 can be implemented as a multi-lumen needle that can provide separate flow, via two separate lumens, into the first and second sides of the connector 2046. Accordingly, sterilization fluid may flow to both sides of the connector 2046, while the sides of the connector 2046 are fluidically separated from each other by the flow diverter 2048. In this instance, the flow diverter 2048 may be a needle, a needle-like device, a plate or flat barrier with a sharpened edge, or other similar device that acts as a barrier while allowing fluid flow therefrom and in different directions. In embodiments, the septum 2050 may be a polytetrafluoroethylene and silicone septum or similar composition.

After delivery of the sterilization fluid and after a predetermined period of time, or a dwell time of the sterilization fluid within the first side of the connector 2048 and a first portion of the peritoneal dialysis tubing and the second side of the connector 2048 and a second portion of the peritoneal dialysis tubing, retraction of at least a substantial majority of the sterilization fluid is actuated. After retraction of at least a substantial majority of the sterilization fluid from the connector 2048, the flow diverter 2048 may be set to a second configuration wherein the needle or needle-like device is retracted through the septum 2050, the septum 2050 restores a seal between the fluid reservoir 2006 and the connector 2048, and fluid flow between the first side of the connector 2046 and the second side of the connector 2046 is restored, thereby allowing dialysis solutions to be flowed through the peritoneal dialysis tubing via the connector 2046.

Figure 21A:
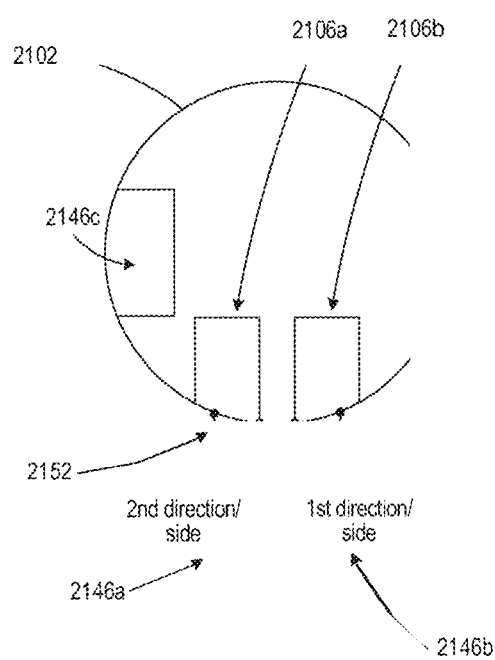
FIG. 21A and FIG. 21B are schematic diagrams of aspects of a rotary flow control mechanism, according to embodiments of the present disclosure.
Figure 21B:
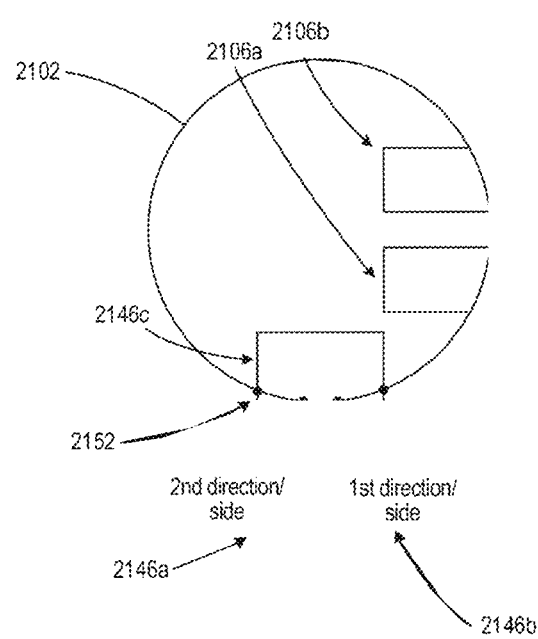

Referring now to FIG. 21A and FIG. 21B, an alternative connector is described in view of simultaneous, directional sterilization of sides of a connector 2146 and adjacent peritoneal dialysis tubing. The connector 2146 can include components that are functionally and/or structurally similar to that of other connectors described herein, including, for example, the connector described with reference to FIG. 7. As shown in FIG. 21A and FIG. 21B, a housing 2102 of a fluid flow control device may include or be coupleable to a first fluid reservoir 2106a, a second fluid reservoir 2106b, and a connector component 2146c. In embodiments, the first fluid reservoir 2106, the second fluid reservoir 2106b, and the connector component 2146c may be coupleable to the connector component 2146a, 2146b via a docking mechanism 2152 that ensures alignment and secures of the corresponding components of the housing 2102 and the connector 2146. The connector component 2146c can include or define a fluid passageway. The housing 2102 may be rotatable so as to, when in a first configuration, bring the first fluid reservoir 2106a and the second fluid reservoir 2106b into fluidic communication with respective sides 2146a, 2146b of the connector 2146, and, when in a second configuration, bring the connector component 2146c into fluidic communication with the first and second sides of the connector. Such configurations are shown in FIG. 21A and FIG. 21B, respectively.

In this way, when the first fluid reservoir 2106a and the second fluid reservoir 2106b are in the first configuration and in fluidic communication with respective sides of the connector, sterilization fluid can be flowed into a first side 2146a of the connector 2146 (and into a first portion of peritoneal dialysis tubing) and into a second side 2146b of the connector 2146 (and into a second portion of the peritoneal dialysis tubing) to sterilize the components simultaneously. As can be appreciated from FIG. 21A and FIG. 21B, the first side and the second side of the connector 2146 are not fluidically coupled in the first configuration of the housing 2102. However, after a predetermined period of time has passed, the sterilization fluid can be retracted from the first side and the second side of the connector 2146 and, after the substantial majority of the sterilization fluid is removed, the housing 2102 can be rotated in order to bring the connector component 2146c into fluidic communication with the first and second sides 2146a, 2146b of the connector. In this way, and as shown in FIG. 21B, the connector component 2146c brings the two sides of the connector into fluidic communication so that peritoneal dialysis can be performed.

In embodiments, movement of the housing 2102 can be controlled by the fluid flow control device, e.g., via mechanical and/or electrical mechanisms, as would be appreciated in view of the disclosure.

Figure 22:
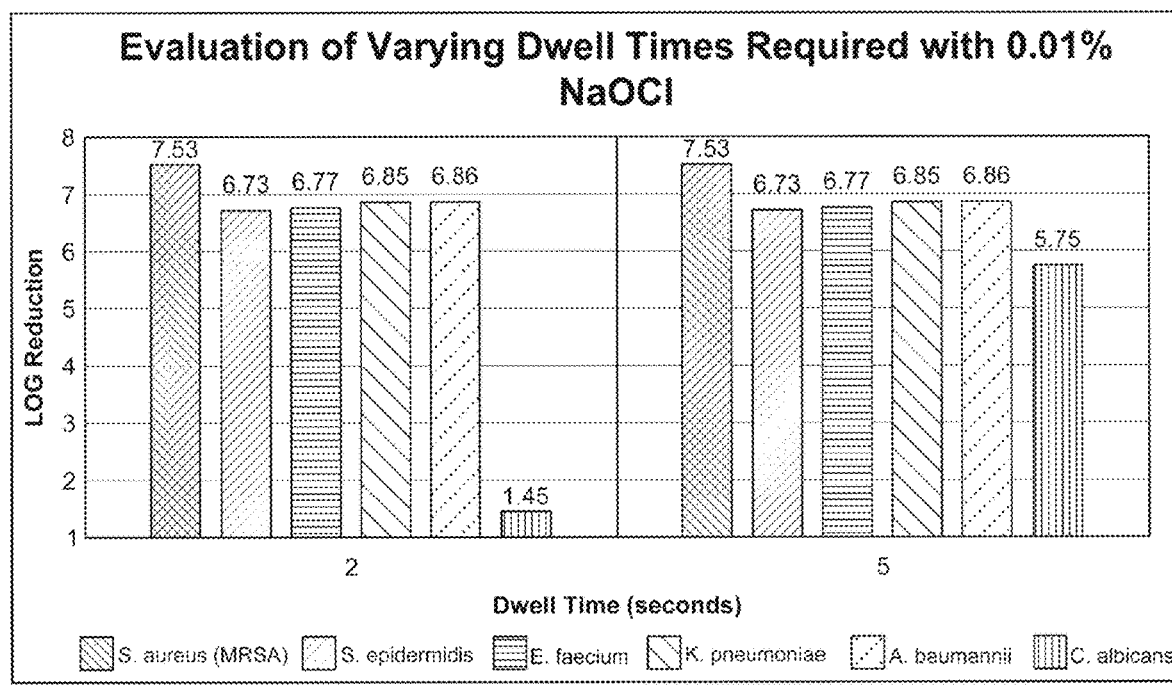
FIG. 22 is a plot showing an evaluation of a log reduction in microbial units with different dwell times of a sterilization fluid, according to embodiments of the present disclosure.

FIG. 22 is a graphical illustration of experimental data evaluating the impact of varying time scales of dwell time on the effectiveness of sterilization fluid in removing contamination from the sterilizable connector. The experiment was performed without fluid in the sterilizable connector prior to sterilization. A media containing specific microbes and sterilization fluid were combined and the antimicrobial effect of the sterilization fluid after a particular dwell time was evaluated. For instance, at five seconds of dwell time (i.e., the predetermined period of time), evaluated contaminants including *S. aureus* (MRSA), *S. epidermidis, E. faecium, K. pneumoniae, A. baumannii*, and *C. albicans* were reduced with a greater than 5-log reduction in microbial units, from baseline at time zero vs. when exposed to 0.01% sodium hypochlorite (NaOCl). At 2 second of dwell time, evaluated contaminants including *S. aureus* (MRSA), *S. epidermidis, E. faecium, K pneumoniae*, and *A. baumannii* were reduced with a greater than 5-log reduction in microbial units, from baseline at time zero vs. when exposed to 0.01% sodium hypochlorite (NaOCl). While the reduction in *C. albicans* did not have greater than a 5-log reduction in microbial units, it can be appreciated that both a dwell time of 2 seconds and a dwell time of 5 second can produce significant microbial reduction and therefore a risk of complications from using peritoneal dialysis.

In another example, wherein dialysis fluid is within the sterilizable connector and the transfer set prior to sterilization, a 30 second dwell time of 0.55% sodium hypochlorite (NaOCl) was evaluated to determine the ability of sterilization fluid to sterilize the transfer set and the remaining peritoneal dialysis tubing. Sterilization efficiency was reported as a log 10 reduction of microbial colony forming units/device of the test arm compared to the positive control. Average log reductions observed include >7.12 for *S. epidermidis* and >7.44 for *P. aeruginosa*.

Figure 23:
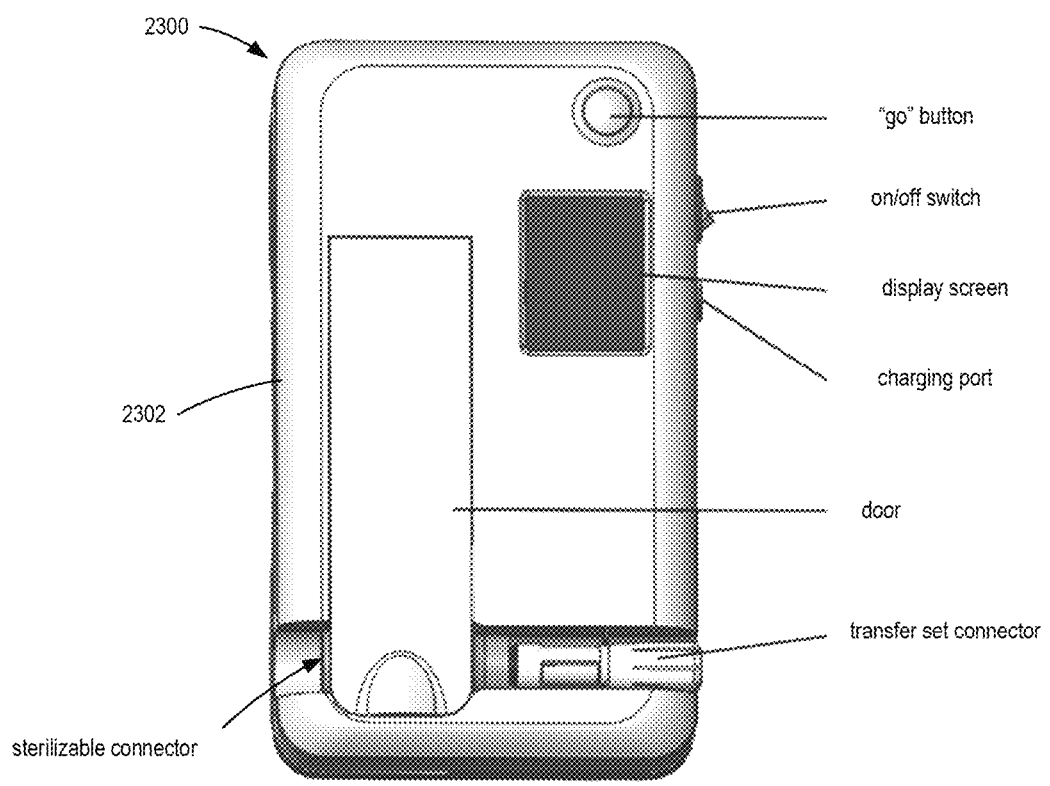
FIG. 23 is a rendering of a fluid flow control device, according to embodiments of the present disclosure.

FIG. 23 is a rendering of a fluid flow control device, according to embodiments of the present disclosure. In particular, FIG. 23 is a rendering of an exemplary fluid flow control device 2300 having a cavity for receiving each of a sterilizable connector, a fluid reservoir, and portions of peritoneal dialysis tubing (such as a transfer set connector). Moreover, as was described above and as will be described below, the fluid flow control device 2300 includes actuation elements configured to control the dispensing element and/or the sterilizable connector. Additional aspects of the fluid flow control device 2300 not described below can be assumed to be similar to those described with reference to any of the preceding Figures.

The fluid flow control device 2300 can include components that are structurally and/or functionally similar to like components of other devices described herein, including, for example, sterilizable connectors (e.g., sterilizable connector 110), injectors, etc. In an embodiment, fluid flow control device 2300 may include a housing 2302. The housing 2302 may include an actuation system operatively coupled to a drive mechanism and a cavity comprising a fluid reservoir interface for receiving a fluid reservoir and a channel for receiving a sterilizable connector and aspects of peritoneal dialysis tubing and connectors. The drive mechanism may be operatively coupled to a controller. A power source, which may be a rechargeable battery pack accessible by a charging port, may be connected to any module or component within the housing 2302. For instance, the power source may be directly connected to the controller, to the drive mechanism, to the actuation system, and/or to the fluid reservoir interface. In one instance, the power source is directly connected to the controller, which subsequently provides power to the drive mechanism, which is operatively coupled to the fluid reservoir interface via the actuation system. Power can be supplied to the modules or components within the housing 2302 by user interaction with an on/off switch disposed within a wall of the housing 2302. In some embodiments, the fluid flow control device 2300 can include a cover configured to transition between first and second configurations (e.g., open and closed configurations) to provide access to the fluid reservoir interface and the channel. The fluid reservoir interface and the channel can be substantially within the housing 2302, or at least components thereof can be enclosed by the housing 2302 and/or the cover. The fluid reservoir interface, which is covered by the door of FIG. 23, is couplable to the sterilizable connector. The housing 2302 may further comprise a "go" button which controls initialization of a sterilization protocol, an on/off switch which controls power to the modules or components within the housing 2302, and a display screen for communicating with the user, among other features.

In an embodiment, the controller may be activated or deactivated by user interaction with the "go" button shown in FIG. 23. The "go" button is optional, but when present, can be situated on or within a wall of the housing 2302. The "go" button may be a pushbutton switch, a pressure switch, a temperature switch, a limit switch, a joystick switch, a toggle switch, a rotary switch, a translating switch or slider, a touchscreen interface, and the like.

The processes and logic flows described herein can be performed by one or more programmable computers executing one or more computer programs to perform one or more functions of the fluid flow control device. The processes and logic flows can also be performed by, and can also be implemented as, special purpose logic circuitry, e.g., an FPGA (field programmable gate array) or an ASIC (application-specific integrated circuit).

Compute devices, which may be generally referred to herein as a compute device or controller, suitable for the execution of a computer program include, by way of example, general or special purpose microprocessors or both, or any other kind of central processing unit. Generally, a central processing unit will receive instructions and data from a read-only memory or a random access memory or both. Elements of a compute device include a central processing unit for performing or executing instructions and one or more memory devices for storing instructions and data. Generally, a compute device can also include, or be operatively coupled to receive data from or transfer data to, or both, one or more mass storage devices for storing data, e.g., magnetic, magneto-optical disks, or optical disks. However, a compute device need not have such devices. Moreover, a compute device can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

Figure 24A:
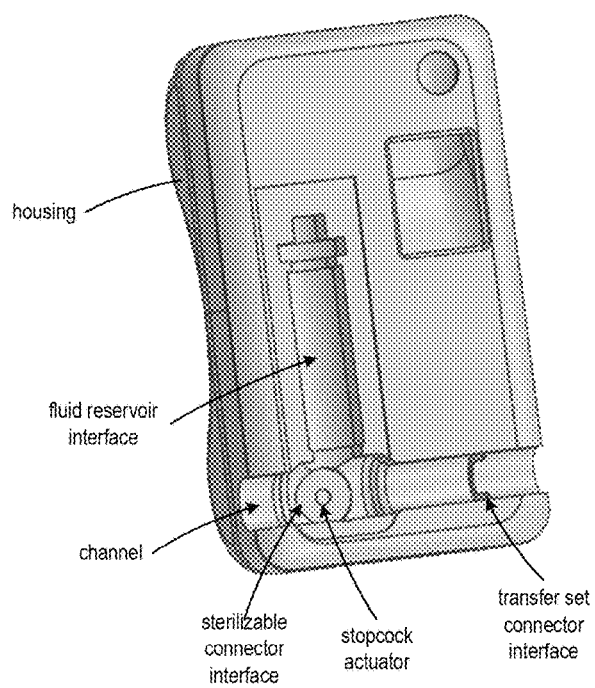
FIG. 24A is a rendering of a fluid flow control device, according to embodiments of the present disclosure.
Figure 24B:
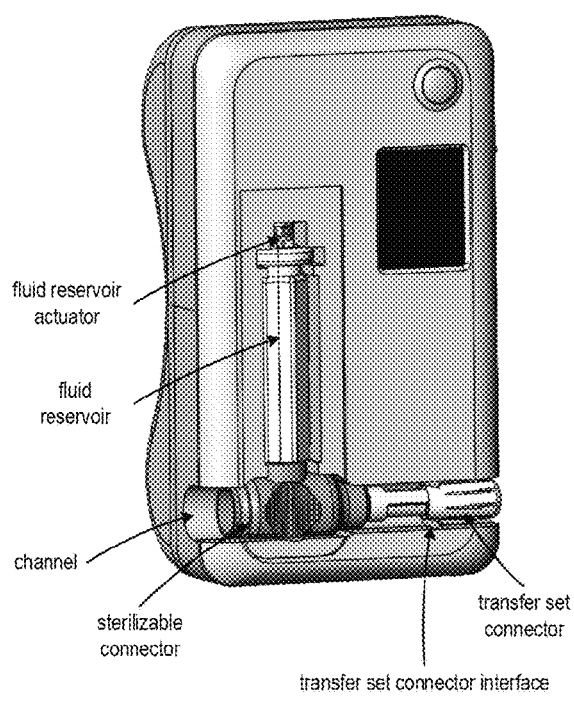
FIG. 24B is a rendering of a fluid flow control device with a sterilizable connector coupled thereto, according to embodiments of the present disclosure.

In an embodiment, the actuation system may include one or more actuators. In embodiments, the actuator may include one or more of a linear actuator, a rotary actuator, hydraulic actuator, pneumatic actuator, electric actuator, thermal and magnetic actuator, mechanical actuator, supercoiled polymer actuators, a diaphragm-assisted actuator, and the like. With reference to FIG. 24A and FIG. 24B, and when the fluid reservoir includes a syringe assembly, the one or more actuators may include a fluid reservoir actuator configured to control a position of a syringe plunger within a syringe and a stopcock actuator configured to control a position of a valve within a stopcock of the sterilizable connector to direct fluid flow through a sterilizable connector. The fluid reservoir actuator may be similar to those described previously herein. As shown in FIG. 24A, the stopcock actuator may be within a sterilizable connector interface defined by a recess configured to receive the sterilizable connector. For instance, the sterilizable connector may include a hexagonally shaped projection configured to fit within the stopcock actuator, which is a hexagonally shaped recess within the sterilizable connector interface and shaped as an inverse of the hexagonally shaped projection. In this way, the stopcock of the sterilizable connector can be controlled by actuation of the stopcock actuator. The sterilizable connector interface may be within a channel of the cavity and configure to receive at least a portion of the sterilizable connector and the transfer set connector. To this end, the channel may further comprise a transfer set connector interface that engages the transfer set connector to ensure the transfer set connector is in a correct configuration for sterilization. In some variations, the stopcock actuator comprises the hexagonally shaped projection and is disposed on the housing and the sterilizable connector comprises a corresponding hexagonally shaped recess configured to be actuated by the hexagonally shaped projection when seated within the sterilizable connector interface.

Specifically, as described further with reference to FIG. 25A-D, a transfer set connector can be positioned within a channel of a cavity of a fluid flow control device housing relative to a transfer set connector interface. The transfer set connector interface may be a protrusion and the like disposed at a predetermined distance relative to the sterilizable connector. The predetermined distance is such that that the transfer set connector cannot be properly seated within the channel unless a clamp of the transfer set connector is in an open configuration. When in the open configuration, fluid can flow through the transfer set connector.

Figure 25A:
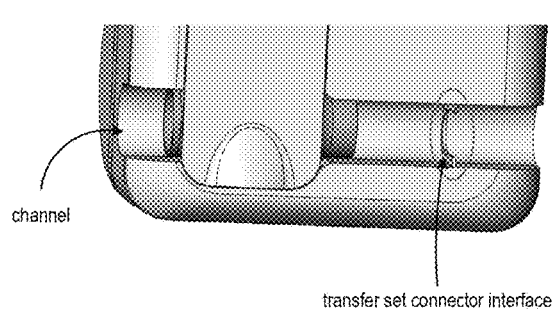
FIG. 25A is a rendering of a portion of a fluid flow control device, according to embodiments of the present disclosure. A sterilizable connector is coupled to the fluid flow control device. A transfer set interface feature is shown.
Figure 25B:
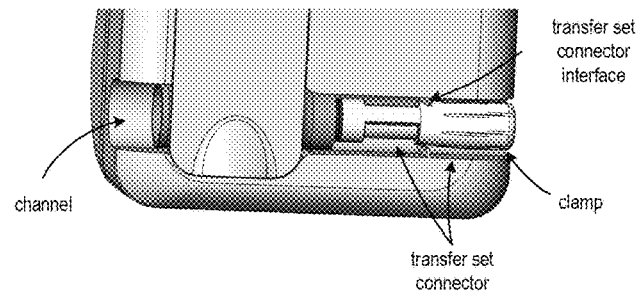
FIG. 25B is a rendering of a portion of a fluid flow control device, according to embodiments of the present disclosure. A sterilizable connector is coupled to the fluid flow control device and a transfer set connector is coupled to the sterilizable connector.
Figure 25C:
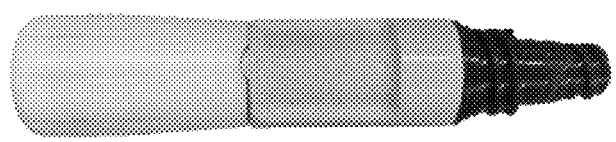
FIG. 25C is an image of a transfer set connector in a first configuration.
Figure 25D:
FIG. 25D is an image of a transfer set connector in a second configuration.

Notably, the transfer set connector is connected to the patient via the transfer set tubing between peritoneal dialysis treatment sessions. Accordingly, it is closed when peritoneal dialysis is not being performed in order to maintain sterility of the tubing. However, during peritoneal dialysis treatment, and immediately before when sterilization is being performed, the clamp of the transfer set connector must be in an open position to permit sterilization and protect the transfer set connector from damage due to pressurization. FIG. 25C and FIG. 25D illustrate the clamp of the transfer set connector in a closed configuration (FIG. 25C) and an opened configuration (FIG. 25D). During use, patients are instructed to open the clamp of the transfer set connector by twisting the clamp prior to insertion into the channel of the fluid flow control device. The transfer set connector interface prevents the transfer set connector from being properly positioned within the channel of the fluid flow control device if the clamp is closed.

Figure 26:
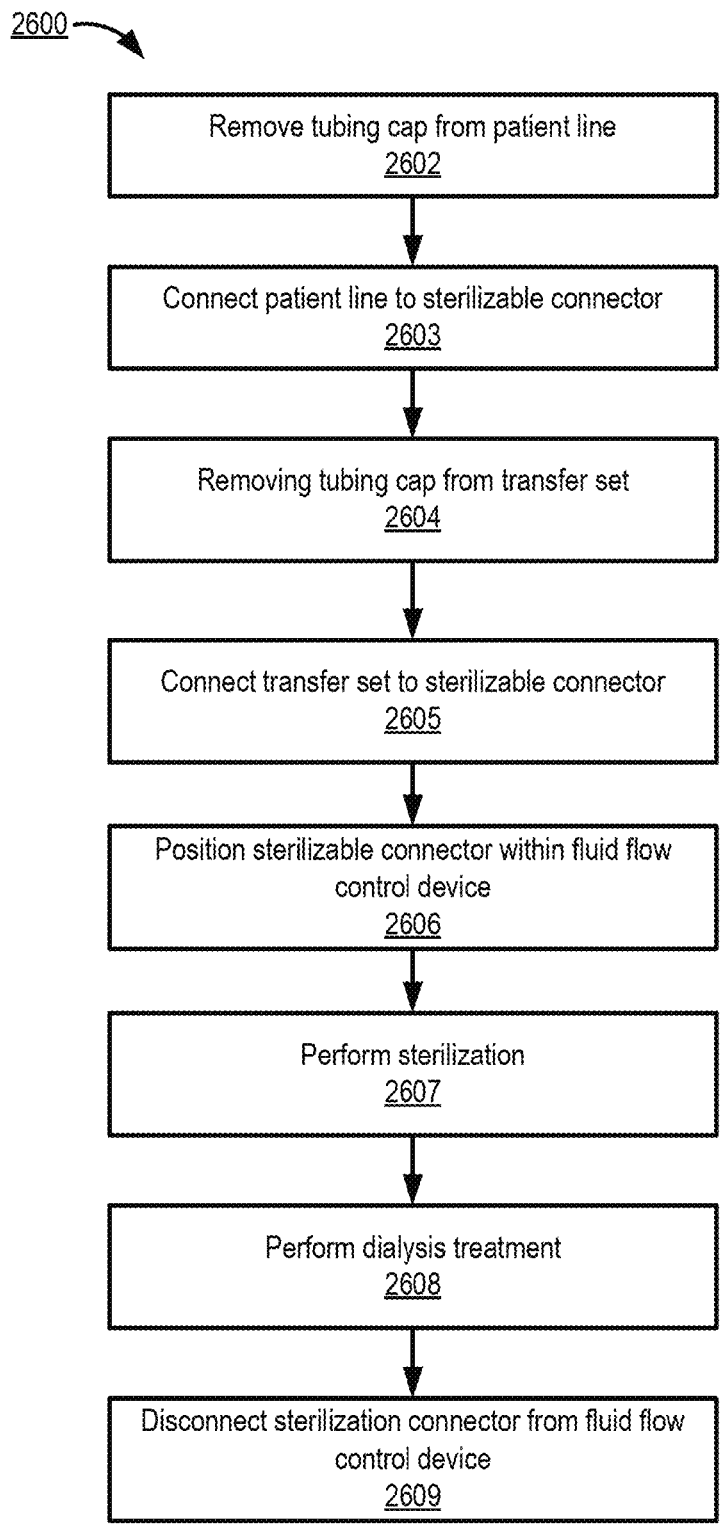
FIG. 26 is a flow diagram illustrating a user interaction with a fluid flow control device and a sterilizable connector, according to embodiments of the present disclosure.

With reference now to method 2600 of FIG. 26, aspects of a user experience will be described. The user experience may be better appreciated in view of FIG. 1.

At step 2602 of method 2600, a user removes a tubing cap from the patient line. In embodiments, a clamp at the end of the patient line may be opened. At step 2603 of method 2600, the patient line can then be coupled to a sterilizable connector of a fluid flow control device.

At step 2604 of method 2600, the user removes a cap from the transfer set. The cap may be engaged with a transfer set connector of the transfer set. The cap may be configured to maintain sterility of the transfer set between peritoneal dialysis treatment sessions. In embodiments, the cap may be similar to the cap described below with reference to FIG. 27. After removal of the cap from the transfer set connector, the transfer set connector may be connected to the sterilizable connector at step 2605 of method 2600.

To position the sterilizable connector within the fluid flow control device at step 2606 of method 2600, the user is instructed to and adjusts the clamp of the transfer set connector to the opened configuration. This is accomplished by gripping the clamp and rotating it counter-clockwise. Then, the user may position the sterilizable connector within the fluid flow control device, ensuring that the transfer set connector and a transfer set connector interface of a channel of the fluid flow control device are aligned. Alignment can also include aligning a stopcock actuation element of the sterilizable connector with a stopcock actuator of the fluid flow control device and aligning a fluid reservoir connected to the sterilizable connector with a fluid reservoir actuator of the fluid flow control device.

After assembly, and after the door of the fluid flow control device has been closed by the user, the sterilization can be performed at step 2607 of method 2600. The sterilization can be performed as described previously herein, with a predetermined sterilization fluid for a predetermined period of time.

In embodiments, the sterilization fluid may be as described above with reference to FIG. 22. Additionally, the sterilization fluid may be between about 0.001% and about 1% sodium hypochlorite, between about 0.01% and about 0.85% sodium hypochlorite, between about 0.15% and about 0.7% sodium hypochlorite, between about 0.2% and about 0.6% sodium hypochlorite, between about 0.3% and about 0.5% sodium hypochlorite, and between about 0.35% and about 0.45% sodium hypochlorite. In embodiments, the sterilization fluid may be between about 0.11% and about 0.55% sodium hypochlorite. In embodiments, the sterilization fluid may be 0.11% sodium hypochlorite. In embodiments, the sterilization fluid may be 0.55% sodium hypochlorite.

After disinfection, the user can perform a dialysis treatment at step 2608 of method 2600. Dialysis treatment may be e.g., an 8-12 hour process and may be performed accordingly to a prescribed protocol. A peritoneal dialysis treatment may include injecting a dialysate solution into the patient's peritoneal cavity using the patient line and transfer set. The solution is thereafter drained from the peritoneal cavity to the original solution container or elsewhere. Dialysate is delivered to the patient through e.g., the transfer set and then filtered back out to remove toxins and waste products from the body. This process can be done manually using gravity or with the use of a cycler to fill/drain fluid. The fluid is drained into drain bags that are connected to the patient via the peritoneal dialysis tubing. Waste, toxins, and excess water enter the solution from the patient's bloodstream through the peritoneal membrane. The transfer of waste, toxins, and water from the bloodstream to the solution occurs by diffusion and osmotic pressure.

After the dialysis treatment is performed, the user can open the door to allow the sterilizable connector to be removed from the fluid flow control device at step 2609 of method 2600. The clamp of the transfer set can be rotated clockwise by the user and closed. If present, the clamp at the end of the patient line can be closed. A new cap may be obtained for each of the patient line and the transfer set. The patient line and the transfer set can then be disconnected from the sterilizable connector and the new caps can be coupled to the tubing ends.

Figure 27:
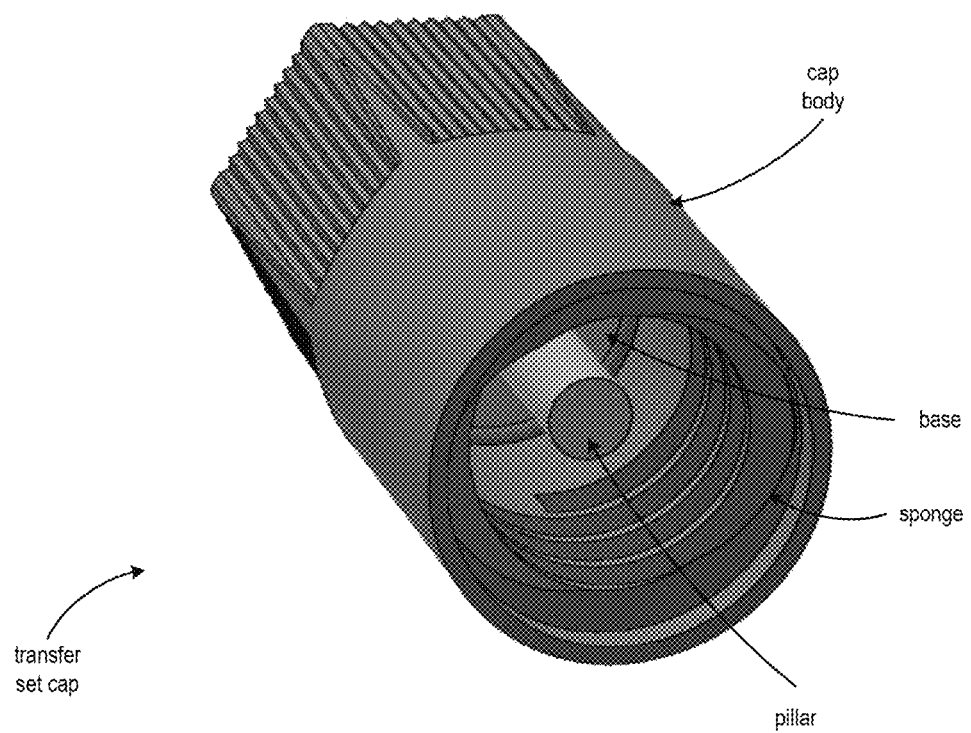
FIG. 27 is a rendering of a transfer set cap, according to embodiments of the present disclosure.

FIG. 27 is a rendering of a transfer set cap used to ensure sterility of the transfer set between peritoneal dialysis sessions.

The transfer set cap of FIG. 27 comprises a cap body and at least one sponge. The cap body may have an interior that is at least partially threaded to allow for coupling to a transfer set connector. The interior of the cap body may be configured to house the at least one sponge. As in FIG. 27, the at least one sponge may comprise a base and a pillar. The base may be seated within the interior of the cap body and may be configured for sterilization of an end of a transfer set connector when coupled thereto. To this end, the base may comprise a sterilization fluid such as povidone iodine (PVP-I). The pillar may extend from the base and be configured to enter into a lumen of the transfer set connector when coupled thereto. Specifically, the pillar may be any size and shape necessary to extend into a lumen of a transfer set connector and absorb fluids therein. In some embodiments, the base and the pillar of the at least one sponge are two or more sponges.

In embodiments, the pillar of the at least one sponge is at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, and/or at least 30 mm in length. Such a length permits the pillar of the at least one sponge to wick to a depth within the lumen of the transfer set connector of at least 5 mm, at least 6 mm, at least 7 mm, at least 8 mm, at least 9 mm, at least 10 mm, at least 11 mm, at least 12 mm, at least 13 mm, at least 14, at least 15 mm, at least 16 mm, at least 17 mm, at least 18 mm, at least 19 mm, at least 20 mm, at least 21 mm, at least 22 mm, at least 23 mm, at least 24 mm, at least 25 mm, at least 26 mm, at least 27 mm, at least 28 mm, at least 29 mm, and/or at least 30 mm in length. The outer diameter of the pillar of the at least one sponge should be sized according to an inner diameter of the lumen of the transfer set connector.

In embodiments, the at least one sponge is comprised of a polymer such as polypropylene, polyethylene, or blends thereof. In embodiments, a density of the base of the at least one sponge is higher than a density of the pillar of the at least one sponge. In this way, the base acts a reservoir for sterilization fluid. Both the base and the pillar, however, should be dense enough to retain fluid upon removing the transfer set cap from the transfer set.

In embodiments, sterilization fluid, such as PVP-I, from the base of the at least one sponge may diffuse into the pillar of the at least one sponge. In embodiments, the pillar of the at least one sponge may be pre-soaked with sterilization fluid. In embodiments, the pillar and the base are separated by a diffusion barrier to prevent cross-soaking of sterilization fluid.

In embodiments, the at least one sponge, or one or more of the base and the pillar, may be soaked with sterilization fluid at a predetermined volume. For instance, when the sterilization fluid is PVP-I, the predetermined volume may be between 0.1 grams and 0.4 grams of PVP-I, between about 0.15 grams and about 0.35 grams of PVP-I, and/or between about 0.2 and about 0.3 grams of PVP-I.

In embodiments, the at least one sponge, or one or more of the base and the pillar, may be soaked with sterilization fluid at a predetermined concentration. In embodiments, the predetermined concentration of the sterilization fluid may be between about 0.005% and about 20% PVP-I, between about 2.5% and about 12% PVP-I, and/or between about 8% and about 12% PVP-I. In embodiments, the predetermined concentration may be about 10% PVP-I.

Figure 28A:
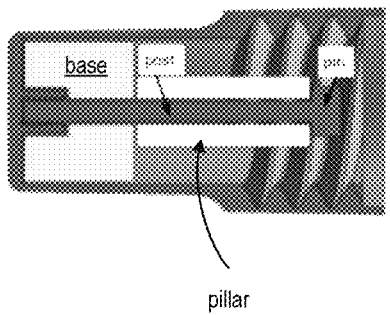
FIG. 28A-D are renderings of a transfer set cap, according to embodiments of the present disclosure.
Figure 28B:
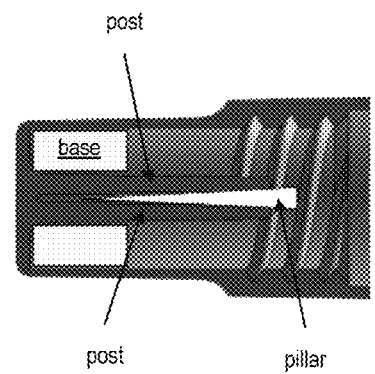
Figure 28C:
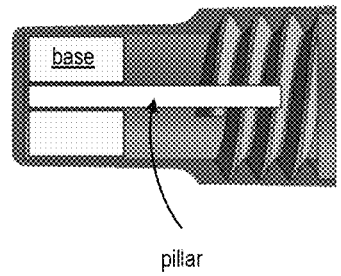
Figure 28D:
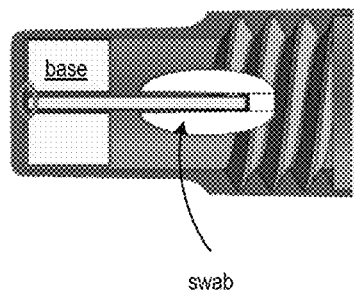

In embodiments, the at least one sponge can be coupled to the cap body by a variety of mechanisms, as shown in FIG. 28A-D. For example, the at least one sponge can be press fit into the interior of the cap body. Moreover, the pillar may be press fit into the base. In another example, the cap body may comprise a post protruding within the interior of the cap body, as shown in FIG. 28A. A pin may be positioned at the end of the post after the at least one sponge has been fitted within the interior of the cap body and around the post. In another example, as shown in FIG. 28B, the post may comprise at least two posts configured to secure the at least one sponge therebetween. Specifically, the base of the at least one sponge can be positioned in the interior of the cap body surrounding the post while the pillar of the at least one sponge is arranged between the at least two posts. In another example, as shown in FIG. 28C, the at least one sponge can be coupled to the interior of the cap body using adhesive. In another example, the at least one sponge is in the form of a swab attached directly to the interior of the cap body.

While various embodiments of the present disclosure have been described above, it should be understood that they have been presented by way of example only, and not limitation. Where methods described above indicate certain events occurring in certain order, the ordering of certain events may be modified. Additionally, certain events may be performed concurrently in a parallel process when possible, as well as performed sequentially as described above.

Although various embodiments have been described as having particular features and/or combinations of components, other embodiments are possible having a combination of any features and/or components from any of embodiments where appropriate.

The term "a" or "an" refers to one or more of that entity, i.e. can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

The term "coupled" is defined as connected, whether directly or indirectly through intervening components, and is not necessarily limited to physical connections. The connection can be such that the objects are permanently connected or releasably connected.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

Numbered Embodiments of the Invention

Notwithstanding the appended claims, the disclosure sets forth the following numbered embodiments:

(1) A system, comprising a fluid reservoir configured to store sterilization fluid, the fluid reservoir being engageable with a plunger, and a processor operatively coupled to an actuator and configured to control the actuator to move the plunger from a first position to a second position, maintain the plunger at the second position for a predetermined period of time, and move the plunger from the second position to the first position when the predetermined period of time lapses, wherein the movement of the plunger from the first position to the second position causes at least a portion of the sterilization fluid to be expelled from the fluid reservoir and into at least one medical line via a connector, and wherein the movement of the plunger from the second position to the first position causes at least a substantial majority of the expelled sterilization fluid to be retracted via the connector back into the fluid reservoir.

(2) The system of (1), wherein the fluid reservoir is a syringe barrel.

(3) The system of either (1) or (2), wherein the fluid reservoir and the plunger are disposable.

(4) The system of any one of (1) to (3), further comprising a plunger mount engageable with the plunger, and a fluid reservoir mount engageable with the fluid reservoir.

(5) The system of any one of (1) to (4), wherein the fluid reservoir mount and the plunger mount are reusable.

(6) The system of any one of (1) to (5), wherein a connection between the fluid reservoir mount and the fluid reservoir and the plunger mount and the plunger is one of a clamp mechanism, a screw mechanism, a twist mechanism, a press fit mechanism, or a snap fit mechanism.

(7) The system of any one of (1) to (6), further comprising an ejection mechanism configured to disengage the plunger from the plunger mount and the fluid reservoir from the fluid reservoir mount when the plunger is in the first position.

(8) The system of any one of (1) to (7), wherein the plunger mount is movable relative to the fluid reservoir mount to enable the movement of the plunger between the first position and the second position.

(9) The system of any one of (1) to (8), further comprising the actuator, the actuator being a linear actuator.

(10) The system of any one of (1) to (9), further comprising the connector.

(11) A method, comprising moving, via an actuator of a sterilization device, a plunger from a first position to a second position, the plunger being engageable with a fluid reservoir containing sterilization fluid, the moving the plunger from the first position to the second position causing at least a portion of the sterilization fluid to be expelled from the fluid reservoir and into at least one medical line via a connector, maintaining, via the actuator, the plunger at the second position for a predetermined period of time, and moving, via the actuator, the plunger from the second position to the first position when the predetermined period of time lapses, the moving the plunger from the second position to the first position causing a substantial majority of the expelled sterilization fluid to be retracted via the connector back into the fluid reservoir.

(12) A system, the system comprising a fluid reservoir having sterilization fluid therein, a connector in fluid communication with the fluid reservoir and with peritoneal dialysis tubing, a flow diverter fluidically-arranged between the fluid reservoir and the peritoneal dialysis tubing, and a processor configured to set the flow diverter to a first configuration configured to direct fluid flow from the fluid reservoir to a first portion of the connector coupleable to a first line of the peritoneal dialysis tubing, expel, via an actuator, at least a first portion of the sterilization fluid from the fluid reservoir and into the first line via the first portion of the connector, retract, via the actuator, a substantial majority of the expelled first portion of the sterilization fluid from the first portion of the connector, set the flow diverter to a second configuration configured to direct fluid flow from the fluid reservoir to a second portion of the connector coupleable to a second line of the peritoneal dialysis tubing, the second portion of the connector being different from the first portion of the connector, expel, via the actuator, at least a second portion of the sterilization fluid from the fluid reservoir and into the second line via the second portion of the connector, and retract, via the actuator, a substantial majority of the expelled second portion of the sterilization fluid from the second portion of the connector.

(13) The system of (12), wherein the processor is configured to expel the first portion of the sterilization fluid until a meniscus of the expelled first portion of the sterilization fluid extends into the first line by at least about 2 mm.

(14) The system of either (12) or (13), wherein flow diverter includes at least one of a stopcock, a valve, or a clamp.

(15) The system of any one of (12) to (14), wherein the fluid reservoir is a syringe, a bulb, a bag, or a cartridge.

(16) The system of any one of (12) to (15), wherein the actuator includes a diaphragm and is controlled via the processor to expel the first portion of the sterilization fluid and the second portion of the sterilization fluid and to retract the substantial majority of the expelled first portion of the sterilization fluid and the substantial majority of the expelled second portion of the sterilization fluid.

(17) The system of any one of (12) to (16), wherein the substantial majority of the expelled first portion of the sterilization fluid is retracted after a predetermined period of time lapses.

(18) The system of any one of (12) to (17), wherein the predetermined period of time is between about 1 second and about 30 seconds.

(19) The system of any one of (12) to (18), wherein the predetermined period of time is about 5 seconds.

(20) The system of any one of (12) to (19), wherein the sterilization fluid includes sodium hypochlorite.

(21) The system of any one of (12) to (20), wherein the sterilization fluid is between about 0.001 Molar and about 10 Molar sodium hypochlorite.

(22) The system of any one of (12) to (21), wherein the sterilization fluid is about 0.001 Molar sodium hypochlorite.

(23) The system of any one of (12) to (22), wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of between about 0.15 mL/sec and about 0.6 mL/sec.

(24) The system of any one of (12) to (23), wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of about 0.3 mL/sec.

(25) The system of any one of (12) to (24), wherein the fluid reservoir includes a syringe including a plunger and a barrel that defines an inner volume for containing the sterilization fluid, and the processor is configured to actuate a linear translation of the plunger relative to the barrel to expel the first portion of the sterilization fluid and the second portion of the sterilization fluid and to retract the substantial majority of the expelled first portion of the sterilization fluid and the substantial majority of the expelled second portion of the sterilization fluid.

(26) The system of any one of (12) to (25), wherein the plunger includes a circumferential channel along a portion of a circumference of the plunger, and a longitudinal channel along a portion of a longitudinal length of the plunger, the longitudinal channel and the circumferential channel being connected.

(27) The system of any one of (12) to (26), wherein the barrel includes an opening through a wall of the barrel, and the syringe further includes a locking element configured to extend through the opening and into at least one of the circumferential channel or the longitudinal channel.

(28) The system of any one of (12) to (27), wherein the barrel is movable between a first rotational position and a second rotational position to lock and unlock the linear translation of the plunger relative to the barrel.

(29) The system of any one of (12) to (28), wherein, when the barrel is in the first rotational position, the locking element is within the circumferential channel of the plunger and the plunger is translationally fixed relative to the barrel.

(30) The system of any one of (12) to (29), wherein, when the barrel is in the second rotational position, the locking element is within the longitudinal channel of the plunger and the plunger is configured to linearly translate along the longitudinal channel of the plunger to enable portions of the sterilization fluid to be expelled and retracted.

(31) The system of any one of (12) to (30), wherein, when the locking element is within the longitudinal channel of the plunger, the plunger is rotationally fixed relative to the barrel.

(32) The system of any one of (12) to (31), wherein the peritoneal dialysis tubing includes an extension of a peritoneal dialysis catheter and peritoneal dialysis set tubing.

(33) The system of any one of (12) to (32), wherein the first portion of the sterilization fluid and the second portion of the sterilization fluid are overlapping portions, identical portions, or different portions of the sterilization fluid.

(34) A method, comprising setting a flow diverter to a first configuration to direct fluid flow from a fluid reservoir to a first portion of a connector coupleable to a first line of peritoneal dialysis tubing, the flow diverter being fluidically-arranged between the fluid reservoir and the peritoneal dialysis tubing, the fluid reservoir having sterilization fluid therein, expelling, via an actuator, at least a first portion of the sterilization fluid from the fluid reservoir and into the first line via the first portion of the connector, retracting, via the actuator, a substantial majority of the expelled first portion of the sterilization fluid from the first portion of the connector, setting the flow diverter to a second configuration to direct fluid flow from the fluid reservoir to a second portion of the connector coupleable to a second line of the peritoneal dialysis tubing, the second portion of the connector being different from the first portion of the connector, expelling, via the actuator, at least a second portion of the sterilization fluid from the fluid reservoir and into the second line via the second portion of the connector, and retracting, via the actuator, a substantial majority of the expelled second portion of the sterilization fluid from the second portion of the connector.

(35) The method of (34), wherein the expelling the first portion of the sterilization fluid includes expelling the first portion of the sterilization fluid until a meniscus of the expelled first portion of the sterilization fluid extends into the first line by at least about 2 mm.

(36) The method of either (34) or (35), wherein the retracting the substantial majority of the expelled first portion of the sterilization fluid is performed after a predetermined period of time lapses.

(37) The method of any one of (34) to (36), wherein the predetermined period of time is between about 1 second and about 30 seconds.

(38) The method of any one of (34) to (37), wherein the predetermined period of time is about 5 seconds.

(39) The method of any one of (34) to (38), wherein the expelling the first portion of the sterilization fluid and the second portion of the sterilization fluid and the retracting the substantial majority of the expelled first portion of the sterilization fluid and the substantial majority of the expelled second portion of the sterilization fluid is performed at a rate of between about 0.15 mL/sec and about 0.6 mL/sec.

(40) The method of any one of (34) to (39), wherein the expelling the first portion of the sterilization fluid and the second portion of the sterilization fluid and the retracting the substantial majority of the expelled first portion of the sterilization fluid and the substantial majority of the expelled second portion of the sterilization fluid is performed at a rate of about 0.3 mL/sec.

(41) The method of any one of (34) to (40), wherein the fluid reservoir includes a syringe including a plunger and a barrel that defines an inner volume for containing the sterilization fluid, and the expelling the first portion of the sterilization fluid and the second portion of the sterilization fluid and the retracting the substantial majority of the expelled first portion of the sterilization fluid and the substantial majority of the expelled second portion of the sterilization fluid includes actuating, via the processor, a plunger of a syringe relative to a barrel of the syringe.

(42) A system, comprising a fluid reservoir having sterilization fluid therein, a connector in fluid communication with the fluid reservoir and with peritoneal dialysis tubing, a flow diverter fluidically-arranged between the fluid reservoir and the peritoneal dialysis tubing, and a processor configured to set the flow diverter to a first configuration to establish two fluid flow paths including a first fluid flow path configured to direct fluid flow from the fluid reservoir to a first portion of the connector and a second fluid flow path configured to direct fluid flow from the fluid reservoir to a second portion of the connector, the first portion of the connector and the second portion of the connector being fluidically-decoupled when the flow diverter is in the first configuration, each of the first portion of the connector and the second portion of the connector being coupled to different portions of the peritoneal dialysis tubing, expel, via an actuator, at least a portion of the sterilization fluid from the fluid reservoir and into each of the first portion of the connector and the second portion of the connector such that the portion of the sterilization fluid enters the peritoneal dialysis tubing, retract, via the actuator, a substantial majority of the expelled portion of the sterilization fluid from the first portion of the connector and the second portion of the connector, and set the flow diverter to a second configuration in which the first portion of the connector and the second portion of the connector are fluidically-coupled and peritoneal dialysis can be performed.

(43) The system of (42), wherein the processor is configured to expel the first portion of the sterilization fluid until a meniscus of the expelled first portion of the sterilization fluid extends into the first line by at least about 2 mm.

(44) The system of either (42) or (43), wherein flow diverter includes at least one of a stopcock, a valve, or a clamp.

(45) The system of any one of (42) to (44), wherein the fluid reservoir is a syringe, a bulb, a bag, or a cartridge.

(46) The system of any one of (42) to (45), wherein the actuator includes a diaphragm and is controlled via the processor to expel and retract the first portion of the sterilization fluid and the substantial majority of the expelled second portion of the sterilization fluid.

(47) The system of any one of (42) to (46), wherein the substantial majority of the expelled first portion of the sterilization fluid is retracted after a predetermined period of time lapses.

(48) The system of any one of (42) to (47), wherein the predetermined period of time is between about 1 second and about 30 seconds.

(49) The system of any one of (42) to (48), wherein the predetermined period of time is about 5 seconds.

(50) The system of any one of (42) to (49), wherein the sterilization fluid includes sodium hypochlorite.

(51) The system of any one of (42) to (50), wherein the sterilization fluid is between about 0.001 Molar and about 10 Molar sodium hypochlorite.

(52) The system of any one of (42) to (51), wherein the sterilization fluid is about 0.001 Molar sodium hypochlorite.

(53) The system of any one of (42) to (52), wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of between about 0.15 mL/sec and about 0.6 mL/sec.

(54) The system of any one of (42) to (53), wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of about 0.3 mL/sec.

(55) The system of any one of (42) to (54), wherein the fluid reservoir includes a syringe including a plunger and a barrel that defines an inner volume for containing the sterilization fluid, and the processor is configured to actuate a linear translation of the plunger relative to the barrel to expel the first portion of the sterilization fluid and the second portion of the sterilization fluid and to retract the substantial majority of the expelled first portion of the sterilization fluid and the substantial majority of the expelled second portion of the sterilization fluid.

(56) The system of any one of (42) to (55), wherein the plunger includes a circumferential channel along a portion of a circumference of the plunger, and a longitudinal channel along a portion of a longitudinal length of the plunger, the longitudinal channel and the circumferential channel being connected.

(57) The system of any one of (42) to (56), wherein the barrel includes an opening through a wall of the barrel, and the syringe further includes a locking element configured to extend through the opening and into at least one of the circumferential channel or the longitudinal channel.

(58) The system of any one of (42) to (57), wherein the barrel is movable between a first rotational position and a second rotational position to lock and unlock the linear translation of the plunger relative to the barrel.

(59) The system of any one of (42) to (58), wherein, when the barrel is in the first rotational position, the locking element is within the circumferential channel of the plunger and the plunger is translationally fixed relative to the barrel.

(60) The system of any one of (42) to (59), wherein, when the barrel is in the second rotational position, the locking element is within the longitudinal channel of the plunger and the plunger is configured to linearly translate along the longitudinal channel of the plunger to enable portions of the sterilization fluid to be expelled and retracted.

(61) The system of any one of (42) to (60), wherein, when the locking element is within the longitudinal channel of the plunger, the plunger is rotationally fixed relative to the barrel.

(62) The system of any one of (42) to (61), wherein the peritoneal dialysis tubing includes an extension of a peritoneal dialysis catheter and peritoneal dialysis set tubing.

(63) The system of any one of (42) to (62), wherein the first portion of the sterilization fluid and the second portion of the sterilization fluid are overlapping portions, identical portions, or different portions of the sterilization fluid.

(64) A method, comprising setting, via a processor, a flow diverter to a first configuration to establish two fluid flow paths including a first fluid flow path configured to direct fluid flow from a fluid reservoir to a first portion of a connector and a second fluid path configured to direct fluid flow from the fluid reservoir to a second portion of the connector, the fluid reservoir having sterilization fluid therein, the flow diverter being fluidically-arranged between the fluid reservoir and peritoneal dialysis tubing, the connector being in fluid communication with the fluid reservoir and the peritoneal dialysis tubing, the first portion of the connector and the second portion of the connector being fluidically-decoupled when the flow diverter is in the first configuration, and each of the first portion of the connector and the second portion of the connector being coupled to different portions of the peritoneal dialysis tubing, expelling, via the processor, at least a portion of the sterilization fluid from the fluid reservoir and into each of the first portion of the connector and the second portion of the connector such that the portion of the sterilization fluid enters the peritoneal dialysis tubing, retracting, via the processor, a substantial majority of the expelled portion of the sterilization fluid from the first portion of the connector and the second portion of the connector, and setting, via the processor, the flow diverter to a second configuration in which the first portion of the connector and the second portion of the connector are fluidically-coupled and peritoneal dialysis can be performed.

(65) The method of (64), wherein the expelling the first portion of the sterilization fluid includes expelling the first portion of the sterilization fluid until a meniscus of the expelled first portion of the sterilization fluid extends into the first line by at least about 2 mm.

(66) The method of either (64) or (65), wherein the retracting the substantial majority of the expelled first portion of the sterilization fluid is performed after a predetermined period of time lapses.

(67) The method of any one of (64) to (66), wherein the predetermined period of time is between about 1 second and about 30 seconds.

(68) The method of any one of (64) to (67), wherein the predetermined period of time is about 5 seconds.

(69) The method of any one of (64) to (68), wherein the expelling the first portion of the sterilization fluid and the second portion of the sterilization fluid and the retracting the substantial majority of the expelled first portion of the sterilization fluid and the substantial majority of the expelled second portion of the sterilization fluid is performed at a rate of between about 0.15 mL/sec and about 0.6 mL/sec.

(70) The method of any one of (64) to (69), wherein the expelling the first portion of the sterilization fluid and the second portion of the sterilization fluid and the retracting the substantial majority of the expelled first portion of the sterilization fluid and the substantial majority of the expelled second portion of the sterilization fluid is performed at a rate of about 0.3 mL/sec.

(71) The method of any one of (64) to (70), wherein the fluid reservoir includes a syringe including a plunger and a barrel that defines an inner volume for containing the sterilization fluid, and the expelling the first portion of the sterilization fluid and the second portion of the sterilization fluid and the retracting the substantial majority of the expelled first portion of the sterilization fluid and the substantial majority of the expelled second portion of the sterilization fluid includes actuating, via the processor, a plunger of a syringe relative to a barrel of the syringe.

The invention claimed is:

1. A system, the system comprising:
a fluid reservoir having sterilization fluid therein, the fluid reservoir being engageable with a plunger;
a connector in fluid communication with the fluid reservoir and with peritoneal dialysis tubing; and
a processor configured to:
expel, via an actuator operatively coupled to the plunger, the sterilization fluid from the fluid reservoir and into at least one of a first line of the peritoneal dialysis tubing and a second line of the peritoneal dialysis tubing via the connector by moving the plunger from a first position to a second position, and
retract, via the actuator, a substantial majority of the expelled sterilization fluid from the connector by retracting the plunger, after a predetermined period of time lapses, from the second position to a third position, wherein the third position is further from the second position than the first position and a further distance from the second position than a distance between the first position and the second position.

2. The system of claim 1, wherein the fluid reservoir comprises a syringe, a bulb, a bag, or a cartridge.

3. The system of claim 1, wherein the predetermined period of time is between about 1 second and about 120 seconds.

4. A system, the system comprising:
a fluid reservoir having sterilization fluid therein, the fluid reservoir being engageable with a fluid reservoir interface and with a plunger;
a plunger mount engageable with the plunger and the fluid reservoir interface;
a connector in fluid communication with the fluid reservoir and with peritoneal dialysis tubing; and
a processor configured to:
expel, via an actuator operatively coupled to the plunger via the plunger mount, the sterilization fluid from the fluid reservoir and into at least one of a first line of the peritoneal dialysis tubing and a second line of the peritoneal dialysis tubing via the connector by moving the plunger from a first position to a second position, and
retract, via the actuator, a substantial majority of the expelled sterilization fluid from the connector by retracting the plunger from the second position after a predetermined period of time lapses.

5. The system of claim 4, wherein the predetermined period of time is between about 1 second and about 120 seconds.

6. A system, the system comprising:
a fluid reservoir having sterilization fluid therein;
a connector in fluid communication with the fluid reservoir and with peritoneal dialysis tubing;
a flow diverter fluidically arranged between the fluid reservoir and the peritoneal dialysis tubing; and
a processor configured to:
set the flow diverter to a first configuration configured to direct fluid flow from the fluid reservoir to a first portion of the connector coupleable to a first line of the peritoneal dialysis tubing,
expel, via an actuator, a first portion of the sterilization fluid from the fluid reservoir and into the first line of the peritoneal dialysis tubing via the connector,
retract, via the actuator, a substantial majority of the expelled first portion of the sterilization fluid from the connector,
set the flow diverter to a second configuration configured to direct fluid flow from the fluid reservoir to a second portion of the connector coupleable to a second line of the peritoneal dialysis tubing, the second portion of the connector being different from the first portion of the connector,
expel, via the actuator, a second portion of the sterilization fluid from the fluid reservoir and into the second line of the peritoneal dialysis tubing via the connector, and
retract, via the actuator, a substantial majority of the expelled second portion of the sterilization fluid from the connector.

7. The system of claim 6, wherein the processor is configured to expel the first portion of the sterilization fluid until a meniscus of the expelled first portion of the sterilization fluid extends into the first line by at least about 1 mm.

8. The system of claim 6, wherein flow diverter includes at least one of a stopcock, a valve, or a clamp.

9. The system of claim 6, wherein the fluid reservoir comprises a syringe, a bulb, a bag, or a cartridge.

10. The system of claim 6, wherein the substantial majority of the expelled first portion of the sterilization fluid is retracted after a predetermined period of time lapses.

11. The system of claim 10, wherein the predetermined period of time is between about 1 second and about 120 seconds.

12. The system of claim 10, wherein the predetermined period of time is about 30 seconds.

13. The system of claim 6, wherein the sterilization fluid includes sodium hypochlorite.

14. The system of claim 6, wherein the sterilization fluid is between about 0.001 Molar and about 10 Molar sodium hypochlorite.

15. The system of claim 6, wherein the sterilization fluid is about 0.074 Molar sodium hypochlorite.

16. The system of claim 6, wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of between about 0.15 mL/sec and about 1.2 mL/sec.

17. The system of claim 6, wherein the processor is configured to expel the first portion of the sterilization fluid and the second portion of the sterilization fluid and to retract the substantial majority of the expelled first portion of the sterilization fluid and the substantial majority of the expelled second portion of the sterilization fluid, via the actuator, at a rate of about 0.3 mL/sec.

18. The system of claim 6, wherein the fluid reservoir includes a syringe including a plunger and a barrel that defines an inner volume for containing the sterilization fluid, and the processor is further configured to:
actuate a linear translation of the plunger relative to the barrel to expel the first portion of the sterilization fluid and the second portion of the sterilization fluid and to retract the substantial majority of the expelled first portion of the sterilization fluid and the substantial majority of the expelled second portion of the sterilization fluid.

19. The system of claim 18, wherein the plunger includes:
a circumferential channel along a portion of a circumference of the plunger, and
a longitudinal channel along a portion of a longitudinal length of the plunger, the longitudinal channel and the circumferential channel being connected.

20. The system of claim 6, wherein the fluid reservoir is engageable with a plunger, the actuator is operatively coupled to the plunger, and the processor is further configured to:
expel at least one of the first portion and the second portion of the sterilization fluid by moving the plunger from a first position to a second position, and
retract the substantial majority of at least one of the expelled first portion and the expelled second portion of the sterilization fluid by retracting the plunger from the second position after a predetermined period of time lapses.

21. The system of claim 20, wherein the fluid reservoir is a syringe barrel.

22. The system of claim 20, wherein the fluid reservoir and the plunger are disposable.

23. The system of claim 20, further comprising the actuator, wherein the actuator is a linear actuator.

24. The system of claim 20, wherein the processor is configured to control the actuator to retract the plunger by moving the plunger from the second position to a third position, the third position being further from the second position than the first position and a further distance from the second position than a distance between the first position and the second position.

25. The system of claim 20, further comprising a plunger mount engageable with the plunger and a fluid reservoir interface engageable with the fluid reservoir, wherein the actuator is operatively coupled to the plunger via the plunger mount.

26. The system of claim 25, wherein the fluid reservoir interface and the plunger mount are reusable.

27. The system of claim 25, wherein a connection between the fluid reservoir interface and the fluid reservoir is one of a clamp mechanism, a screw mechanism, a twist mechanism, a press fit mechanism, a snap fit mechanism, or a clearance fit mechanism.

28. The system of claim 25, wherein the plunger mount is engageable with the plunger by one of a clamp mechanism, a screw mechanism, a twist mechanism, a press fit mechanism, a snap fit mechanism, or a clearance fit mechanism.

29. The system of claim 25, wherein the plunger mount is movable by the actuator relative to the fluid reservoir interface to enable the movement of the plunger between the first position and the second position and retraction of the plunger from the second position.

* * * * *